(12) United States Patent
Gan et al.

(10) Patent No.: US 6,518,055 B2
(45) Date of Patent: Feb. 11, 2003

(54) ISOLATED HUMAN PROTEASE PROTEINS, NUCLEIC ACID MOLECULES ENCODING HUMAN PROTEASE PROTEINS, AND USES THEREOF

(75) Inventors: Weiniu Gan, Gaithersburg, MD (US); Jane Ye, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/816,093

(22) Filed: Mar. 26, 2001

(65) Prior Publication Data

US 2002/0137180 A1 Sep. 26, 2002

(51) Int. Cl.$^7$ .......................... C12P 21/06; C12N 9/00; C12N 9/64; C12N 1/20; C12N 15/00
(52) U.S. Cl. ...................... 435/226; 435/69.1; 435/183; 435/195; 435/219; 435/252.3; 435/320.1; 536/23.2; 536/23.5
(58) Field of Search ................................ 435/69.1, 183, 435/195, 219, 226, 252.3, 320.1; 536/23.2, 23.5

(56) References Cited

PUBLICATIONS

International Search Report filed Jul. 12, 2002.
Database GenBank, US National Library of Medicine, Accession No. AAB15495, MIYATA T. "New protein MEG–4 expressedin mesangial cells and DNA encoding it for tratent and diagnosis of deiseases associated with mesangial cells." Jan. 2001.
Database GenBank, US Natinal Library of Medicine, Accession No. AAW78247, Brewer et al., "New isolated human genes and the secreted polypeptides they encode useful fro diagnosis and treatment of e.g. cancers, neurological disorders, immune diseases, inflammation or blood disorders" April 1999.
Database GenBank, US National Library of Medicine, Accession No. AJ132637, Jun. 16, 2000, COPPOLA et al., "Identification and characterization of YME1L1, a novel paraplegin–related gene" Genomics 65 (1), 48–54, 2000.

Database GenBank, US National Library of Medicins, Accession No. AF090430, BUTTERWORTH et al., "A member of the FtsH/YME1 family of ATP–dependent metalloproteases from the mouse genome" Sep. 1998.
Database GenBank, US National Library of Medicine, Accession AAA95627, MIYATA et al., "New protein MEG–4 expressed in mesangial cells and DNA encoding it for treatment and diagnosis of diseases associated with mesangial cells." Jan. 2001.
Database GenBank, US National Library of Medicine, Accession No. AAV32419, AGOSTINO et al., "New nucleic acid encoding secreted protein from human cells–potentially useful, e.g. as immuno–modulators, antitumour agents, promoters of tissue growth, heaemostatic and thrombolytic agents." Oct. 1998.
Database GenBank, US National Library of Medicine, Accession No. AAV89108, AGOSTINO et al., "New polynucleotides encoding human secreted proteins–derived from e.g. human blood, kidney, foetal lung, placenta, testes, brain, ovary, pituitary, retina and colon cDNA libraries" Genetics, Inst. Inc. Fegruary 1999.
Database GenBank, US National Library of Medicine, Accession No. AX079575, BAKER et al., "Human polypeptides and methods fro the use thereof." WO 01/07611–A, Feb. 2001.
Database GenBank, US National Library of Medicine, Accessoin No. AAX04332, BREWER et al., "New isolated human genes and the secreted polypeptides they encode–useful for diagnosis and treatment of e.g. cancers, neurological disorders, immune diseases, inflammation or blood disorders." Apr. 1999.

*Primary Examiner*—Rebecca E. Prouty
*Assistant Examiner*—Manjunath N. Rao
(74) *Attorney, Agent, or Firm*—Celera Genomics; Lin Sun-Hoffman

(57) ABSTRACT

The present invention provides amino acid sequences of peptides that are encoded by genes within the human genome, the protease peptides of the present invention. The present invention specifically provides isolated peptide and nucleic acid molecules, methods of identifying orthologs and paralogs of the protease peptides, and methods of identifying modulators of the protease peptides.

23 Claims, 35 Drawing Sheets

```
   1 ATTTTCCGTT TCTGGGAGGA GTGAGGGGCA ACGGGTCGGA GAAAAGGAA
  51 AAAAGAAGGG CTCAGCGCCT CCCCGCCGGG CCGTGGACAG AGGGGCACAG
 101 TTTCGGCAGG CGGGTGAGGT CGCTGAGGGC CCGCCGGAGA TGTTTTCCTT
 151 GTCGAGCACG GTGCAACCCC AGGTTACAGT TCCTCTGAGT CATCTCATCA
 201 ATGCCTTCCA TACACCAAAA AACACTTCTG TTTCTCTCAG TGGAGTGTCA
 251 GTTTCTCAAA ACCAGCATCG AGATGTAGTT CCTGAGCATG AGGCTCCCAG
 301 CAGTGAGCCT TCACTTAACT TAAGGGACCT TGGATTATCT GAACTAAAAA
 351 TTGGACAGAT TGATCAGCTG GTAGAAAATC TACTTCCTGG ATTTTGTAAA
 401 GGCAAAAACA TTTCTTCCCA TTGGCATACA TCCCATGTCT CTGCACAATC
 451 CTTCTTTGAA AATAAATATG TTTTCATACA GTCTCGGGGT TTTAAAACTT
 501 TGAAATCAAG GACACGACGT CTCCAGTCTA CCTCCGAGAG ATTAGCTGAA
 551 ACACAGAATA TAGCGCCATC ATTCGTGAAG GGGTTTCTTT TGCGGGACAG
 601 AGGATCAGAT GTTGAGAGTT TGGACAAACT CATGAAAACC AAAAATATAC
 651 CTGAAGCTCA CCAAGATGCA TTTAAAACTG GTTTTGCGGA AGGTTTTCTG
 701 AAAGCTCAAG CACTCACACA AAAAACCAAT GATTCCCTAA GGCGAACCCG
 751 TCTGATTCTC TTCGTTCTGC TGCTATTCGG CATTTATGGA CTTCTAAAAA
 801 ACCCATTTTT ATCTGTCCGC TTCCGGACAA CAACAGGGCT TGATTCTGCA
 851 GTAGATCCTG TCCAGATGAA AAATGTCACC TTTGAACATG TTAAAGGGGT
 901 GGAGGAAGCT AAACAAGAAT TACAGGAAGT TGTTGAATTC TTGAAAAATC
 951 CACAAAAATT TACTATTCTT GGAGGTAAAC TTCCAAAAGG AATTCTTTTA
1001 GTTGGACCCC CAGGGACTGG AAAGACACTT CTTGCCCGAG CTGTGGCGGG
1051 AGAAGCTGAT GTTCCTTTTT ATTATGCTTC TGGATCCGAA TTTGATGAGA
1101 TGTTTGTGGG TGTGGGAGCC AGCCGTATCA GAAATCTTTT TAGGGAAGCA
1151 AAGGCGAATG CTCCTTGTGT TATATTTATT GATGAATTAG ATTCTGTTGG
1201 TGGGAAGAGA ATTGAATCTC CAATGCATCC ATATTCAAGG CAGACCATAA
1251 ATCAACTTCT TGCTGAAATG GATGGTTTTA AACCCAATGA AGGAGTTATC
1301 ATAATAGGAG CCACAAACTT CCCAGAGGCA TTAGATAATG CCTTAATACG
1351 TCCTGGTCGT TTTGACATGC AAGTTACAGT TCCAAGGCCA GATGTAAAAG
1401 GTCGAACAGA AATTTTGAAA TGGTATCTCA ATAAAATAAA GTTTGATCAA
1451 TCCGTTGATC CAGAAATTAT AGCTCGAGGT ACTGTTGGCT TTTCCGGAGC
1501 AGAGTTGGAG AATCTTGTGA ACCAGGCTGC ATTAAAAGCA GCTGTTGATG
1551 GAAAAGAAAT GGTTACCATG AAGGAGCTGG AGTTTTCCAA AGACAAAATT
1601 CTAATGGGGC TGAAAGAAG AAGTGTGGAA ATTGATAACA AAAACAAAAC
1651 CATCACAGCA TATCATGAAT CTGGTCATGC CATTATTGCA TATTACACAA
1701 AAGATGCAAT GCCTATCAAC AAAGCTACAA TCATGCCACG GGGGCCAACA
1751 CTTGGACATG TGTCCCTGTT ACCTGAGAAT GACAGATGGA ATGAAACTAG
1801 AGCCCAGCTG CTTGCACAAA TGGATGTTAG TATGGGAGGA AGAGTGGCAG
1851 AGGAGCTTAT ATTTGGAACC GACCATATTA CAACAGGTGC TTCCAGTGAT
1901 TTTGATAATG CCACTAAAAT AGCAAAGCGG ATGGTTACCA AATTTGGAAT
1951 GAGTGAAAAG CTTGGAGTTA TGACCTACAG TGATACAGGG AAACTAAGTC
2001 CAGAAACCCA ATCTGCCATC GAACAAGAAA TAAGAATCCT TCTAAGGGAC
2051 TCATATGAAC GAGCAAAACA TATCTTGAAA ACTCATGCAA AGGAGCATAA
2101 GAATCTCGCA GAAGCTTTAT TGACCTATGA GACTTTGGAT GCCAAGAGA
2151 TTCAAATTGT TCTTGAGGGG AAAAAGTTGG AAGTGAGATG ATAACTCTCT
2201 TGATATGGAT GCTTGCTGGT TTTATTGCAA GAATATAAGT AGCATTGCAG
2251 TAGTCTACTT TTACAACGCT TTCCCCTCAT TCTTGATGTG GTGTAATTGA
2301 AGGGTGTGAA ATGCTTTGTC AATCATTTGT CACATTTATC CAGTTTGGGT
2351 TATTCTCATT ATGACACCTA TTGCAAATTA GCATCCCATG GCAAATATAT
2401 TTGAAAAAAA TAAAGAACTA TCAGGATTGA AAACAAAAAA AAAAAAAAA
2451 AAAAAAAAAA CCAAAAAAAA AAAAAAAAA AAAAAAA
(SEQ ID NO: 1)
```

FEATURES:
5'UTR:        1 - 139
Start Codon:  140
Stop Codon:   2189
3'UTR:        2192

FIGURE 1, page 1 of 2

Homologous proteins:
Top 10 BLAST Hits:

```
                                                            Score       E
Sequences producing significant alignments:                 (bits)    Value
CRA|1000682317127  /altid=gi|7657689  /def=ref|NP_055078.1| YME1 ...   1338   0.0
CRA|18000005168962 /altid=gi|7305635  /def=ref|NP_038799.1| YME1...    1288   0.0
CRA|18000005213035 /altid=gi|4454688  /def=gb|AAD20962.1| (AF070...    1007   0.0
CRA|100000007603324 /altid=gi|9506353 /def=emb|CAB99462.1| (AJ2...     1005   0.0
CRA|164000136747567 /altid=gi|11990780 /def=emb|CAC19650.1| (AL...      855   0.0
CRA|108000024649810 /altid=gi|12735270 /def=ref|XP_011853.1| YM...      723   0.0
CRA|89000000194244  /altid=gi|7291497  /def=gb|AAF46922.1| (AE003...    580   e-164
CRA|18000005163857  /altid=gi|7488430  /def=pir||T02610 YTA11 pro...    512   e-144
CRA|18000004983819  /altid=gi|1730618  /def=sp|P54813|YMEH_CAEEL ...    510   e-143
CRA|150000075553175 /altid=gi|9757998  /def=dbj|BAB08420.1| (AB0...     505   e-142
``` dbEST:

```
                                                            Score       E
Sequences producing significant alignments:                 (bits)    Value
gi|12905045 /dataset=dbest /taxon=960...                     1495    0.0
gi|10949366 /dataset=dbest /taxon=96...                      1471    0.0
gi|12764516 /dataset=dbest /taxon=960...                     1400    0.0
gi|12098345 /dataset=dbest /taxon=96...                      1374    0.0
gi|11001321 /dataset=dbest /taxon=96...                      1366    0.0
gi|10999215 /dataset=dbest /taxon=96...                      1358    0.0
gi|12431013 /dataset=dbest /taxon=96...                      1320    0.0
gi|12947765 /dataset=dbest /taxon=960...                     1205    0.0
gi|10201627 /dataset=dbest /taxon=96...                      1098    0.0
gi|2080454  /dataset=dbest /taxon=9606 ...                   1072    0.0
```

EXPRESSION INFORMATION FOR MODULATORY USE:
gi|12905045 T cells from T cell leukemia
gi|10949366 Teratocarcinoma
gi|12764516 Prostate adenocarcinoma
gi|12098345 Adrenal gland- cortex carcinoma cell line
gi|11001321 Placenta
gi|10999215 Placenta
gi|12431013 Liver adenocarcinoma
gi|12947765 T cells from T cell leukemia
gi|10201627 Eye- retinoblastoma
gi|2080454  Pooled human meanocyte, fetal heart and pregnant uterus Tissue expression:
Whole liver FIGURE 1, page 2 of 2

```
  1 MFSLSSTVQP QVTVPLSHLI NAFHTPKNTS VSLSGVSVSQ NQHRDVVPEH
 51 EAPSSEPSLN LRDLGLSELK IGQIDQLVEN LLPGFCKGKN ISSHWHTSHV
101 SAQSFFENKY VFIQSRGFKT LKSRTRRLQS TSERLAETQN IAPSFVKGFL
151 LRDRGSDVES LDKLMKTKNI PEAHQDAFKT GFAEGFLKAQ ALTQKTNDSL
201 RRTRLILFVL LLFGIYGLLK NPFLSVRFRT TTGLDSAVDP VQMKNVTFEH
251 VKGVEEAKQE LQEVVEFLKN PQKFTILGGK LPKGILLVGP PGTGKTLLAR
301 AVAGEADVPF YYASGSEFDE MFVGVGASRI RNLFREAKAN APCVIFIDEL
351 DSVGGKRIES PMHPYSRQTI NQLLAEMDGF KPNEGVIIIG ATNFPEALDN
401 ALIRPGRFDM QVTVPRPDVK GRTEILKWYL NKIKFDQSVD PEIIARGTVG
451 FSGAELENLV NQAALKAAVD GKEMVTMKEL EFSKDKILMG PERRSVEIDN
501 KNKTITAYHE SGHAIIAYYT KDAMPINKAT IMPRGPTLGH VSLLPENDRW
551 NETRAQLLAQ MDVSMGGRVA EELIFGTDHI TTGASSDFDN ATKIAKRMVT
601 KFGMSEKLGV MTYSDTGKLS PETQSAIEQE IRILLRDSYE RAKHILKTHA
651 KEHKNLAEAL LTYETLDAKE IQIVLEGKKL EVR
    (SEQ ID NO:2)
```

FEATURES:
Functional domains and key regions:
[1] PDOC00001 PS00001 ASN_GLYCOSYLATION
N-glycosylation site Number of matches: 7
```
      1      28-31 NTSV
      2      90-93 NISS
      3    197-200 NDSL
      4    245-248 NVTF
      5    502-505 NKTI
      6    551-554 NETR
      7    590-593 NATK
```
---
[2] PDOC00005 PS00005 PKC_PHOSPHO_SITE
Protein kinase C phosphorylation site Number of matches: 11
```
      1      25-27 TPK
      2    120-122 TLK
      3    125-127 TRR
      4    132-134 SER
      5    193-195 TQK
      6    199-201 SLR
      7    225-227 SVR
      8    293-295 TGK
      9    616-618 TGK
     10    476-478 TMK
     11    605-607 SEK
```
---
[3] PDOC00006 PS00006 CK2_PHOSPHO_SITE
Casein kinase II phosphorylation site Number of matches: 12
```
      1    104-107 SFFE
      2    130-133 STSE
      3    156-159 SDVE
      4    232-235 TGLD
      5    236-239 SAVD
      6    314-317 SGSE
      7    316-319 SEFD
      8    452-455 SGAE
      9    476-479 TMKE
     10    586-589 SDFD
     11    612-615 TYSD
     12    625-628 SAIE
```
---

FIGURE 2, page 1 of 4

```
[4] PDOC00008 PS00008 MYRISTYL
N-myristoylation site

Number of matches: 6
       1        35-40  GVSVSQ
       2       233-238 GLDSAV
       3       253-258 GVEEAK
       4       292-297 GTGKTL
       5       324-329 GVGASR
       6       566-571 GGRVAE
-------------------------------------------------------
[5] PDOC00009 PS00009 AMIDATION
Amidation site Number of matches: 2
       1       354-357 GGKR
       2       676-679 EGKK
-------------------------------------------------------
[6] PDOC00017 PS00017 ATP_GTP_A
ATP/GTP-binding site motif A (P-loop)

289-296 GPPGTGKT
-------------------------------------------------------
[7] PDOC00572 PS00674 AAA
AAA-protein family signature 386-404 VIIIGATNFPEALDNALIR Membrane spanning structure and domains:
 Helix Begin    End   Score Certainity
     1   203    223   1.426 Certain
```

FIGURE 2, page 2 of 4

BLAST Alignment to Top Hit:
Alignment to top blast hit:
```
>CRA|1000682317127 /altid=gi|7657689 /def=ref|NP_055078.1| YME1
         (S.cerevisiae)-like 1 [Homo sapiens] /org=Homo sapiens
         /taxon=9606 /dataset=nraa /length=716
         Length = 716

Score = 1338 bits (3424), Expect = 0.0
 Identities = 683/716 (95%), Positives = 683/716 (95%), Gaps = 33/716 (4%)
 Frame = +2

Query: 140   MFSLSSTVQPQVTVPLSHLINAFHTPKNTSVSLSGVSVSQNQHRDVVPEHEAPSSEPSLN 319
             MFSLSSTVQPQVTVPLSHLINAFHTPKNTSVSLSGVSVSQNQHRDVVPEHEAPSSEPSLN
Sbjct: 1     MFSLSSTVQPQVTVPLSHLINAFHTPKNTSVSLSGVSVSQNQHRDVVPEHEAPSSEPSLN 60

Query: 320   LRDLGLSELKIGQIDQLVENLLPGFCKGKNISSHWHTSHVSAQSFFENKY---------- 469
             LRDLGLSELKIGQIDQLVENLLPGFCKGKNISSHWHTSHVSAQSFFENKY
Sbjct: 61    LRDLGLSELKIGQIDQLVENLLPGFCKGKNISSHWHTSHVSAQSFFENKYGNLDIFSTLR 120

Query: 470   -----------------------VFIQSRGFKTLKSRTRRLQSTSERLAETQNIAPSFVK 580
                                    VFIQSRGFKTLKSRTRRLQSTSERLAETQNIAPSFVK
Sbjct: 121   SSCLYRHHSRALQSICSDLQYWPVFIQSRGFKTLKSRTRRLQSTSERLAETQNIAPSFVK 180

Query: 581   GFLLRDRGSDVESLDKLMKTKNIPEAHQDAFKTGFAEGFLKAQALTQKTNDSLRRTRLIL 760
             GFLLRDRGSDVESLDKLMKTKNIPEAHQDAFKTGFAEGFLKAQALTQKTNDSLRRTRLIL
Sbjct: 181   GFLLRDRGSDVESLDKLMKTKNIPEAHQDAFKTGFAEGFLKAQALTQKTNDSLRRTRLIL 240

Query: 761   FVLLLFGIYGLLKNPFLSVRFRTTTGLDSAVDPVQMKNVTFEHVKGVEEAKQELQEVVEF 940
             FVLLLFGIYGLLKNPFLSVRFRTTTGLDSAVDPVQMKNVTFEHVKGVEEAKQELQEVVEF
Sbjct: 241   FVLLLFGIYGLLKNPFLSVRFRTTTGLDSAVDPVQMKNVTFEHVKGVEEAKQELQEVVEF 300

Query: 941   LKNPQKFTILGGKLPKGILLVGPPGTGKTLLARAVAGEADVPFYYASGSEFDEMFVGVGA 1120
             LKNPQKFTILGGKLPKGILLVGPPGTGKTLLARAVAGEADVPFYYASGSEFDEMFVGVGA
Sbjct: 301   LKNPQKFTILGGKLPKGILLVGPPGTGKTLLARAVAGEADVPFYYASGSEFDEMFVGVGA 360

Query: 1121  SRIRNLFREAKANAPCVIFIDELDSVGGKRIESPMHPYSRQTINQLLAEMDGFKPNEGVI 1300
             SRIRNLFREAKANAPCVIFIDELDSVGGKRIESPMHPYSRQTINQLLAEMDGFKPNEGVI
Sbjct: 361   SRIRNLFREAKANAPCVIFIDELDSVGGKRIESPMHPYSRQTINQLLAEMDGFKPNEGVI 420

Query: 1301  IIGATNFPEALDNALIRPGRFDMQVTVPRPDVKGRTEILKWYLNKIKFDQSVDPEIIARG 1480
             IIGATNFPEALDNALIRPGRFDMQVTVPRPDVKGRTEILKWYLNKIKFDQSVDPEIIARG
Sbjct: 421   IIGATNFPEALDNALIRPGRFDMQVTVPRPDVKGRTEILKWYLNKIKFDQSVDPEIIARG 480

Query: 1481  TVGFSGAELENLVNQAALKAAVDGKEMVTMKELEFSKDKILMGPERRSVEIDNKNKTITA 1660
             TVGFSGAELENLVNQAALKAAVDGKEMVTMKELEFSKDKILMGPERRSVEIDNKNKTITA
Sbjct: 481   TVGFSGAELENLVNQAALKAAVDGKEMVTMKELEFSKDKILMGPERRSVEIDNKNKTITA 540

Query: 1661  YHESGHAIIAYYTKDAMPINKATIMPRGPTLGHVSLLPENDRWNETRAQLLAQMDVSMGG 1840
             YHESGHAIIAYYTKDAMPINKATIMPRGPTLGHVSLLPENDRWNETRAQLLAQMDVSMGG
Sbjct: 541   YHESGHAIIAYYTKDAMPINKATIMPRGPTLGHVSLLPENDRWNETRAQLLAQMDVSMGG 600

Query: 1841  RVAEELIFGTDHITTGASSDFDNATKIAKRMVTKFGMSEKLGVMTYSDTGKLSPETQSAI 2020
             RVAEELIFGTDHITTGASSDFDNATKIAKRMVTKFGMSEKLGVMTYSDTGKLSPETQSAI
Sbjct: 601   RVAEELIFGTDHITTGASSDFDNATKIAKRMVTKFGMSEKLGVMTYSDTGKLSPETQSAI 660

Query: 2021  EQEIRILLRDSYERAKHILKTHAKEHKNLAEALLTYETLDAKEIQIVLEGKKLEVR 2188
             EQEIRILLRDSYERAKHILKTHAKEHKNLAEALLTYETLDAKEIQIVLEGKKLEVR
Sbjct: 661   EQEIRILLRDSYERAKHILKTHAKEHKNLAEALLTYETLDAKEIQIVLEGKKLEVR 716
 (SEQ ID NO:4)
```

Hmmer search results (Pfam):
Scores for sequence family classification (score includes all domains):

| Model | Description | Score | E-value | N |
|---|---|---|---|---|
| PF01434 | Peptidase family M41 | 409.5 | 2.2e-119 | 1 |
| PF00004 | ATPases associated with various cellular act | 300.5 | 2e-86 | 1 |
| PF01695 | IstB-like ATP binding protein | 11.4 | 0.061 | 1 |
| PF00158 | Sigma-54 transcription factors | 7.3 | 0.63 | 1 |
| PF00910 | RNA helicase | 7.3 | 0.53 | 1 |
| PF01202 | Shikimate kinase | 6.7 | 0.95 | 1 |
| PF00005 | ABC transporter | 6.1 | 1.4 | 1 |

FIGURE 2, page 3 of 4

```
PF01057   Parvovirus non-structural protein NS1         5.8    0.66   1
PF00406   Adenylate kinase                              4.4    4.2    1
PF01708   Geminivirus putative movement protein         3.8    7.4    1
PF00104   Ligand-binding domain of nuclear hormone rec  3.5    9.2    1

Parsed for domains:
Model     Domain   seq-f  seq-t     hmm-f  hmm-t      score   E-value
--------  -------  -----  -----     -----  -----      -----   -------
PF00104    1/1      255    267  ..     1     13  [.     3.5      9.2
PF00406    1/1      287    295  ..     1      9  [.     4.4      4.2
PF00158    1/1      285    302  ..    25     42  ..     7.3     0.63
PF01202    1/1      283    303  ..     1     21  [.     6.7     0.95
PF01057    1/1      285    303  ..   172    194  ..     5.8     0.66
PF00910    1/1      285    303  ..   126    144  ..     7.3     0.53
PF00005    1/1      285    305  ..     4     24  ..     6.1      1.4
PF01695    1/1      285    306  ..    52     73  ..    11.4    0.061
PF00004    1/1      284    469  ..     1    220  []   300.5    2e-86
PF01708    1/1      567    577  ..    76     86  ..     3.8      7.4
PF01434    1/1      475    674  ..     1    217  []   409.5 2.2e-119
```

FIGURE 2, page 4 of 4

```
   1 ACCTTTTGGA TTTAGAAACC TAACTCGCCG GGCGCGGTGG CTCACGCCAG
  51 TAATCCCAGC ACTTTGGGAG GCCGAGGCGG GAGGAATACG AGGTCAGGGA
 101 ATCGAGACCA TCCTGGCTAA CACGGTGAAA CCCCGTCTCT ACTAAAGAAA
 151 CCCCGTCTCT ACTAAAAATA CAAAAAATCA GCCGGGCGTG GTGACGGGCG
 201 CTTGTAGTCC CAGCTCGTCG GGAGGCCGAG GCAGGGGAAT GGCGTGAACC
 251 CGGGGGGCGG AGCTTGCAGT GAGTCGAGAT TGCGCCACTG CACTCCAGCC
 301 TGGGAAACAG AAGCAAGACTC CGCCTCAAAA AAAAATAAAA AAGAAACCTA
 351 ACTCAAGCCA GGGTGAGACT ACGAATCACG GCTTTGGCTT TAAGTGCCTG
 401 TTGTACTAAG ACCGATGTAA TCACCTCGGT CAAGTCCCTT TGCCTTTGGC
 451 CTCAGTTTCC TCATTTGCTA ACGCTGGGCA GGGAGAAGAG AGTCAAACTT
 501 TGCTGTTCTC ACTGTGCATC TGAGATATGG AGGGAAGGGC GGAACAGAGG
 551 CGAGACACCC GACCCGACCG CTGATGTCGC CCCAAAAAGA AGTCAGCTCG
 601 CAGGGCTCTG GAGGCTTCAG CAAGCCAGGC CACCCAGACT CCTCGCTCCA
 651 GCAACCCCGG GGCCTGCCCA AGCCGGTGGG GCAGGAAGGA GGGCCGAAGG
 701 GCCTAACCCC TTCCTTGCTA CTCGTTGACT TCCTACCTTT ACTGCATACA
 751 ATTTGCCGCC TTTCTGCCCC AGATACACTT TCCCGAAGGC GCCCCGGCTA
 801 ATGGGCTTCA CTATGCTGAA TTCCTCAATG GAGGGCGGTT TTGGCACTGC
 851 GATCCTATTC ACGCCCTCCT CAGTCGCCGC GCCTCCTCCA GGCTCCTTCT
 901 TGCTTCCCGC GGTGGGATCC ATCGCTGGAC AGCCTACAGC GGCCCCGCGT
 951 ACACTGCCCC TCCGCGAGCA GCCATTCCCG CCAACTGGGT TCAAAGTGAG
1001 GCTCCGCCCA CGCCGCGCGC GGCCGTGACG TCACCCCGCC GCCGCGCCCC
1051 GCCCTCGTCA CCTCCCCTAC GCAGACGCGC ACGGAGGGGG GCGTCGGGAA
1101 AGCCCCGACT TCGCAGCCTT ACACTCTTCG TGGGCGGCGA CCGCGGCCCC
1151 ACTGACATCA TTCCTCATGA GGGAGGAGGC ACAAACAGTT CTGGGCCGAC
1201 CAGAAAAAGG ACGACTGGGA CTTGACTCTG AATCGCAGGA TTTGAAGAGA
1251 TTTCTCCTGG CTTCCCAACG AGGCTGGTGG GAAGCGGTCC TCCTCCCATA
1301 CACGACCTCC CACCCTCGCG AGGCGTAGAA ACCAGTTCTG ACTGTACAGT
1351 AAAGCGAGGG CCAGGGCTGA GGTCTGGAAG CTAATGAAAG CACAGAAAGT
1401 GTCGAAACTG GATGAGCAGG AAGCGAGTGG CCTCCCCTGT CATCTGACGT
1451 TTTCCCAGGA TGTAATTTGC CTGACTGAAA CAGATCAGGA CCAACAGGGA
1501 GAGTTTTCGA TTTAGTGTGA GGAAAAGAGC ACTAAATTGT AGCAAAAGAC
1551 CTTATTGCTC AAGGCCCAGT CAGAAGATTT CATAAGGAAG CTGTAGAAAG
1601 TCTTAAGAGG AAATCAGCCG GGCGTGGTGG CGGGCACCTG TAATCCCAGC
1651 TACTCCGGAG GCTGAGGCAG GAGAATCGCT TGAACCCGGG GAGCAGAGGT
1701 TGCAGTGAGC CGAGATCGCG CCACTGTACG CCAGCCTGGG CGAAAGAACG
1751 AAACTCCGTC TCCAAAAAAA AAAAAAACGA AGAAAAGTC CAAAGAGGGT
1801 AAAGGCTGTT CTCCCCTTAA AAAACAGCTA AAGACCTTTG GGGGCGCTGC
1851 TCCTTGTAAA TGTCAACTAC TTCCGCGGGA AAGAACGCGC AGGCACTTGG
1901 CCTTGTGGGC GCTCACTTGC CCCGGAAGTA CTGTTGAGTT AGCGCCTCGC
1951 CTTCCGGGGC GGATTGTCTG TCGTTGCAGT AGCTGTAGGA AGGGGAGGCC
2001 ATTTTCCGTT TCTGGGAGGA GTGAGGGGCA ACGGGTCGGA GAAAAAGGAA
2051 AAAAGAAGGG CTCAGCGCCT CCCCGCCGGG CCGTGGACAG AGGGGCACAG
2101 TTTCGGCAGG CGGGTGAGGT CGCTGAGGGC CCGCCGGAGA TGTTTTCCTT
2151 GTCGAGCACG GTGCAACCCC AGGTAAGCCA GGCATTCAGC CCATTTTTTT
2201 TCCTCCCGCC CTGCCCGTGG CTGTTTGCAA ATTGCGCTCG TGGAAGCGAT
2251 TTCTCAGAAG GGACTCTAGA AATGAAGTGA TGTACTCAAT GCGAATCCCA
2301 GGATTGAGGA GTGGATCAGG GACGACGCT GAGAGTGGGC CGGAGACTTC
2351 AGTGCTGACG ATGAAGCTGT TGAGGGCAGA GGCGGGATGT GAGCTCAGTG
2401 ATAGAGAGAG ACCCTGGCTT ATCGAACTGA TTGCGTGGAA TTTCTGCTAG
2451 AGAATCCGTC CGGCATTGTT CAGTGTCCGG CGTTCTGGGG TGGGAAAATG
2501 TCTGTACCAT ACATTAAAGG GAGCAGGTAA TGTTCCCTTT TTTCCGACTT
2551 TCCAGTGGCT TTAGTGTTCA CAGCCCCTAT CCCCTGCTCT TTATTTCCTT
2601 TTAAATGGAA TTTAAATTTA ACCCAAACAT GGTATAATAT TTCGGATGGC
2651 CAGCCATGCA AGTTTTTTC TCATTTTGAC CAGAAGTAAC TAAAATGTGT
2701 ATTTCCGAGT CGTAAACTGT TTGCAGTTAA AATTTTGATT CAGCCTCATC
2751 CTCATCGTTT TGTAAAACAA AGGTAGTGA AGAGAAAAAT GATTTCAAGG
2801 GTTTTCATTA CGCTCTTGGG CAATCACTTG TGACAATGTT TTATTCTTGC
2851 TTCATTCCAG TCTCTTTTTT TGATGGTAAC ATTTTAATAG ATTTTTTGAG
2901 AGTTCCTACA GTTTTGCAAA GAAATAGTTT TTAAAACATT GAGTTTTTTT
2951 AAAACATAAT TTTTAAGAAA ATCGACACTC TTAGGTTCTT GATTTAAGCA
3001 TATGATTGTG TTCCTTTGTG TAACTTTTAC TCCCCCTCAT TTTAAGAATT
3051 TTTAATTTTT TGTGCTAGTA CTGGCTAACA AACTGAAGCA GCTGCTTGTT
3101 ATTGGGCATC AGTTATGTAC CAGGTGAGCA AAGCAAATGT GGAATCTTCT
3151 CTTAATATTG ATATGAAGTA AATATGAGTA GGACTTAGCA AGGTGAAGAG
3201 TGAACAGGTA TCACAGGCAT ACAGAAAAAT ACCTGGAGGT CCTGAGTTAG
3251 GAAAGGGTTT AGCAGGTTGA AGGAACAAAA ATAAGGCTAG TGTGGCTAGA
3301 ACATAGTAGT TAAAGGGGGT AGTGACAGAA GAGGTTGGAG AAAAGACTTG
3351 AGGCAGATCA TACAGGGAGT AAAGGATATA TTATGGCTGA TTTCATTTTA
3401 AGTGTATTGG GAACCATTGA AAGTTTTAAA ACATGATTAG ATTTTCATTT
3451 TTAAGAGATG ACTGGCTTTT GCTATATGGA GAATAGGAGA GGGCAAGAGT
3501 GGAAGATGTT ATCAGCTAAA AATACCCACC CACCCCCCAA TTAAAGCTGT
```

FIGURE 3, page 1 of 29

```
3551 TGCAGTGGTT ATGGAAAGAA GAGAATGAGA TATATTTTGA AGAAAGTGGA
3601 ATTGCATGAG AGATCAGAGA GATGATGGGG AGAGGTGTTT CTGGGTTTGA
3651 TCAGATGAAT GCATTGAAGG TGCTATTTAC CAAGATGACA GTGTCTGGAG
3701 AAGTCCTAGT AATTGTTTGA AAAAGAAGTC TGACATGGCC TATTGAATAT
3751 GGTATTGAAG TTTTTGAAAC TCAACTCTTT GCCTTAGTTC ACATCAAGAG
3801 GCCTGATTTT AGGAGAATTT ACCATCAACT GAATGGACAG TTAGTAGTAT
3851 GTGATGTTGG TAGAGATGAT AAAGGGATTT TTATGTACCC TAGGCAGTCT
3901 TAACAGGGCT CAAATATAGT GAGGACTCTC AGGCATTTCT TGCTTTGAAG
3951 GATGGTAACA CATTTGGAAT TCCTTGTTGC TTAATTGGTT GAATACACTT
4001 GAAATTAAAT GGTAAAAAGG AAGACACAGA AAATGAACTT TTTCATTGAG
4051 AAGAGCTCAA TTCTAAATCC TTTTGTGAAA GAAAAGAGAT ATAACTAATT
4101 CAAATAAAAG AGATATAACT AATTCAAATA AATCTTTTCA AAGAGGTAGA
4151 AAATATGTAT CTTGAAATGA TTTGATTATT TTTAAAGTTT CAAAAGAAGT
4201 TACTGTTTAT TTTTTTTTCT TTTTACTGCC CCCAGGCTGT AAGGAACTTA
4251 CTGTTTCTTT CTGACTCTAA AAATGATACA TTGCTTCACT TGACTAGCCT
4301 TAAAACAAAT CCATGTTTTT TTGCTAAAAA TGCTGAAAGT ATAAATAAGA
4351 TCGCCCATAA TCTCATTACT CAGGGATACG TATCTTAGAC TAAATTCTTT
4401 CACACATTTT TTTCTATAAA CAAACACGGG TATGCATACT TTTTTTTATT
4451 TTAATTTTTT TTTTTTTTTA AGATGGAGTC TCGCTCTGTC GCCCAGGCTG
4501 GAGTGCAGTG GCGCGATCTC CGCTCACTGC AAGCTCCGCC TCCCAGGTTC
4551 ACGCCATTCT CCTGCCTCAG CCTCCCAAGT AGCTGGGACC ACAGGCGCCC
4601 GCCACCACGC CCGGCTAATT TTTTGTATTT TTAGTAGAGA TGGGGTTTCA
4651 CCGTGTTAGC CAGGATGGTC TCCATCCCCT GACCTTGTGA TCCGTCCGCC
4701 TCGGCCTCCC AGAGTGCTGG GATTACAGGC GTGAGCCACC GCGCCCCAC
4751 GGGTATGCAT ACTTAAGGTA GTTTTACGGT CAGCTTTATT CCTTAGTATG
4801 TCACGAATTT ATTTGTGTAT CAATATCCAT GGGATGAGAA GTCTGGAATT
4851 TTGAGTCAGA TTCTAAATCT TTGTTGTCTT CATCTATTAA ATGGTCTGTA
4901 CCCACAATAA TGGCGTTAGT CCATTGATGA GGGCAGAGCC CTCCTGAACT
4951 AAATGCCTCT TAAAGGTCCC ACCTCTTAAC AGGATTACAG TGGCAACTAA
5001 GTTTGCCATT GTTCTCAACT CAAACTTGAG TTTTGAAGGA GATAAACACT
5051 GGAATTTTTA CTGGAAGTGG GCCCTGATCC AGACCCCAAG AGAGGGTTGT
5101 TGGATCTCGC ACAAGAATTC GAGAGAGTCG CCAGGCGCGG GGACTCACGC
5151 ATGTAATCCC AGCACTTTGG GAGGCAGAGG CGAGCGGATC ACGAGGTCAG
5201 GAGATCAAGA TCCTGGCTAA CATGGTGAAA CTCCATCTCT ACTAAAAATA
5251 CAAAAAAATA GCTGGGTGTG GTGGCCTGCG CCTGTAGTCC CAGCTACTCG
5301 GGAGGCTGAG GCAGGAGAAT CACTCGAACC CAGGAGGCGG TGGTTGCAGT
5351 GAGCCGAGAT TGCATCACTG CACTCCAGTC TGGGCGACAA AGCGAGATTC
5401 CATCTCAAAA AAAAAAAAAA AAAAAAAAGG CGAGAGAGTC TATAAAGTGA
5451 AAGCAAGTTT ATTAAGAAGG TAAAGGAGTA AAGAATGGGG TACTCCATAG
5501 GCAGAGGAGC TGCTTGGGCT TGTCCACGAA GGATACCTAC AGTTAGTTAT
5551 TTCTTGATTT TATGCTAAAC AATGTGTGAT TATTCATAAG TTTTCAGGGA
5601 AAGGGGGACC CCTAAGGTTC CTCCCCTTTT TAGACCACAT AGGGTAACTT
5651 CTTGATGTTG CCATGGCATT TTTAAACTGT CATGGTCTGG TGGGAGTGTC
5701 TTTTAGCATG CTAATGCATT ATAATTAGCA CATAATGAGC AGTGAGGACT
5751 AGCAGAAGTC ACTCTCCTCT CCATCTTAGT TTTGGTGGGA TTTGGCTGGC
5801 TTCCTTACTA CAACCTGTTT TATCATCACG GTCTTTATGA CCTGTATCTT
5851 GTGCCCACAC CCTATCTCAT CCTGTAACTT AGAATGCCTA ACCTCCTGGG
5901 AATGCAACCC AGTAGGTCTC AGCCTCATTT ACCCTCATTT TGCCCCTACT
5951 CCAGATGGAG TCACTCTGGT TCAAAGTCT CTGACAGAAC TGTAACAAGA
6001 AGTATAATTG TTACTCATTA TTATAGCTGT TTGAGGATTA AATGGGATGA
6051 TAGAAGTAAA GCCTGTAGTA CTAAACCTGG TATATAATAA GAACCCATTT
6101 AATGTATTCA TTTACTCAAC AAATATTTAT TAAGTAAATT TTTTTTTTTC
6151 TTGAGACAGG GTCTTGCCAT GTCATTCAGG CTGGAGTGTG GTGGCATGAT
6201 AGCTCACTGC AGCTTCAACT TCCTGGGCTC AAGTGTTTTT TTTGTTTTCA
6251 TTTTTATTTA TTTTATTTATT TTGACATGGA GTTTTGCTCT TGTCACCCAG
6301 GCTGGAATGC AATGGCATGA TCTTGGCTCA CTGCAACCTC CGCCTCCCAG
6351 GTTCGAGTGA TTCTCCTGCC TCTGCCTCCC AAGTATCTGG GATTACAGGC
6401 GCCCAACACC ATTCCTGGCC AATTTTTTTG TATTTTTAGT GGCGATGGGA
6451 TTTCACCACG TTGGCCAGGC TGGTCTCGAA CTCCTGACCT CAGGTATCTA
6501 CCTGCCTTGG CCTCCCAAAG TGCTGGGATT ACAGGCATGA GCCACCATTC
6551 CCGGCCTACT TACTATTTTT TTTTTTTTTA ATGTTGGATG TATTTCATTC
6601 TGTGGTAGTT TCCTTTTTTT TTTTTTTTTT TTTTTTTGA GAGACAGGTC
6651 TCACCCTGTT GCCCTGGCTA GAGTGCAGTG GCATGATCAC AGCTCACTGC
6701 AACTTCCGCC TCCTGAGATC AAGCAATTCT TCTACCACAG CCTCCCAAGT
6751 AGCTGAGACT ACAGGCGCAC ACCATCACAC CCATCTAATT GTTGTATTTT
6801 TTGGTAGAGA TGGGGTTTCA CTGTGTTGGT CAGGCTGGTC TTGAACTCCT
6851 GACCTCAAGT GATCCACCCA CCTCGGTCTC CCAAAGTGCT GGGGTTACAG
6901 GCGTGAGCCA CTGCACTCGA CCAGTGGTAT CATTTGTTTT GCCGCTCCCC
6951 TAATGCTGGA TGTTTCCAGC TTTCTACTAT TTTTTAAATG TTTCAATGAG
7001 AGTTGTTCTC TATGCATGTG CAAGTACTTG TCAGATTATT CCTTATAAT
7051 AAATTCCTAG AAGGTGGATT GCTACAAACA AGAAATGTAT GTATTTTTGA
```

```
 7101 TACTTTTGAT TTACATATTC AGAATAATAT CCTGAAAGAA CATACCAGTT
 7151 TTCGTCTCAC CAGCAGTAAA TCTGAGTACT TACAGTTTTT AGTATACAGA
 7201 GTTGATATAT AATGTACCTT TAACTCTTAA CAAATCCTGA CAAAAAAAGG
 7251 AGATTGTTCT GTTTATTTAA AAAAAAACTA CTTAATTTTT AACTTTTATC
 7301 TTTTTCTAGG TTACAGTTCC TCTGAGTCAT CTCATCAATG CCTTCCATAC
 7351 ACCAAAAAAC ACTTCTGTTT CTCTCAGTGG AGTGTCAGTT TCTCAAAACC
 7401 AGCATCGAGA TGTAGTTCCT GAGCATGAGG CTCCCAGCAG TGAGGTAAGT
 7451 CTTTATCCTG GTTGTGTGAG AAAGCCTTTT TGATATACAG TTGACCCTTA
 7501 AACAAATGAA GGATTAAGGA TATTGTCCCT CCCCCGTAGT CAAAAATTTG
 7551 AGTATAATTT TTGACTCCTG AGAAACTTAA CTACTAATAC CCTACTATTG
 7601 ACCAGGAAGC CTTGCCGATA AAATAAAGGG TCCATTAACA TATATTTTGT
 7651 ATATTTTATG TATTGTGTAC TGTATTCTTA CAATAAAGTA AGATGGAGAA
 7701 AATGTTATTA AGAAAATCAT AAGGAAGAGA AAATATATTT ACCATTCATT
 7751 AAGTAGAAGT GGACCATCAT AAAGATCTTC ATTATCTTCA AGTTGAGTGG
 7801 GCTGAGGAGG AAGAGGAGGG GTTGGTTTTT CTGTCTCTGG TGGCAGAGAC
 7851 CGGAGAAAGT CCACGTATCT GTGGATCTGT GCAGCTTTAA TCTGTGTTGT
 7901 TCAAGGATCA CCTGAGGTCA GGAGTTCAAG ACTAGCCTGA CCAATATGGT
 7951 GAAATCCCAT CTCTACTAGA AATACAAAAA TTAGCCGGGT GTGGTGGCGT
 8001 GCGCCTGTAG TCCCAGCTAC TCAGGAGGCT GAGACAAGAG AATAGCTTGA
 8051 GCCTAGGAGG CAGAGGTCGC TGTGAGCCAA GATCGCACCA CTGCACTCCA
 8101 GCCTGGGTGA CAACAAGACT CTGTCTCAAA AATAAATAAA TAAATAAATA
 8151 AATATAAAAA TGTAATCTCA TTTTTTGGTT TAATCTAAAA AAAAACACCT
 8201 GTTTTTACAG GGAAGTGGAA TAGGTAGGGA TTTAAGAAGT AAATAAAACT
 8251 CTTAAAAAAA TAAAGGACCA GCAGATTTAG GGAGCAGCTC ATACTTCTAG
 8301 GGCTGAGATA GAGTCAGGAA GAGTTCTCCA TCCCCAGGGC TGAGATCCTG
 8351 ACATTGTTGG CGAAGGCATG GCCTTGGCTC ACTGAATGGT AGAAAAGTTG
 8401 CTGTGATGTC ATGCCAGGGT AACGTCTGCA AAATCTGGGA AGTCTGCCCT
 8451 CTAGGATACT GGGAAAAGCT GTTCCTGGGG ATGTGTCCTA CTAGAGAAGC
 8501 TGTTACACGA GTGGTGCCAG GGGAAGCTGC TAGGTCCTGC TGGCCATTGT
 8551 GCACGCCAGG AGCCAGGGTT TGGTGAAACT GCACAATTGA CAGGAGCCAG
 8601 ATGCTATAGA AACCACGGGT GTTACAGACA GGAACTTGCT AAATGAGCAT
 8651 ACCACAACCA GGAATCAAAA CCTCTCTTCC TACAGTGTAT GTTCAGTGAC
 8701 TTCCTGACGA AGCTTAACAT TGTTTCAATT GGCAAAGGAA AAATATTCGA
 8751 AGGGTACAGA TCCATGTTCA TGGAGCCAGC AAAAAGGATG AAGAAGAGCT
 8801 TGGACACAAC CGATAACTGG CACATCCGTC CAGAACCCTT CTCCCTCTCA
 8851 ATCCCTGTAC ACTGCGGGTT TCTCCAAATG CCTATTGTCT ATGATTTGTT
 8901 TTGTCCATCG TTCTTAGTCA CGGCTTAGTT CAGGTTCTTG CCATCTTTCA
 8951 CTTGTTCCAT CAGCCTTCTC TCTCATCCAG TCTAGTTGCT TTGTTTGTTT
 9001 GTTTTATCAT TTTTAAATTT TTTGTAAAGA CAGGGTCTTG CTTTCTTCAC
 9051 CAGGCTGATC TCGAACTCCT GGCCTGAAGC AGTCCTCCCA CCTCAGCCTC
 9101 TCAAAAGTGT TGGGATTACA GGCTCGAGCC ACCATGCTAG GCCAGTCTAT
 9151 CTTCCTTAGT TCTCCATTTT CTTCTATAAG ACAGAACTAA TCATGTTACT
 9201 TAGAGAATTA AATTCAAACA TGGCTCTTCA CAGTTTGGCC ATAACCTATC
 9251 TCTTTAATTT TTTCTTTCCT TGAATTTTTT GAGATATTCC AGACCCTTGG
 9301 ATGGCTTTTT GTTTGCCCCC GTCCCTAAGC CGCCTTGATC ATTTTTAATA
 9351 GCTTAAAAAG TACTTTTAAG TATTTTATTT CATCATGCCT TTAACTGTCT
 9401 TTTACTATGT GCTGTCATGT TGTATGCTAG GATACGTAGA TGAGTAAGGC
 9451 ATGATCTCTG CCTTTGATCC TTACTATTAG GAAATAAGGT GTATTTTATA
 9501 GTTATGTTAG TATTGAGAAA ATGAATTCTA AGAATATGAG TTATAGCTAA
 9551 TTTAAAAAGT ACCGTATTCC CAGACATCAG TCCAGAGCTA TATAATCCGT
 9601 GTCCATGCCT CTTTTAAAAA AAACTTTATT TTTAGAGACA GGGTCTCCCC
 9651 TTTGTAGCCC AGGCTGAAGT GCAGTGATGC TGTCATAGCT CACTGCAACC
 9701 TCCAGCTCCT GGGCTCAAAC ATTTCTCCTG AGTAGCTGGT GCTGCGGGTG
 9751 CATACCACCA TGCCCAGCTA ATTTTTAAAT TTTTCATCAA GATGATGTCT
 9801 TACCATGTTG CTCAGGCTGG TCTCAAACTC CTGGCCTCAA ACGATCTTCC
 9851 CACCTTAGCT GTTTTGGGTT TGAGTAACAT GTAATTGTTA CTTGCCTTTA
 9901 AGTGCCTCTC TTTCAGCTCA TGTGGACAAG AAAATAATCC CTATCCTGTT
 9951 GTTTAAAAGT GGGTATACAC ACATTTTTGT GATTTTAGA CTTTTTTGCC
10001 TGATTTTCAC ACAGTTTTGA CTTTAATTTT CTTCTTTATT AGAAGATATG
10051 GGTAACTTTA GAACCTCTGA GTTCAAGGAA GGATCTAAGC AATGAGGCCA
10101 GAGGAGTGAG ATGTCCTATG GTAACCAAGC ATACCATTTC TTTGTCAAGT
10151 GGGCTTTTGT TTATGGCTGC TTAGGGGCTT AAAAGCTCCA TGGACTGGTG
10201 AGGATTATCA TTTGAATGGA ATTTCCCCAA TTCAAGAACC TTACTATTAT
10251 CCTCCAATCA GTTCTACACT GTTGGGGAAA ATCCCCTGGG CCTTATATAA
10301 CATACTTTGT AACCCTGCAG TTAGTTACTC TTACACTCTT GTCATTATAA
10351 ATGCTTGATC AATAGTTGAT AGACTAGCTC TTGATCAGAG TACCCTTGTA
10401 TGGAGAGAAG GAAAAAATGC CATACATTTC ACTTGATTCT GTGAACCATA
10451 ATGCTTAGGA CAGTAGTGGT TTGGGTTTGA TTTAAAAAAA AAAAGTTTT
10501 TCTCATTCAT GCTGAAATGT CATCTCTTTA TTTAAGGATA CCATTAGGAA
10551 TATAATTTTT TAACCTATGT CAAACCTCAT ATGACTGATC TCAGTAAAAC
10601 GAACTGTGAA AATATTTGCA TCAATTTATT TTTAAATATT AAAAAAAGGA
```

FIGURE 3, page 3 of 29

```
10651 AATATATTTG TTAGACTTTT AAAATCTGAT TGTTTTAACT GATAATATGT
10701 ACTCCTTAGG TTAAATATCT TGATAATATT AATGCATACC TGGTTGACCC
10751 AATCTTTTAC AGCCTTCACT TAACTTAAGG GACCTTGGAT TATCTGAACT
10801 AAAAATTGGA CAGATTGATC AGCTGGTAGA AAATCTACTT CCTGGATTTT
10851 GTAAAGGCAA AAACATTTCT TCCCATTGGC ATACATCCCA TGTCTCTGCA
10901 CAATCCTTCT TTGAAAATAA ATATGGTATG TTAATGTGTT TTTTGTTCCA
10951 ATTAAATATT TTAGCACTAT TAATAATTAT AGATACCATT TCTTAGCTTT
11001 CACAGTAGCG TTTATTGTGG GCTGGGTTCT TTCCTGAAGT GTTTTTTTTT
11051 TTGTTTTTTT TTTTGCAATT TTTCATATTG AAATAGTACC AGATTTACAG
11101 GAAAGTTGCA AAGATAGTAC AGAATTTTGC TTCCACTAAT TTTGGCATCT
11151 TACATAATCA TGTTACATTT GTTAAAACTA GGAAATTAAC ATTGGTACAA
11201 TAATTTTTTT TTTGAGACGG AGTCTCCTTC TGTCAGCCAG GCTGGAGTGC
11251 AGTGGCACAA TCTCCGCTCA CTGCAAGCTC CGCCTCCCGC GTTCACACCA
11301 TTCTCTTGCC TCGGCCTCCC AAGTAGCTGG GACTACAGGC GCCCGCCACC
11351 ACGCCCGGCT AATTTTTTGT ATTTTTAGTA GAGATGGGGT TTCACCGTGT
11401 TAGCCAGGAT GATCTTGATC TCCTGACCTC GTGATCCACC CTCCTCAGCC
11451 TCCCAAAGTG CTGGGATTAT AGGCGTGAGC CACCGTGCAG GCCTAACATT
11501 GGTACCTTAT TTTTAACTAA ACTACAGACT ATTTGAATTT CAACAAAATT
11551 TGTTTTCACC AAATCACTAG TTCTCTGCAA GTGTCCTTTT TCTTTTCCAG
11601 GATCTGATCC AGCATACCAC ATTGCATTTA GCAGAATGGG GGGGCGGTGT
11651 TTGTTTTAAT TTTAGGTGAC ACACATTTAA TTCCAGGAAA CATACTTAAT
11701 CTTTGAGAAT ACATTGATTA AAAAACAGT TGTTATCCCT TTTGTGGAAT
11751 GTCTACATTT TTTTTTACTT GAATCTCATA ACAGTATGGT AGTATAATAA
11801 GTGGGTTCAT ACTAGTCTGA AAAGGGATGT CAACTTTATG AGTTTTTCTT
11851 TGGATGGCAC TTAAACAGGC CATAAAAATC CAGGAACAAA ATAGCAGGTT
11901 TGACTAGTTT ATAATGAAGG TTTGATTTGA AGCTGTCCTT TGCATAAACT
11951 TAATTCATTA ATTCTTGACC CTTCCTTTGC CTTTATTTCA GTGTAAGGGC
12001 ATAAAAAACC GTAAGTGTGA GGAAAAAATG AAATGGTTTT GAGCTTGGGG
12051 GCTTAGACTA AAAGTTTGCC TCTGCCTAAA GTTGCCTTCT TATAAAAATAT
12101 TTGGCCCATA CCAAGTGTTC AATAGAATAA AATTCTTTTT GTTACTATGT
12151 TATTATGATT ATTCCTACTG CTCTTCTAGT CTGCATATTT ACATTTACTC
12201 TTAAGATTGT TCCTCATACC ACCAGCTGCT TGCTAGGTTT AGGCAGGCAG
12251 AGGTATTAGG AAGAGATTTT TTGACTGGAT GCTAAGGGAC CTTGAAAAAA
12301 GTCCCTAAAT TCTAACTGAG ACACACAAAT AGATGATAGC CACTGTTTGT
12351 TTCTGCTGTT GCTGCTGATG ACCTTTTCCC TAGGATCTTG GATATAAAAT
12401 AGGATGAGAC ACACTAGTCA AGAGAAGCAG TTAGGAAGGA TCAGTGAAGT
12451 ATTCATGGCT TGACCTTTCT TTTTACCCAA TGACTAGGGA AGCTTTATGA
12501 GGGAAAGATA ATAGTAGCTA TGATTCACAG TGTTTTATTA TACCATTAGA
12551 GCTTTTGAAA TTGTCTCTAA GAAACAGCAG TTCTTTATCT CTTTATGTTC
12601 TTAACTAAAA GTAATTTTAG CCTAAACACA GTACATCTTT TTTTTTTTTT
12651 TTTTTAAAGA GACGAGTCTT GCTGTGTTGC CCAGGCTGGA GTGCAGTGGG
12701 GCAATCTCGG CTCACTGTAA GCTCTGCCTT CCCAGTTCAC GCCATTCTCC
12751 TGCCTCAGCC TCCCGAGCAG CTGGGACTAC ACGCATCCGC CACCACGCCC
12801 GGCTAATTTT TGTATTTTTA GTAGAGACGA GGTTTCACCA TGTTAGCCAG
12851 GATGGTCTGT ATCTCCTGAC CTCGTGATCC GCCCGCCTCA GCCTCCCAAA
12901 GTGCTGGGAT TACAGGCGTG AGGCACCGCG CCTGGCCTTA AACACAGTAC
12951 ATCTTTTATC ACTGGTTTTG TTTTGTTTTG TTTTTGAGAC TGAGTTTCAC
13001 TCTTGTTGCC CAGGCGGGAG TGCAATGGCG CGATCTCAGC TCACCACAAC
13051 TTCTCCCTCC CGGGTTCAAG TGATTCTCCT GNNNNNNNNN NNNNNNNNNN
13101 NNNNNNNNNN NNNNNNNNNN NNNNNNNNNN NNNNNNNNNN NNNNNNNNNN
13151 NNNNNNNNNN NNNNNNNNNN NNNNNNNNNN NNNNNNNNNN NNNNNNNNNN
13201 NNNNNNNNNN NNACGCCACT GCACTCTAGC CTGGGCGACA GAGCAAAACT
13251 CCATCTCAAA AAACAACAAC AAAACAAACA AAAAAGGCAA GACCCGGCCA
13301 GGCGCGGTGA CTTACGCCTG TAATCCCAGC ACTTTGGGAG GCCGAGGAGG
13351 GTGGATCACG AGGTCAGGAA ATCGAGACCA TCTTGACTAA CAGTGAAACC
13401 CTGTCTCTAC TAAAAATACA AAAAATTAGC TGGGCGTGGT GGCCGGCGCC
13451 TGTAGCCAGT CCCAGCTACT CGGGAGGCTG AGGCAGGAGA ATGGCGTGAA
13501 CCCGGGAGGC GGAGCTTGCG GTGAGCCGAG GTCGTGCCAC TGCACTCCAG
13551 CCTGGGCGAC AGAGCGGGAC TCCGTCTCAA AAAAACAATA AATAAATAAA
13601 AATAATGTAA CCAACAAGTG ATAGCTAGTA AATGGAAGAA CTGTGAGATG
13651 TAGTTAAATT AGCGATGCTT TAGATATTTT CATAAAAGCA GTCATATCAT
13701 GGATAAATAA AAGTTGAAAC TCATATTGTG ATTTCCCTAA TATTTGATAG
13751 AATTATTTAT ATTTCATAGG ATTTTTGTTT TTGGTTTGG AAATTAGAAA
13801 ATTTACTTTT TGCAATTTCC CTCCAGGTAA CTTAGATATA TTTAGTACAT
13851 TACGTTCCTC TTGCTTGTAT CGACATCATT CAAGAGCTCT TCAAAGCATT
13901 TGTTCAGATC TTCAGTACTG GCCAGGTATG AAGCAACAAC CATAAATTGT
13951 GGAAAAAAAA ATATTTATTT ACTATAGTCT GATTTGTCTT TCTTAATGGT
14001 ATTAATTCTA AACATTCATT TGCAATTCAC AGGACCTAAA GAGTATTTGG
14051 AATTAATGAG TTTGGGTACT TCTGTATAAT TTTTAATCTG GAAATATAT
14101 AGGAGCTAAA TTTTGAGCGT GATAGTGCCA CAATAAATCA AACTCCAGGG
14151 AACTTATCTA CGCTTGTTTC AAGATAAATG ACTAACCACA TTTGCTTACT
```

FIGURE 3, page 4 of 29

```
14201 CATCCTCACT TTCAAAAGCC CATTGAAATT AATTTTATAT ATATATATAT
14251 GAGAAAAAAA GAGCAACAAC AGAAGCGTTC CGTTAACGGA CGAGAAATTT
14301 GAGGGCTTTC AGTAAGTTGT AAAATAAGTG ACATCAAATT GACAGTAAAA
14351 TCAAATTTGC ATTTATTCAT ATAATTTTTG AATACAAGGC ACTAGTGATA
14401 GATGTCAGGT GATAGTGATC ACTGTAAATG AAAAAGACAT GTTTTCTACC
14451 TTCATGGGAC TAATGGTGTC ATGAAAGAGG TGGGTACTTC TGTTTCCAGT
14501 AGTAGAACTC AGGAAAAACC CCACTTCCAG AGCCAGTAAA ATTGGGCACT
14551 GGGATGGGAT GGAATAAACA GTTGAAGATT GCCAGAAATG GGCCAATCAC
14601 AGTGCAGATA TGGCCTTTAA CCTTTAGATA AATTAGCAAA AAACACCTTT
14651 CTAATAAGAC GTCTGTGTGT GTGTGTGTGT GTGTGTGTGT GTGTGTGTGT
14701 GTGTGTGTCG AGGGACATCT GTCTGTGGAG ACTCCTGGTT TGAGCATTGA
14751 TGCCAAGGAA AGAAAGAAGC TAGCACCCCA GATTACTTTG GTTTTGAATT
14801 ACACATTCGC TAAAGTATTC TGCTCATTTA GCATAGTCCA TGTTTTATAT
14851 TCTAAGTATA TTTACTTTTG CTAGTGTTGA GGATACCCAT TTGTAGTCAA
14901 TACTGATGAC TGTATTTGTT TTGTTTTGTT TTGTTTTTGA GATGGAGTTT
14951 TCCTCTTGTG ACCCAGGCTG GAGTGCAGTG GCACTTCCTG GGTTCAAGCA
15001 ATTCTCCTGC CTCAGCCTCC TGAGGAGCTG GGATTACAGG TTCCCACCAC
15051 CAGGCCCAGC TAATTTTTGT ATTTTTAGTA GAGACGGGGT TTCACCATGT
15101 TGGCCGGGCT GGTCTCAGAA CTCCTGACCT TAGGTGATCC GCCTGCCTTG
15151 GCCTTCTAAA GTGTTGGGAT GACAGCATGA GCCACGGTGC CAGGCCCTGA
15201 TCACTGTATT CTTATTTATA AATACAAATG GATTACCAAG AATCCACATA
15251 TTTGAGGAAA ACTTAAAGCA TAAAAGAGAG GCACCAATTT CAGCAAAGAG
15301 ACTAATAACC CTCTAAAGAA ATAGTTAATG CAGAAGACAG AAGAAGACAG
15351 CTGATACGTT TTTAGCTATT GTTGGAAGAT GTATAAAAAC TGAGCGTGTG
15401 TTACCTAGGG TATGAAAACT ATCTTAATAA ATTTTCCTAA TGTTGTAACT
15451 CTGAGGTTAG ATTCTCTCAA TGTCAGAAAA TAAAGATAAA AATCCAGTAA
15501 CAGAAAAGAC AGCTTAAAAA AATACCTAAA TACGGCCAGG CACAGTGGCT
15551 TATGCCTGTA ATCCCAGCAC TTTGGTAGGC CGAGGAGGGT GGATCACAAG
15601 GTCAGAAGTT CAAGACCAGC CTGGCCAACA TAGTGAAACC CCATCTCTAC
15651 TAAAAATACA AAAATTAGCC AGGCATGGTG GCGTGTGCCT GTAATCCCAG
15701 CTACTTGGGA GGCTGAGGCA GGAGAATCAC TTGAACCCAG GAGGCGGAGG
15751 TTGCAGTGAG CCGAGACCGC GCCACTGAAC TCCAGCCTGG CAACAGAGCG
15801 AGACTCCGTC TCAAAAAACA AAAAAGACAA AAAAAACCTA AATACTTGAA
15851 ATTTTTAAAA CCCTTTTCTA AATGTCTCAC GACTGAATGG AAATAAAACC
15901 GGGATTACAG ACACTCAGTA ATGAACCACA GTGAAAATCT GTATATCAGA
15951 CTCTTGGTGA GGACAAAATG ACATTGAGGG CGTTATATAA TTTACTGAGA
16001 AATCAGGCTG GATGCAGTGG CTTATGCCTG TAATCCCAGC ACTTTGGGAG
16051 GCTGAGTCAG GTGGATCACC TGAGGTCGGG AGTTCAAGAC CAGCATGGCC
16101 AACATGGTAA AACCCCGTTC TCCACTAAAA AAGAAATACA AAATTAGCCA
16151 GGTGTGGTGG CACATGCCTG TAATCTCAGC TACTCGGGAG GCTGAGGCAG
16201 GATAATCGCT TGAACCTGGG AGATGGAAGT TTCAGTGAGC CAAGATGGCA
16251 CCTCCATCCT GGGCAACAGA GCAAGACTTT GTCTCAAAAA GAAAAAAAAA
16301 TTTAAGACAT AAAGATAGAA AATAAATTGA ATTTCTGAAA AATAATAGAA
16351 GAAATTAATA CACACAAAGC AAACATTTTA AATAATAGTG TGGAAATAGT
16401 TTTAATTAAA CCAAAAACAA ATTTAGTATA AAAAAGGAA CAATTTAACA
16451 ATTCTGATTA AGAAACAACA GGAAAATACA GACAGTATTA GAAGTATGAG
16501 TGGGAATTGC CATGGATATG TGAAGGTTTT AAAATTGCAA GGTAGTATGT
16551 GTAACTTTAT GTCATAAATA AAAATATGTT GAAATGGACA ATTGTCTAAG
16601 CAATTAATTA ACAAAGTTAA CCCAAGAAGA GATAGGATAA TAACCATGAA
16651 GTTTAAAAGA CAGTATTTTA AAAATATTGT CCCTTTGCCC CAGAGGCACT
16701 AGGTTCAGAT AATTTTTATG GCTGCATTCT TCTAGAATCT TGAGTTTCTT
16751 TTTAATTTAA AACCTTATTA AAAAGAAAAA GATAGAGTTC CCTATTTATT
16801 CCATGAGATT GCTGTTAGTA AAACTTTTTA GTATTAGCAT AAGGCCAGGC
16851 ACTGTGGATC ACACCTGTAA TCCCAACACT TTGGGATGAT CGCTTGAAGC
16901 CAGGAGTTCA AAACAAGCCC AGACATCATC TCAACAACAG CAACAAAAAT
16951 TAGCCCGTCG TGGTATCATG CCCCTGTAGT TCTGGATACT TGGGAGGCTG
17001 AGGTGAAAGG TTTGCTTGAG CCCAAAGTTC AAGGTTACAG TGAGCTATGA
17051 TCATGCCACC GTACTTCAGC TTGAGTGACA GCAAGATCCT ATCTAAAAAA
17101 TATATATATG TATATATGTA TGTATCTGTG TCTGAATGTA TATACACACG
17151 CAAGCACGAC AGAGGAACAA AATAGATGTG TTTCACTTAA CAGAAATCCT
17201 AAATAAAATC TGAAGAAAGC AAATCTAGAA ATGTGCTAAA AATATTTATAT
17251 CATGATTAAG GAATACAAAA GTGATTTAAG ATTATTAGTA AGTCAATTTA
17301 TCATATTGAT TAGAAAAGAA AAATATCATT ATTTCAATGT ATGATAAAAA
17351 GACATGATAT ATTTTAATTG CTGTGCTTCC TGAAAACTCT TAGAAAGTTA
17401 GAAATGGAAG GAAACTTAAA ATTTATTAAA CATCTATTAT GTTCCTGTTA
17451 ATTTGAGAAA CATGGAGTAT CCTGGTTTTT TTTTCAGCAT TAATTTGGAG
17501 ATTCTGAACA ATATGATTTA AAAGAAAACG AAATGAGCCA TATGTAAGTC
17551 AAAAGAAGGA GTAAAATTAT AATTTGCAGG TGATAACGAT TGTTTACCAG
17601 AAATTCAAG AAAATCATCC AAAAGGCTGT TGAAATAAAG AGTTCACTGC
17651 ATTGTCCATA CCAGATAAAT GCATAAAAAT CAATAGCTTT CTTATATTCT
17701 AGCGGCAGGT TTATTTACA ATTTCTTTAA AACCCAGTAA ATGTTTTATC
```

```
17751 CTGACAGGAA ATATACAACA TACATATATA CACACATACA CACGTGTGTG
17801 TATGAAGCTT TACTGAAGGA AATGAAAGAG GAACTGAGTG AAATAAAATA
17851 AGGCCATAAT CCTATTTGGA AGAACTAGGT ATTACAACAG TATCAATTTA
17901 CATCCAAATT TGTAAAGTCA ATACAACCCC AATCAAAACT CTAATGACCC
17951 ACTTGGGAAA TCGAGAAGTT GATTTTAAAC TTAATTTGGA ATAACTGAGT
18001 ACATGTTAAA AGAATACTAA TGAAGGGGAT TTTATCCTAC TTAAGTACAT
18051 GAAAATACAG ATATTTAGCC ATGGAAATCA GTAGTGTAGT ATTACAAATA
18101 ACTAAAATTA AAAAATTTAA CCTAGTGCTG ACATACATCA GTGCAACAAA
18151 ATTAAGAATT TTGAATCAAT AAGCAAATGA TGGATTATCA AATGTTATCA
18201 GCCTAAGTGG CTGTTTTGGA AAAATCAAGT TCTTTTCTTA CATCATACCA
18251 AAAAAAAAAG TTCCAAATAT GTTAAAGGGT TGAAAACAAA AATATAAAAC
18301 TGAAAATATT AGAAGTAAGT AGACTACCTT TAAAATCTTA GTTTGGCAAT
18351 GAAACTCTAA TCAAGTTAAA ATGCAGAAAA CACAGCAAAG GTATGGCTGC
18401 ACTGAGCTAA TAAATTACTG TATATGATCG AAAGACAAAG ACACATTAAA
18451 ATAAATGTTT ACAGTATATA TAACTAAAGA TTACTATCTG TAACATCCAT
18501 ATTATCTAAA TAAAAATGGA AAAATGTGCA AAGGACATGC ATGGTCAATT
18551 TACTAAAGAA ATAAAAATAA AAATAGTCAA TAAAAATACA GAGGAAGCTT
18601 TTCAAAATTT TCCCACACTT GTAATCTGGG AAATGCAAAG TAAAACAAGG
18651 TACTGTTATT TTTGCCCGTC AGACTTGCAC AAATTTAAAA GATTCATATT
18701 ATTTAGTGTC GGCAAGGATA TGAAGAAAAG GAAACTCATA AGCATTGGTG
18751 GGCACATAAA TTGATAACAG CCTTTTTTAG AAAGTAGTCT CTTAGTGTCA
18801 AACAAAATTT AAACCTTAAC AGTGTTTCTT TCAGGAATTC AGTCTACATC
18851 TGCTGACATA CATGTATAAG AATGTTCACC ACAGTATTGT TTCCAGCAAT
18901 AAAAACCAGA AAACAAATAA TGTTCAGGGA AATGGTTGAA TGAATTGCAC
18951 TGTGATAAAT TGGAAAAGTG TAAACAGCCA TTAAACTGAA TGCACTGTTC
19001 TGTTCTGAAA AATATGCACG AAAAATGAAA ATTGCAAAAA ATTAGGTACT
19051 ATTTCTAGAG TAGTTTTTAT AGAAGAGCA CCTGTGTGCA TGCATACAAG
19101 GGTAGTCAGA ATTGTTAACA GGTTATACTT CTGGGAAGTG GGATTGGGGC
19151 TTGAGAAATT AGAAGACACT AATTTGATAC ACTTACCCTT TTTTCAAAAA
19201 CATTATGTAA TTACCAAAAA CATGTAAAAA TCAGTTGTGT AGATTCAATC
19251 TATTTTAATT ACTTGGTTGG GTTTTTTTTT TTTTTGAAAT CACAGTTTAT
19301 CAGAGTTGAT ACTCAGTTTT TTAAATTATA CTGTATAACC CTCTGACTTC
19351 TCTATTTACC TTTATCCCCT ATCAACATAA AAAATAGGCC AGGCGTGGTG
19401 GCTCACGCCT ATAATCCCAG CACTGTGGGA GGCCAAGGCA GGTGGATCAC
19451 CTGAGGTTAG GAGGCTGAGG CAGGAGATAGTT GCTTGAACCC AGGAGGCGGA
19501 GGTTGCAGTG AGCAGCAATG CCTTGCACTC CAGCCTGGGC AACAAGAGTG
19551 AAACTCCATC TCAAATAAAT AAATAAATAA ATAAATAAAT AAAGTTCCTT
19601 TTGAAAAAAG GAGGATAGAA AAAACTATAA GCTGGGCATG ATAGATTTAA
19651 GTTCTCAGAC CTAATCCCAG CTCTTTGGGA GGCTGAGGCA AGAGGACTGC
19701 TTGAGCCCAG GAGTTCAAGG CCAGCCTGGG CAATAAAAGG AGACCCCGTC
19751 TCTACAAAAA AGAAGGAAAC AAAGGAAAAT GTATTGAAGT GTCAGGCAAA
19801 TTAGATAGAC TAGGATATAC AGGTAGGGTG TCAGACTTTA GAATCTTAGG
19851 CATTTTTCTT TTCCTGTAAC AATTTATAGT GACAGTGAAT GGTATTGTTT
19901 TATTTAGTTT TCATACAGTC TCGGGGTTTT AAAACTTTGA AATCAAGGAC
19951 ACGACGTCTC CAGTCTACCT CCGAGAGATT AGCTGAAACA CAGAATATAG
20001 CGCCATCATT CGTGAAGGTA ATTAGACCTT TTTATGATCC AAAAAGCAAA
20051 TATTTTCAAG TTGTTAGAGT GAGGAGCTTC AATATCTGAT TTCTTTTGTT
20101 GGCTGATAGA TATTCTTCCT TCTTTCCACT AATAATAAGG GATTAGTAAC
20151 CTGTGTAATC ATTATACCTC TAACTCTTCT GGGCACCAGA CTTGCCTCTC
20201 CACTTACTAG ATTTTTTTCC CACAAACCTA CACCTGTCGA GGTGTTCTCT
20251 GTATTAATGA GCAGCATCCA CCCAAGCTAA AAACCTGGCT ATCAACCTAC
20301 GTTTGTCCAT GTTGCCTTAC CTCCCACATC CATTAACCAC TAAAGTCCTG
20351 TTGATCCAAC CTCCTAAATA TTTCTTACAT CTGTTCCACT GCCATAGATA
20401 GGCTATAACT ATTTGTTGCC TAAATTACTG TAATGAATAC TTGTTTAGTC
20451 TCCTTGCCTC TAGTCTTGCT GCGTTCAGTC CAGCCTCCAG ACTGCCACCC
20501 ATCAATCTTT CTAAAATAAT GATCTAGTTA TATTACTCTG CTTTATTGCT
20551 TACCTCCACC TGATACACTG GGAATTTCAT CATTTGATCT CTACCTGCCA
20601 TGTTTCTCTT CTCACCATTC AATATGCCCC TCTGTTTCCC TGCTCCTCTC
20651 TTGGCATTGA AGTCTTATAT AAGATTGCTT ACAGTTCTTG AGCACTGAAG
20701 GCTATTGATT CATGCCTCCG TCAGATTGTT CATAGTGTTT ATTCCCTGTG
20751 TTTTAGATGT CCTATTCTCT GTAAGGCCTT TTCCATATTC CTGAGGTAGC
20801 ATTGATTTAC CACCATACAT AAATACTTCTA ACATATATC AAAATGATTT
20851 AAGAAACTTA GTTATTTATA TATCTTTTTC CAGTAGACTG AAAACTTTAA
20901 GATCAGTGGT TTATTTATCT TTACATCTTC AGAACTTATA TAAGGCCAAG
20951 TATATGAACG GTGCTTAGTA GACATTTAGT AAATTAATGA GATTTTTTCC
21001 TCTAGCAAAG ATAAAGGGAT AAGAACATTA AGCCAATCAA ACCCTAAAAT
21051 AATATGTGAC CTGTTTTCAG TGTAGTGTTC GTGCAGAGAA TAATGCCACT
21101 TTCTTTATAT TATTAATTGA TTGATGCAGG AATGGGATCT AGTGTTAGTT
21151 TCCTAGTTAT TGATTAATTC ATTGCTGAGT CTTAATCTGT TTCTTCACAT
21201 TGACAGTAAA AATTATACAG AATTTAGTG AATTTTTTG AGTGGTCACA
21251 ATATTGTTGG GAAGTATCAC TGTGTTGTTA ACCAGTACTG ATGTGTTGTT
```

```
21301 TGTGTATTCA GGGGTTTCTT TTGCGGGACA GAGGATCAGA TGTTGAGAGT
21351 TTGGACAAAC TCATGAAAAC CAAAAATATA CCTGAAGCTC ACCAAGATGC
21401 ATTTAAAACT GGTTTTGCGG AAGGTTTTCT GAAAGCTCAA GCACTCACAC
21451 AAAAAACCAA TGGTAAGTTG AATTGACACC ATCCGTGTTT GAGAAGAGTA
21501 ACTGAAAGGA AGTCATAGTC CTACATTTAA GTTTTAAGTA ACTTTTCTAA
21551 GACCATCTAT TGATTAAATT CCACTATATT TGTAACTTAA TCTATGTAGA
21601 AATGGCGATA CTGCTGATGG TTTCCCTTTC TCAAGAGAGA AAACAAATTG
21651 GAGAACAGGA AGTGTGAATG GCTTCATAAA GGTTTTTGTT TCTTTATTTT
21701 TTGTTTGTGT TTGTTTTTGA GACACGGTCT TGCTTCATTG CCTAAGCCAG
21751 AGTGCAGTGG TGCAATCATG GCTCATTGTA GCCTTAACTT TCTGGGCTCA
21801 AGTGATCCTC TCACCTCAGC CTCCTGAGTA GCTAGGATCA CAGGCATGTG
21851 CCACCACGCC CAGCTAATTT TTGTGGAGAT GGAATCTTGC CCTGTTGTCC
21901 AGGCTGGTCT TGAACTCCAG GGATCAAGTG ATCCTCCTGC CTTGACCTCT
21951 TAAAATGCTA GGATTACAGG CATGAGCCAC CATGCTTGGC CTTAAGTTTT
22001 TGATAATAGG GTACTTACAG GAAATCATAG CAGTTGTGAG AAAGAATGCC
22051 AGATTCCAAA ATTGGATGTG ATGAAATATG ATTATTAACA ATAACCTAAT
22101 ATTTGCATTT CATTGAGCTG TCATATTTCA TAAATGTGAT TTCATGTAAA
22151 GCTTTTTCTT TCTCTCCTAG ATTCCCTAAG GCGAACCCGT CTGATTCTCT
22201 TCGTTCTGCT GCTATTCGGC ATTTATGGAC TTCTAAAAAA CCCATTTTTA
22251 TCTGGTAAAA GCTTTTTTTA TTTGTCTAAC TTATTTCTTA TTCCTTTAAA
22301 TACATGATTC CTTTTAATGC CTAATCTAAC CCTTAAAGAA AGAACATATT
22351 AATGTTTACA GTACTAGAAT TAGGCTTTCA TTCCTAGTAG TGGTTAGTTT
22401 CCCAGATTTT TAGAAAATGA TACCTGTCCA ATTATAAATT TTAAAAATTA
22451 TCCTGGTCAA CAGGGTGAAA GGAAAATTAA TTAATTAATT TTAAAATTAT
22501 GTAGAAGAAT TTTATAATGG CAATACAAGC TGAAATAGTC TTCTATTTCA
22551 AAGATAAACA AATTCAGTTT ATTCATAAAA TCACATTAAA TGTTTCCCTT
22601 TTTTTTAGTT TGCTTATCTG AAATTAAGCA ATAGTGTCAG ACTTACGTGG
22651 TTCCAATTAC CTTTTCCACT ACTGTGCAGT TTTCACCCTG TGTTGCCTAT
22701 TCTCTTAAAT ATTAAGGATA TGTACAGATT CTTAAAAAAT ACTTTGTGGG
22751 CCAAAACTAT TGGTGTTCAT TCTAGAATTA CTATTTTAAA TTTGTTTTCC
22801 CAGCTTCTAT GTTCCTGATT TATTAAGCAT TTCTCCTTAA CCCCATATTT
22851 TGCCAGCTCA TTTTTCAGCC TATCTTAACA GTATTTTGGG CTTCTTCTGA
22901 GGAAATTAGA AATTGCTCAA TTTACTCATT TATAACTGCT CTAGTTTGGA
22951 AGTTTCTACC TGAGTGGGAA AGACTTAAGA AATCCTTGTA ATAGTTCTCC
23001 AAAATTGATC TCAAATATTT TACTCTCCCT ATCAGACTTT TTCTGTCTTG
23051 CTTGTCAGAC TTAATGTTGT CATAATTGAT AGGTCATTTG AGGGCAAGTA
23101 ATAACAGTTG TCAGAGGAAG AAGACTACAT GAAAAGTATA ATAATGTGTT
23151 AAGCCTCAAT TTTTTATTAA TGTGTGTCAA TGTTTTCTGC TAACTTTAAG
23201 GCAATGTGTT TCAAAGTGTA GACCTGTGAC CAATTAGAAT AATTGAAGTG
23251 TTTGTTAAAA ATGAAAATTC TCCTGGGCCC TGTGCTGTGG CCTGAGAATT
23301 AACATACTTC TCAAGTGAGT TTTATTCACA CCAAAGTTTG AGAAACTTTG
23351 ATTTAAGATT TCTATCATTA GATACTACAA TAAGAAGTAG AAAATAATTT
23401 TTGATTTTAT TAACTGAAAA GTACAAATAG GTCATTTTAT TTTATTTTTT
23451 TATTTTATTT CATTTATTTT TTTTGAGATG GAGTCTCGCT CTGTTGCCCA
23501 GGCTGGAGTG CAGTGGGGCA ATCTTGGCTC GCTGCAACCT CCTCCTCCTG
23551 GGGTTCAAGC AATTTCACTG CCTCAGCCTC CCGAGTAGCT GGGACTACAG
23601 GCTTGCGCCA CCATGCCCAG CTAATTTTTT GTGTTTTTAG TAGAGACGGC
23651 GTTTCACCGT TAGCCAAGAT GGTCTCGATC TCCTCACCTT GCGATCTGCC
23701 CGCCTCAGCC TCCCAAAGTG CTGGGATTAC AGGTGTGAGC CACCACGCCC
23751 AGTCTTTATT ATTTTTTATT TTTTCCAAGT TTATTAAGAA AGTAAGGAA
23801 TAAAAGAATG GCTACTCCAT AGGCAGAGCA GCCGAAANNN NNNNNNNNNN
23851 NNNNNNNNNN NNNNNNNNNN NNNNNNNNNN NNNNNNCAA CAACACTAAA
23901 CAACCACCTA CCAGACAAAC ACAATGAAAG CGCAAACTCC GACCCCCCAA
23951 CTCAATCAAC ACATACAAAA AAGATGCTCT ACCATCATAC CAAATCAACT
24001 AAGCACCTAG CAGGAAGGTA AAGCATCCA GTTCACCAGC CTCCCGGAGA
24051 GGCCTACATC CTGTAATCCC AGCACATTCG GAGGCGCACT CGGAAAGATC
24101 ACCGAACGTC AAAAATTCAA GACCAGCCTG ACCAACATGG AAAAACCCTG
24151 TCTCTGCTAA AAATACAAAA TTAGCCGGGT TGGTGGCGC ATGCCTGTAA
24201 TCCCAGCTAC TTGGGAGGCT GAGGCAGGAG AATCGCTTGA ACCTGGGAGG
24251 TTGAGGTTGC AGTGAGCCAA GATCGTGCCG CTGCACTCCA GCCTGGTAAC
24301 AGAGCAAGAC TCTGTCAAAA AGAAAAAAAA AGAAATCCAA AAGACCTAGT
24351 TTCTATTCCT CACTCTGATT TGATATGTGA AGTTAGGTCA CTTAGACATT
24401 TAATTTTTCT AGGCTTTGCT TCTTGCATC TAAAAAACAA GGTGATTGGA
24451 ATGTTATTAA TCTATCAAAT ATAAACATTT CTTTTCTTCC CTTTAGTCCG
24501 CTTCCGGACA ACAACAGGGC TTGATTCTGC AGTAGATCCT GTCCAGATGA
24551 AAAATGTCAC CTTTGAACAT GTTAAAGGGG TAAGTTAAGA AGATTGCCTT
24601 GCCTTCTTCA TACATCCTCT AATTGATACT CTATATGAGG TCGATATTTG
24651 ATTCTACAGT GTATTCCTAGA ATAGGTAAAA TTGTGTCCAA AAGTATTAGA
24701 AACATTAGTA TTTTGGGATA AATAATAATA GCCAAGGATC AAATCTTGCT
24751 TTATGGCAGG GGATAGTATA ATTTATGAAG GAGCAGCCTG GTGTAGTGGA
24801 GTGAATGTGG ACTTCAGAGT CAAGCTGACT AATGTTTGAA ATTCATTTTT
```

FIGURE 3, page 7 of 29

```
24851 ATACTTATTA GCTATGAGAC CTTGAAGAAA TTACTTTAGA TCCTGACAGA
24901 TAATGTATGT GCTTGACACA TAGTAGATAT TTAATAAATG GTCCTTCTTT
24951 ACCTGTACCT CTTACTGATC TTTGTAACTC CACTATCTAA AACATGTTAG
25001 ACAATGTATA TTTCTTGAAT GAATAGAATG GATAAATGCT AGTTTATAGT
25051 TGATTAATTT GTTAAATATT TAATAGTATC TATTAAGTGC TAGGCCCTAT
25101 TTTAGCTGCT GGGATAGAAT AAATAATCTC TGCATTCTTA GAGTTTAAAC
25151 TCTAAAAGCA GTAATTGGAC ACTGATATGT GATGTAAGAA AAAGTAGAGT
25201 ATGTTAAAAG AATAAAAGTG TATGGAGGAA AAAGTAGAGC AGGGTAAAGA
25251 GGATTGGGAG TTTTGAGAGA AGGCTTACAG TTTTAAATGG AGTGTTCAAG
25301 GTGTGATTGA TGGAGAAGGT GACATTTGAG ATAAAATCTG AAGGAGAAGA
25351 TGGAATAAAC TGCATTTATC TGAGAAAGGA ACGTTTCTGA CCAAAGGAAC
25401 AGTTTGAGCA AAGGCTCTCA AGTAATAGGG TGTCTGACTT GTTCATTTTT
25451 GAAAGTAGAA CTAATAGGAT TTCTTATTGG AACGTAGGGT GTAAGAGAAA
25501 AGAGGAGTCA AAAAGAGCCA CAAGATTTTT GGTCTCAGCA ATTAGAAGGA
25551 TAGAATTGAC ATTTACTGAG ATTTTTGTTT TTGTTTTTGA GACGGAGTTT
25601 CGCTATTGTT GCCCAAGCTG GCGTGCAATG GCGTGATCTC GGCTCAGTGC
25651 AACCTCCACC TCCCAGATTC AAGCGATTCT CCTGCCTCAG CCTCCAGAGT
25701 AGCTGGGATT ACAGGCACGA GCCACCACGC CCAGCTAATT TTTTGTGTTT
25751 TTAGTAGAAA CAGGGTTTTA CCATGTTAGC CAGGCTGGTC TTGAACTCCT
25801 GACCTCAGGT GATCCACGCA GATCAAAGTG CTGGGATTAC AGGCGTGAGC
25851 CACGGTGCCC GGCCTTTAGT GAGGTTTTAA AAGGCTGTGA GTGGAGCAGA
25901 TCTGGGGGAC AAAGGTTAGA AATTTAGTTT TAGGTATGTT AAGTGTGAGA
25951 GATACGAATG AAAGTGTTGA GTAACTTGGA TATACCACTT TGGAGGTATG
26001 GGAGAGGTCT GAGCTAGAAT TAAAAATAGG AGATTATATT TATATGTATG
26051 TTAAGTCCAC ATGTTTGGAT GAGATCACCC AGGGAGTGAG TGTAACCAGA
26101 AGAGAGATTT AAATACCGAG TTACAGAGCA CTTACTTGAA GGTTCACAAG
26151 ACAGAGAAGA GAAGCCAGGA ACCAAGATGA GAAGGAGCTG CCAGTGAGTT
26201 AGGTGACAAT GGTATCCTGG AAGAAAATAT TTCTATGATG AGGGGAGTGA
26251 TCAGCAATGT GAAATGCTAT TGATGGGCCA AGTGAGAACT AACCATTTGA
26301 TTTAGCAGTA GGTCATTGGT GTACCTGATA AAGAGCAATG TTAGTGGAGT
26351 AGCAGGGGTT AAATTCCAAT TGCAGTGGGT TTACAAGAGG TGGAAAGAAA
26401 TGAGATGGAA TAGAGGATTG CAAACAATTC TTGGATTTTG TCTGACAGAA
26451 GAGCACAGAT AATGTATCTC ATAATACAAA ATAAAGTTGG AATGTTGGTA
26501 AACTGTTAGG TGGGGGGGTT TGTGGGAAAT TGATAGAATC AAGGTCACCA
26551 GCAGAGAGAA TATGGCTGGG AGAGGAGGAA TGAGTGGTTA ATGGAGGAAG
26601 TAAATTGTGT AGCAATAGGA GAATGAATGG AAACAGGAAA TAAAACTGTT
26651 GTGCTCACTT GAAATTTTGG ATCATGAATT TATATTAAGA CAAGTCAAAA
26701 TGAGTGGTTT TTCTACTGAT TTTTTTTTTT ATTTTATCTT TTCCAAATGT
26751 GAATTCTGCA ACTTAGTAC CACACTGTGC TCTTCTCTGT GCTTTGCCAT
26801 TATATCTGCT CTATTACATT TGATTCTCA GAACTGTAGT GGCTGGGTAA
26851 TTATCTTTCA GGAGTGTTTT AGAAGAAATT CTTCCGCAGG AGGGATTTGA
26901 AGTACGTGAT CTGAGGACTC TTCCAACTCT GAAGAGATTG GTTATGTTAT
26951 TATTTCTGCT TTTCTTCTTT ACTTATTCGT GTCTCTGTTT ATACATAACC
27001 ATGTTTTTTC AGCCTTGACT ATTGGGGAAT AAGGCATTGG GAATCATTAT
27051 GATAGTTTTA CAACCAAGTA GTTCTTTCCT TTCCTTTCCA GTTTAAATGG
27101 CTATGAACCC TGTTGGAATT GTATAAAGGG AACAATTGAG GAAGAGGTTG
27151 GTGCAGTGAT TATTTGAAAA CTTCAGTCAT CAGCGTGGAG GGCCCTTCTC
27201 ATTGTGTTTG AGGTCTGCAT GCCTTTTCTA AATTGAGCCT GTATTAAGGC
27251 TGAGGTCAGA CACAGCATTG TTATTCTCTG TCTGTAATGT ACTTACATAC
27301 TTACTGAATA TATCACACTT CTTTTGGAAT GAGAGTTTTT TTTTTTTTTT
27351 TTTTTTTTTT TTGAGACAGG GTCTTGCTCT CTTGCCCAGG CTGGAGTGCA
27401 GTGGCATGAT CATGGCTCAC TGCAGCTTTG ACCTTCTGGG CTCAAGTGAT
27451 ACTCCTGCCT TAACCTCCCT TGTAGCTGAG ACCACAGGCA TGCACCACCA
27501 CACTTGGCTA ATTTTTTAAT TTAATTTTAT TATTCTTTCT AGACAGGGTC
27551 TGGCTCTATC ACCCAGACTG AAGTGCAGTA GTGTGATCTT AGCTCACAAC
27601 AACCTCCTCC TCCTGGGCTC CAGCCATCCT CCCGCCTCAG CCTCTCAGGT
27651 AGCTAGGACT ACAGGCGTGT GCCCCTATGC CTGGCTAATT TTTGTAGTTT
27701 TTTTTTATAG AGTCGGGATT TAGCTGCGTT GCCCAGGCTG TCTTGATCT
27751 CCTGAGCTCA AGTGATCCAC CCATCTTTGC CTCCCAAAGT GCTGGGATTA
27801 TAGGCATCAG CCACCAAGCC CAGCTGATTT ATCTTTCTTT TTCTTCTTCT
27851 TTTTTTTGGG GGGTGGGGGA GCGGTGTAGA GACAGAGTTT CACTTTGTTG
27901 TCCAGGCTGG TCTCAAACTC CTGAGCTCAG GCAGTCCTCC CATCTCAGCC
27951 TCACAAAGTG CTGGGGGTAA CAGGCATGAG CCACCACGCC TGTCCTGGAA
28001 TGTGGGGATT TCTGAGTACT AAACTAAAGC CATGCTGATA ACTAAGCATA
28051 GTGAAAGTAG ACATCACAAT TAAGGTAGAT CCTTACCAAG TTTTCCATGC
28101 TAAAATGAAT CAATTTTATA ATTGCTGTAA GACCTAAATT TATATAGAGC
28151 AAAGTAATTC AGTAGCATTT ACCAGAACAG GTTTGCCATT AGGTAGTTCC
28201 TGTGACAAAT GTTTACCAAA TCTCAAAGAG CTTGTATAGG AATGTCATTT
28251 CCTTGCCTAG AATTTCTGAA TATATGGGCA CACTTATATA TATAGCCTTA
28301 AAAATATTAA TAAGGGCTTT TAATAACTTG ATTCATTACC TTGATCCCAT
28351 TAACTATTTT CCTTGATAGA TCTTATGTTC CTCAAGTGGG GATTCTCTTG
```

FIGURE 3, page 8 of 29

```
28401 CCACAGAATT TGGAGAGAGA ATATAGTTTA TTTGAGTATT AAATTATGTT
28451 TAATCTCTTC TTTATTCCTA CAGCTTAAAA TTGGAATTAT ATCTATTATT
28501 TTGACCAAAT ATATTTTAGT CTTCTTTTAG TACATGGATA TTATCTTTCA
28551 AGTTCTCTTT TAATAAACCA GCCAAGTCTT TTTTTAACCA TAAATTTCAT
28601 TGAAGTTTAA CAAATTCACA CAACAGTGCA CAAATCCATA AATTTTCACA
28651 AACTGTCTGT GTTATAAGTA CCCAGCTCAA GAAATAGAAC CTTAGCAGAA
28701 GCCCAGAACC TCCTTGATGC CTCCTTCTGG TTACTAACCT AGGGACAATT
28751 TCCTGTCTAA TACCATACAT GAATTTTCCC TATTTTTGAA TTTTAGATAA
28801 ATGTAATCCA TATAGAATAT CCTCTTTTGT ATGAGGCTTC TTTTATTCAA
28851 CATGTTTGTG AGATCCATCT ATGTTACTTG GAGTTGAGGT TTATTTATCC
28901 TTTATTGCAT AGTATCCCAT TATAAGAATA CTACAACACG GTGCAATTAC
28951 ACTACTTTAG GGTGGACATT TATTTCTAGT TTTTGGTTCA AATACAGCTG
29001 GTGTGACTAC TTTTTATACA AGTCTCTTGG TGAACATATG TACACGCTTC
29051 TCCTGGACCT AGGAATGGAC AAAGCTTTGT TTTGTATTTT TTTAAATACT
29101 CTGAAAAGAA AATGCTATGT TTTTAACCAT TAACTTGATT AAAACATTAT
29151 TACATTTTTA ATTATTTAAT CAGAATAACT TTCAAAGATC ATTTCAAGTC
29201 TAACAAAAAA ACATAACTTT GTTCTTTAAT AAGTGTAATA TTTCCTGGAA
29251 ATATGCCTGG GAATTTTTCT TGAAATAATA AGCGAATCTT GACATTAATT
29301 GGACATTTTC AGAATGCCCT TTGGCGTGAA GCTATGTTTC ATGTTTTAGA
29351 ATGCTCCTCT CTAGGTACTT TCTTTTTAAC CCTGTCCAAT GTACTTGACT
29401 TTTGTTTTCT CACTGAGAAA ATGAAAGTTC AGAATGATTT TTTTGGGGAT
29451 AGTAAGGAGA CTTTGCATAA TTGGAAATAA TGGTCAGGGG AAAACCCTTT
29501 GTTTTATAAG GGGCCATTTT TGTATGCTTT TTTTACTGAA ACAGAGAAGG
29551 TCAGGTTAAT TCCATATCCA AATTAAATTT ATGATTTTCA AAAGGGAAGC
29601 CTTGATAATC TAACCAAACG TGTCCATTAT CTAAAGTTAT TTGGAAAATT
29651 GTGTCACTTT AGGTGGAGGA AGCTAAACAA GAATTACAGG AAGTTGTTGA
29701 ATTCTTGAAA AATCCACAAA AATTTACTAT TCTTGGAGGT AAACTTCCAA
29751 AAGGTAAGAT ATCTTTTCTT TATCATGATT TGATGGAAAA AACAAAACA
29801 AAGAAACAAA CAAAAAAAAC CTATATTACT TATTTAATTT TAACTGATTA
29851 AAGTTTAAGT CTTAATTGCT ATTTTACAAA ATAGATGTTC ATTCTGAACA
29901 TACAATTCCA TAGCCTTTTT TTTTTGGTAA CTGCAAGTTT TTATATACTT
29951 TCAAATTTAA AGTTACAAGA ATAGTACATA GAATGCTCCT CATACCCTTT
30001 ACCTAGACTC ACAAATTTTT AATATTTAGT TTCCTTTTTA GACCCAGGCT
30051 TGAGTGCAGT GATGCAATCA TGGCTCGCTG TAGCCACAAC CTCCCGAGTT
30101 CAGGCGGCCC TCCCAAGTAG CTGAGACCAC AGGTACACAC CACCATGCTG
30151 GCTAATTTTT GTATTTTTTG TAGAGATGAG GTTACTCCAT GTTGCCCAGG
30201 CTGCTCTTGA ACTCCTGGGC TCAAGCGATC CACTGACTTT GGCCTCCTAA
30251 AGTACTAGGA CTGCAGGCAT GAGCCAGCGC ACTCAACCTA ACTCCATTTT
30301 AAAAATCATT CACTTTGTCT CTTTATGTAT ATATAAATAT AAAAATTATT
30351 TGTAAATAAA TAAATTTTTA ACTATTTGAG AGTAAATTGT AAACAATCAC
30401 CCCAAGTGTG TATTTCCTAA GAATAAGGAT ATTCTTCTAT GTAACTCCAG
30451 AATAATATTA AAATTAGGAC ATTACTGGGT GTGGTGGCTC ACGCCTTTAA
30501 TCCCAGCAGT TTAGGAGGTG GAGGCGGGTG GATTACTTGA GATCAGGAGT
30551 TCGAGACCAG TCTGGTCTTG AACCAGGGGC CATTGGAGTT CCAACCAGCC
30601 TGGCCAACAT GGTGAAACCC TGTCTCTACT AAAAAAAGAA ATTAGCTGGG
30651 CTTGGTGGCA GGCGCCTGTA ATCCCAGCTA CTCAGGAGGC TGAGGCAGGA
30701 GAATCGTTTG AACCTAGGAG GCAGAGGTTG CAGTGAGCCG AGATTGTTCC
30751 CACTGCACTC CAGTCTGGGT GACAAAGCAA GATTCTGTCT CAAAAAAAAA
30801 AAAAAAAATA GGACATTTAA CATACATACA AAACCATTAT CAAATTTAGA
30851 GTCTATATTC AAATTTCAGC ATTTGCTCCA ATAGTATCCT TTGTAGTGTT
30901 GCCCTGATCC CTACCCACTT CCCCAGTTCA GGACCTAATC CAGGATCACA
30951 GGTAACATTT AGGCTTTTAT TGTTTTTTTT TTTTTTTTT TTCAAATGAA
31001 ACAATGAAAC AATTCCTTAG CCTTTTGTGA GGGAGTGGAG AGAAGAGGAT
31051 CTTTCATGAT TTTTACAGTT GCAAGAGTA CTTGCCTAAT TATTTATAGA
31101 ATGTTCTCAG TTTAGCTTTG TCTGATGTTT TCTCATGGTT AACATGACTT
31151 TTAATGACTT CACAGTATCC TTCTAATTTA TGGTTGTATC ACAATTTAAC
31201 CATTTATATT GAATTTTTAT ATGGTTTCCA GTTTTTTTGC TATTAAGAAT
31251 AGTGCTGTGT TTCATCTTAA TTCAAGGCTT TGCCTGCATG CTTAATTATT
31301 TCTTTAGAAT AAATTTCTAG AAATGGAATT GCTGAGTTAA AGGATGACAC
31351 TCCTTTTTAA TGCTTGTTTT TATGCTGCCA ACTATCTCCA CTGAAAATAC
31401 AGCAGTGTAT GAAATTATTT GCAGTAACCT TTGCTAATTT AGGGTACATT
31451 TATTAAATCA GTGCTTAATA ATGATAACTT TAGCTAATAT CACTGGCAAA
31501 AGCCTTATCA ACATCATGTA CTTCCTGATG CTCTAGAAAG GACCCAAGTG
31551 ATGGCTTATG TGGTGTCCAC GCAAAAGGA ATTAAAAAG AGCACAATCT
31601 CAATACAATC ATGAGAAAAC ACTGGAAAAG CCCATATCAG GAGACATTCC
31651 ACATACCACC TTTACATTTA TTTAAACATC ACAGAGTGAA TGTTTAAAAC
31701 CATAGAAGTA TTAATAGTTA CACTCTTCCT CTTTCTAATC ACAAGGAGTA
31751 TTTTAAATTT GTAGAAAATT TGAGTAGTAT AAATTTGTAG AAAAATCTTC
31801 AGATACCAAG ATGTAATCCA CAGAAATTAA TATGATTTAA ACCAGTTAAG
31851 TATAACTAAA ACATGACAAT ACTAGGATAG TCTTAAAGCT ATTTTGAGC
31901 TTGAGCTTTC TTTAAAATTT TTTTTATGTT AAAATGCAGC AAACATGTAT
```

```
31951 GTAAAGAAGT TTTGTTGCTT TTTAAATGTA ATATGTATAT TTATAAAAAC
32001 ATATAAATCA GGTAATTCTG TTTTTCTAAC GTGAAAATCT TTGGTGTTAT
32051 GAAAATTTGC AAACATGGAA AACCTTGAAA GAACAGTACA ATTAACATCC
32101 ATATCCTATC CACTTAGACT CAACAATTGT TAACATTCTG TCATATTTGC
32151 TTTCTGTGTT ATGTGTGTAT TTTTCCCCCT GAACATTTGA AAGAAAACTA
32201 TAAACATCAA CTACTTGACA TCTAAAGACT TTCTTGTACA TCACCTAAGA
32251 ATAAGGACAG TGTCCTAAAT AAACATAATA ACCTTATCCC ACCAAAGGAA
32301 ATTATGCCTA TTTCCTTAAT ATCATGTACT CTCAGTCTTG TTTAAATGTT
32351 TTCACCAGAT GTCTCTAGAA TTTTTTGTTC TTTATGAAAA AGCATCAAAT
32401 CAGGATTCAC TAATTACATT TGGTTGTTTA GTCTTTTAAT CTATTTTTAC
32451 ATGAATTTTA TCTTATTTAG TGATAAATGG GTTTATATTT TTTTGCCTCA
32501 AGATTCTCCC TGTCATGTCT CTTGTTGATA TGGAAACAAT ATTTATATAA
32551 TACAGGAACA TTAATTTTGG ACAAGATTCT GAAGTGAACC ATTAGCAGAG
32601 ACAAGTACGG TTTGCTGTGT TTCAAAATAT TGGTTATTGG TGTGACCTCA
32651 GCCTGAAAAT TATATAAATG AATAATTATT TATTTTATAG GTTCATATCG
32701 AGGGATTTTT TAAAAATACT TTGAATCATT CTCGTTTTCA TTTTCTTTTA
32751 GGAATTCTTT TAGTTGGACC CCCAGGGACT GGAAAGACAC TTCTTGCCCG
32801 AGCTGTGGCG GGAGAAGCTG ATGTTCCTTT TTATTATGCT TCTGGATCCG
32851 AATTTGATGA GATGTTTGTG GGTGTGGGAG CCAGCCGTAT CAGAAATCTT
32901 TTTAGTACGT TTTGGTGTAT CTTTGATGCA GTGCTAAATT TTGTTAAGGG
32951 AAGTGTGTAT CTTACCCTTT CTTTGCTAAT TACTTTTTTT CTTCCTTTTT
33001 TTAATTTCTA TTTTTTGGGG CCTCCAGCTT TGCATGCTAA TTAGTTTTGA
33051 TTGATAGTTA AAATAGCCAT TGTGGGACCT TGGTTTGGGT AACTTACTAT
33101 ATGAATTATC GGAAGAGCTA GTGGAAGTGC AAGATGAAGT TGGAGGCTAC
33151 CAAAAATCTC TTAGTGTTTT TTCATTTTAT TCATCAATTT TGTAGTATGG
33201 AATTAAGGAG TAATTAGCTT CAAACCTGAT TGTATATATT TGTATAGCTG
33251 GAAAGAATGA ATGAATGCCC AACTGTTTTG TTTTATATCA TTTCTTTGGT
33301 ATAGTTTTTT CCCCCCTGAA GATACTATTT TTAAGTCAGT AAAAAATGAC
33351 GTCCTTTTCT TTCAGTGAAT ATTTTTTGTT GGCTTTTGAC AGTTGTATAG
33401 GATTTTAATA TTTATCTCGT TTTGTTCAAA AGTGTTGACT TTCTTTCAGC
33451 TTATTTGAAT GTTTTTTGTT TTCTTAGGGG AAGCAAAGGC GAATGCTCCT
33501 TGTGTTATAT TTATTGATGA ATTAGATTCT GTTGGTGGGA AGAGAATTGA
33551 ATCTCCAATG CATCCATATT CAAGGCAGAC CATAAATCAA CTTCTTGCTG
33601 AAATGGATGG GTAATTGAGT CTTCTTTTTT CTTAGAATAT GGTGATGCCT
33651 CCCAGCATTT GATATACGTA GAATTGATCT TATGCAAATT ATTTCCATAA
33701 GGCATTTCAT ATCTAGAGAT ATGAAAAATG TGATGTGTAT AGGAAACAGA
33751 GTAGTCCCTC ATGCAAGAAC TCAAGACAAG CTTTTTCTCT CAGTATTGTA
33801 TTGTTTTCAT TACTAACTGG ATATTTGAAT ATCAACTCAT CTTATTTAAT
33851 TTATGGTATT TATATCCTTT TTCATTTATT GTTACACTTA TGACAGAAAA
33901 ACAATGATTT ATGCCGAGAC TAGTAGTCTA TTTGAAGAAA TACAGTTGTT
33951 TCTACATAAT TTATGACTAA CTTTGAGTGT TGTGGCAGAT TTAAAGCTTA
34001 CATCAATGTT CATAATATAA GAAGCAAGAG GTGATGTTGC TTTGAAAGAA
34051 GTATCTTAAA ACTCAATATA AGACATTTTG AAACCACATA GGAAGCCCAG
34101 GAGCAAATAA TTTGAATTGG TATACTTGAA AGTAATTTTT CAAAAATTAA
34151 CCAGGCACCT AAGCTTTTTA TATCAGGTTA TCTTTTCCTG CATAGACCAG
34201 ATAATTGTGA AGGTATGTAG TCAGAGATGA ATTGGTGGTT TATTATCAGT
34251 TTCTTTTCTT GGCTGTTATT TGATTAATGA AGCTGGGCAT GGTGGCTCAC
34301 GCCTGTAATG CCAGGACTTT TGGAAGCCAA GGTGGGAGGA TTGCTTGAGG
34351 CCAGGAGTTC AAAACCAGCC TGGTCAAGAT AGCAAGACCC TATCTCTACT
34401 AAAAATAAAA ACAGTCACCG GCACAGTAG CTCAAGCCTA TAATCCTAGC
34451 ACTTTGGGAG GCTGAGGCGG GTGTATTGCT TGAGGTCAGG AGTTCAAGAC
34501 CAACCTGGCC AACATGGTGA AACCCCGTCT TTACTAAAAA TATAAGAATT
34551 AGCTGGGTGT GGTGGCAGGC GCCTGTAATC CTGGCTACTC AGGAAGCTGA
34601 GACATGAGAA TTGCTTGAAC CTGGGAGATG GAGGTTGCAG TGAGCGCCAT
34651 TGAACTCCAA CCTGGGTGAC AGTGAGACTC CATCTCCAAA AAAAAAAAAA
34701 AATAGTGGCT TGTACCTAGA AATTGGGGAG AAAAGATTTA AAAATAAATA
34751 AAAAATAAAT TAGTCAGATA TGTTGGCATG CACCTGTCAT TCCAGCTACT
34801 TGAGAGGTTG AGGCAGAAGG TTCACTTCAA CCCAGGAGTT TGAGGCAGCA
34851 GTGAGCTATG ATCATACTGG TGCGCTTCAG CCTAGGCCAC AAAGCGAGTC
34901 CTAGTCTCAA AAAAAGAAAA CAAACCAGTT TTGTGTAGAG CATTTCTACA
34951 TGTGTGCTGT GCTTCAGTGT TAGTAAAAGA TACTATTTTT TTTCCAATAT
35001 AGTTTTAAAC CCAATGAAGG AGTTATCATA ATAGGAGCCA CAAACTTCCC
35051 AGAGGCATTA GATAAGTAAG TATTAAAAGA AGATTTTTGT GAAGTACTGT
35101 TACATGCTAC AAAATTGTGC TAAAAGAAGT CCGTTGCAAA AGATCACATC
35151 AACACTGTAT GATTCCATTT ATATGCAATA TCCAGAATAA GCAAATTCAC
35201 AGAGACAAAT TGGGTTAGCG GTTACCAGAG GTTAGGGAGA ATGGGGAATG
35251 GCTGTCATTG GATATGGGAT TTCTTTGTGG GGGATGGGAA TATTCTAAAA
35301 TTAGATTGTG GTGATGGTTG TACAATTGTG AATGTATTAA AAACCACTGA
35351 AGTATCCACT TTAAATTATG TGAATTACAT CTCAATAAAA CTTAAAATAT
35401 TTATTTGTTA TATGTCACAA AAGTTGTATG TAGAGAGGGT TTTTAAAATA
35451 AATTAACTGT AGTATTATAA CTAGGTTTAA AGTTACTATG AAAAAATTTT
```

FIGURE 3, page 10 of 29

```
35501 ACTGTAGAAG TTATTCGTAT TTTCATTTGA TCAGTAGTTT GTCACTGCCT
35551 AAGACTCTAG TCTAACATTC TGTACTTAGC AGTTGAGATG GATGTGTGGT
35601 TCTCATAATA GTTTGTTGTG GAATTATTTG TTCCTGGACT GAATTACCTG
35651 CATGCTTTTG TTTCTGAGGG GTAGGCTACC TAGGTACACA CGTGTATCTA
35701 AATGAACCTT TGTTCTGCTT TCTGGTTATT GACACTGTTA CTTGAGCCAT
35751 GTTTTAAAGG AACTATCTGA ATATTTATGT ACAAAACTCC ATCTGCGCTC
35801 TGGCTGCCAT TGGCTTCCCA GTCATGTCAT TAGGGTGTCA GTCCTGTTGA
35851 ATTTGAGCTT AAATAGTTTT AATTTATATT TTCCTTTTGC ATTCTTCCTG
35901 TAGTGCCTTA ATACGTCCTG GTCGTTTTGA CATGCAAGTT ACAGTTCCAA
35951 GGCCAGATGT AAAAGGTCGA ACAGAAATTT TGAAATGGTA TCTCAATAAA
36001 ATAAAGTTTG ATCAATGTAA GTATCAAAAC AAACATTTGT CATTTCTGTA
36051 AAGTGGTAAT ATACCACTCA CCCTGTTTGT GGTCCTTTCA TGATACATGT
36101 ATTAACATTA AAAGACCAGT TCATTTTTGT CTTTTTTTTT TCCATTAGTA
36151 TGTTCGTTTA AAAGTCCATT CCTTAGTGTA TATCCAGGAG ATTCTATTGT
36201 TTTGAACCCT GAGTCTAAAG AAAGGTTTTT TTAGAGTATT CAGACAGATA
36251 ATATTTGAGG ATACATACAT ATACATACAC ACACACACAT TTTTTAAGA
36301 TGAATGTAAA ATGCAAAATA ATTTAAAAAA GCTGCAGAAA CAGTAACTCA
36351 TGATATAGTC AGTGTGGGGC CAAAAGAGAA GAAAGCAAAT TATAAAACAA
36401 AACACATGGA AATTTATTAC TCACTTGAGT AATAAATGAA ATTATTAAAG
36451 CTGCAGTAGT TTCAGAGATA GCTGTATCAA TTCATTAAAC TATACATGTT
36501 TCCTATAAGG GCAGCTTTTA TGTCTAAAGT ATTTCCAGAT GAAATTCAGA
36551 GAAAAAGTGA CTAAACTATG GCTCAGAATA GCTAGCTATT TTCTTTTTTC
36601 CCTTGGAATG TGAGGTGTTT TTTTTTTTGG TTTTTTTTTG AGACAAGAGT
36651 TTTGCCCTTT TTGCCTAGGC TGGAGTGGAG TGGCACAATC TTGGCTTACT
36701 GCAACCTCCA CCTCCCGGGT TCAAGTGATT CTTCTGCCTC AGCCTTCTGA
36751 ATAGCTGGGA TTACAGGTGC ATGCCACCAT GCCCAGCTAA TTTTTGTATT
36801 TTTAGTAGAG ATGGGGTTTC ACCATGTTGG CCAGGATGGT CTCCAACTCC
36851 TGTCCTTAGG TGATCTGCCT GCCCCAGCCT CCCAAAGTGC TGGGATTACA
36901 GGCATGAGCC AACGCACCCA GTTGGAATGT GAGTTCTTTG TGAAGAGCTT
36951 TCTTTTACCT GTTTTAGACT TATTAGCGTT GTGTTCTCTT TTTACATTAG
37001 CCGTTGATCC AGAAATTATA GCTCGAGGTA CTGTTGGCTT TTCCGGAGCA
37051 GAGTTGGAGA ATCTTGTGAA CCAGGCTGCA TTAAAAGCAG CTGTTGATGG
37101 AAAAGAAATG GTTACCATGA AGGAGCTGGA GTTTTCCAAA GACAAAATTC
37151 TAATGGGTAG GTTTCCTTTC TTTTTTTTCT GTCTTTTACT TTTCATTGTG
37201 TTAGATAATT CATTTAGGGG CAAATACTCT ATTCAAACAG CTAAAGCCAT
37251 GGCTATGTTG AATCTAATCT TACTCTAAAA CTTCAGTGTC TGGGTTTTCA
37301 AGATTTGTAA TAAATGATTT TACAAAATTC CCAACTTAAC ATCAAACAAA
37351 TGCCATTAAA CTGTAACATT TTCTTGACAA TAATCTTGTC AGTGATACAG
37401 AACTGATTTT ATAGTGTACC ACATTTATTA GTTTTGTCTC TTTCTTAGAA
37451 AACCTTTTTT TCTGACTGGA AAGCTTTAAA AAGTGATGGG AACATGAAAA
37501 TATATACTTG ACAACACCAC AATTTGGCAT CTTACGAAAC AAATATATTC
37551 TAGTTGCTTA TGTAATTATA TAGTTAAACT GGTAGTGGGG AGATGAGGCA
37601 CGTATACATT TCCTCTTGTC AGACATTGCT GCGAAAAAGG ATACTTTATT
37651 CTGTGCTTAA TTTCGATTTT AAATCTTGGA TTGGCTTAAA ATCACATTAA
37701 TTATGATATT CTTGTTAAAC TGGAAGTTTA TTTTATAGAA ATAGAAATAA
37751 GTTTTCCCTT TTGAATTAAG ATGATAGTTT TGACAGTTTT GGTTTTCAGT
37801 TAAATTGTTA AAGTTTGTAT GTGTTAGGAA TGAATTCTGC CCATTTTGAA
37851 AAACTTTGTA GACTGGGCGT GGTGGCTCAC ACCTGTAATC CCAGCACTTT
37901 GGGAGGCCAA GGCAGGAGGA CTGCTTGAGC CCAGAATCGT TGGAGTTCAA
37951 GATCAGCTGG GCAACATAGC AAGACTCCAT CTCTACCAAA AATTTTAAAA
38001 ATTAGTTGGG TGGGGTGGCA TGCGACTGTG GTCCCATCTA CTTGGGAGTC
38051 CTAGGTGGGA GGATTACTTA AGTCCAAGAA GTTAAGCTA CAGTGAGCCA
38101 TGATCATGCC ACTGTATTCC AGCCTGGGTT ACAGACCCTG TTTAAAAAGA
38151 AACAAAATTA CTAAAAATTA CTAAAGCTAG GTGCAGTGGC ACATGCCTGT
38201 AATCCCAGCA CTTTGGGAAG CTGAGGTGGG TGGATTGCTT GAGGCTAAGA
38251 GTTCAAGGTT GGAGTGAGCT ATAATAAGAA TGACTTTAAG GAGAATGAGT
38301 TTTTTGTTTT ATAATATTAA TCCCATATCA GATACATTCA CCTCTCAGTA
38351 TCCACTGAAG GGGTGGGGAT TGGTTCCAGG ACCCATGTGG ATACCAAAAT
38401 TCAGGGATGC TCAAGTGTCT TTTATAAAAT GGTGTACTAT TTGCATATAC
38451 CTACATAATT CTCCTGTATA CTTCAAATCA TCTCTAGATT ACTAATACAA
38501 TATAAATGCT CTGTAAATAG TTGTTATAAT GTATTTTTTT CATTTGTATT
38551 ATTTTTTATT GTTCCTCTTC CCCATAGTTT TAATCCTTAT TTGGTTGAAT
38601 CTATGGATGC AGAATCTGCT GATAGGAAGG GTGGAGTGTA TTTGATTTGC
38651 AGACAAGAAT GTGTTTTGTT GATTAAATA TACCTTTCTA ATGGAGTATT
38701 TACTCAATTA AATTTATCTT AGGGCCTGAA AGAAGAAGTG TGGAAATTGA
38751 TAACAAAAAC AAAACCATCA CAGCATATCA TGAATCTGGT CATGCCATTA
38801 TTGCATATTA CACAAAAGAT GCAATGCCTA TCAACAAAGC TACAATCATG
38851 CCACGGGGGC CAACACTTGG ACATGTAAGT TTTTTGTAGT GTCTCGCCCT
38901 GTCACCCAGG CTGGAGTGCA ATGGCGCGAT CTCAGCTCAC TGCAACCTCT
38951 GCCTTCCGGA TTCAAACGAT TCTTTCACCT CAGCCTCCCA AGTAACTGGG
39001 ATTACAGGTG CCCACCACCA CGCCCAGCTA ATTTTTGTAA TTTTAGTAGA
```

FIGURE 3, page 11 of 29

```
39051 GATGGGGTTT CACCATGTTG GCCAGGCTGC TCTAGAACTC CTGACCTCAG
39101 GTGATCCACC TGCCTCAGTC TCCCAAAGTG CTGGGATTAC AGGCGTGAGC
39151 CACCATGCCC TGCCTAATTC TTAAATATCT AATTACTCCG CTGCCCCAAA
39201 AGGGAAAACA TTATGTTTTG TAGTAACTGA TTCAGTAGTT TCTCTAAGAT
39251 TTTTATCATT TAGTACAAGT TTATCAGATC TTTCAACATT GTAGACATTT
39301 AAAAAATTTC TATGCACCTG GGGGAGAAAC AGTCCTATTG CAGCATTATC
39351 CACCTATTGT TGTTGCTTTA TAAAGGATGT TTTTATTCTC TAATTGCTGG
39401 TTTTTCATCA GTCCCCTGAT GACCAGCTTT CAGCAACATG GTATAAAGTA
39451 CTTTAGTGAG AGCTAAATGA TAATTCTGGT TTGTATTTTT TTATTTTGCC
39501 CAGTCTTACG GTGCTGAAAT TCTGGTTTTT AATGTAACTA TATCAGAACT
39551 GTATCTGAAT TTTTTTTAAA TTTTTATTTT ATTTTATATT GATGGAGTCT
39601 CGCGATGTTG CCCAGGCTAC TCTCAAACTC CTGGGCTCAA GTGATCCTCA
39651 CACCTCAGCC TCCCAAAGTG CTGAGACTAC AGGTATGAGC CACTGCACCC
39701 AGCCTGTATC TGAATTTCTT TCATTACATT TTATTTTATT TTAATTTAAT
39751 TTGGTTTTAT TTTATTTATT GTATTTATT TTGAGATGG AGTTTCACTC
39801 TTGTTGCCCA GGCTAGAGTG CAATGGCATG ATCTCAGCTC ACTGCAACCT
39851 CTGTCTCCTG GCTTCAAGTG AGTCTTCTGC CTTAGCCTCC CAAGTAGTTG
39901 GGATTATAGC CATGCACCAC CATGCCTGCC TAATTTGTA TTTTAGTAG
39951 AGACAGGATT TCTCCATGTT GGTCAGGCTG GTCTCGAACT CCCAACCTCA
40001 GGTGATCCAC CCACCTCGCC TGCCAAAGTG CTGGGATTCA GGCGTGAGCC
40051 ACCGCACCCA GCCTCTTTCC TTATTTTTA TCTGATTAAT TTTAATTGT
40101 CTAGGTGTCC CTGTTACCTG AGAATGACAG ATGGAATGAA ACTAGAGCCC
40151 AGCTGCTTGC ACAAATGGAT GTTAGTATGG GAGGAAGAGT GGCAGAGGAG
40201 CTTATATTTG GAACCGACCA TATTACAACA GGTTAGCTTT AAAGAATGGC
40251 TTTAGTTCAA ATTATATGTG GTCTTAAAGA TATGTTTTAA AATGGTATGT
40301 TTTTATTTTA TTTTAGGTGC TTCCAGTGAT TTTGATAATG CCACTAAAAT
40351 AGCAAAGCGG ATGGTTACCA AATTTGGAAT GAGTGAAAAG GTAATAGATT
40401 TTTTAAATCC TTTTCATGTA TCAAATTATG TGTCAAGTGT TGATTTGAGA
40451 GCTGGTTCTG ATTATAAATT GGTAATATTC ACTTTTCTC TCACTCCAAA
40501 TGGATTTGAG GCTCTTTATT CTGAACATTG TTATTCTCTG AATAAAGAAA
40551 ATGGACCTTC TCTTAGCTGC TGAGAATGAG CTGCCCAGAT AGTAACTATT
40601 ACTTCACGAG TTAATTAAGT GATAAAGCAA GGTGAATTCC TTAGCTTTTC
40651 CATGTGGCAT GAAAGAGTCT ACTTTCTAAG TTTGGTTACT TTACTGTTTC
40701 CCTCTATTTC ATATTTTCAT CTTGTCATTG TTCCTTGAAG CACTACTATA
40751 CTCTGTGAAT TATGGATTTC TATATTTGAA GTAGCTGCCA AGGTTTTTCA
40801 AGAAAGTACT GAGAACCAGA CTTAAAATGA TTTTAGGCTG GGCACTGTGG
40851 CTCACATCTG TAATCCCAGC ACTTTGGGAG GCTGAGGAGA CTGTATTGCT
40901 TGAGCCCAGG AGTGAGTTCT GGACCAGCCT GGGCAACATG GCACAACCCC
40951 ATCTCTAAAA AAATACAAAA ATTAGCCAGG TATGGTGGTG TGTGCCTGTA
41001 ATCCCAGCTA CTTGGGAGTC TGAGGTGGGA GGATTCTCTG AACCCAGGAG
41051 GTCGAGGCTA CAGTGAGTCC ACTGCACTCT ACCTGGGTGA CAGAGCAAGA
41101 CCCTGTCTCC AAAAAAAAAA AAAAAGATTT TAAATGTTCT GTCTTGCTCA
41151 TACTTTTACT ATTTTGATAT TAGTGTTTTT TTGTTTCTTT GTTTTTGAGA
41201 CGGAGTCTTG CTCTGTTGCC CAGGCTGTAG TGCAGTGGCG TGATGTTGGC
41251 TCACTGCAGC TACCGCCTCC CGGGTTCAAG CGATTCTCCT GCCTCAGCCT
41301 CCCAAGTAGC TGGGATTACA GTCAACCTGC CACCATGCCT GGCTAAATGT
41351 TAGTCTTTAT ACTTTCAGAA GAATGTGGAA ATTTCTTTGC CCTCAAATGC
41401 AGTTTTTATT TTTATTTTTT TTGGAGACGG AGTCTCGCTC TGTCACCTAG
41451 GCTGGAGTGC AGTGGCGCAA TGTCAGCTTA CTGCAACCAC CGCCTCCTGG
41501 GTTCAAGCGA TTCTCCTGCC TCAGCCTCCT GAGTAGCTGT GATTACAGGC
41551 ACGTGCCGCT ATGCCCAGCT ATTTTTGTG TTTTTAGAAG AAATGGCGTT
41601 TCTCCGTGTT TCCAGGCTGG TCTCGAACTC CTAACCTCAG GTGATCCACC
41651 CGCCTCGGCC TCCCAAAATC CTAGGATTAC AGGTGTGAGC CACTGTGCCC
41701 GGCCTCAAAT GCAGTTTTCT ATTGTACTTC TTTCTTGTCC CCCGTATATT
41751 TGTTTCCTTA TATATAGGAT AGTACTTTCT CTTTCAAATT TGTTGGTGTT
41801 TGGGGGTTTT CTGTTCAATT ACTTTCTTCC TTTTGGTTTT AGCTTGGAGT
41851 TATGACCTAC AGTGATACAG GGAAACTAAG TCCAGAAACC CAATCTGCCA
41901 TCGAACAAGA AATAAGAATC CTTCTAAGGG TAATAATATT TTTTGTGCTT
41951 ATTTATTTTC TTAGGAACAA TGTGCTTAAA TAGTCAGGTT CTTAAAAAAT
42001 AACAGCTGAA GGCCCTCTGT TCACTAGAAA CATCATTTTA TAAAATAAAG
42051 ATAATAGTCA CCATGGTGTC TGGGGAAAAA ATTAAAAAAT AAAGATAATA
42101 GTTGCAGCAT TTCAGCAATG ATTTAAATGT TATTAAGGCA CCTCTCTGTT
42151 CATGAACCTG GACACGGGCT AAGAACAGTT CTATATTGCA TGGTTGTAAA
42201 AATTCAATTC TCAGGGTGAG GGACAAAATA ACTACATATT AGGTATTAGG
42251 TACAGTGTAC ACTATGTAGG TATGGATACA CTAAAATCCC AGACTTTACC
42301 ACTATACAAT TCATCCATGT AACCAAAACC ACTTGTACCC CATAAGCTGT
42351 TGAAATAAAA TCTATATATA AAATTTTATA TGTATATAAA ATTCAATTGT
42401 ACTTTAGCTG CAAAACTGTA AGAGGTAATA GAATGGGAAG AGTATTGTTT
42451 ATTGAGTCTT TGACATGTAT TCAACAAATA AATTTTTTTT TTTTTTTTA
42501 TGGAGTCTCA TTCTGCTGCC CAGGCTAGAG TGTAGTGGCA TGATCTCGGC
42551 TCACTGCAAC CTAAGAAATA AGTTTAGTAG GTGTTTATT GTTGGTTTTT
```

```
42601 TGTGGGTTTT GTCATTTTTT TTTTTAAGGG GATGGGTCTT GCTATATTGC
42651 CCAGGCTGGA CTTGAACTCC TGGGCTCAAG TCAACCTCCC AAGTAGCTGG
42701 GGCTACAGGC ACACACCACT ATGCCTAGCT CTATGATTTC AGTTTTTTGG
42751 TTTTGTTTTT TCTTTTTTTT TTTTTTTGA GACAGAGTTC TGCTCTTGTT
42801 GCCCAGGCTG GAGTGCAGTA GTGCTATCTC GGCTCATTGC AACTTCCGCC
42851 CTTCTGGGTT CAAAGTGATT CTCCTGCCTC AGCCTTCTGA GTAGCTGGGA
42901 TTACAGGCGC GTGCCACCAT GCCTGGCTAA TTTTTTGTAT TTTTAGTAGA
42951 GACAGGGTTT CACTATATTG GCCAGGCTGA TCTCAAACTC TGACCTCAGG
43001 CGATCCACCC ACCTCGGCCT CCCAAAGTGC TGGGATTACA GGCATGAGCC
43051 ACTGCGCCCG GCCCAATTTC AGTATTATGT ATGTTGAATT TGAGGCATCT
43101 TAGTTGGAAA TAGATGTGGG AACTTAGTGG AGAGATTGGT TATGTATTGC
43151 ATTTGAATGT TGAAGCTACC CATTCATGAA GGCAGGTCTT TTTTTTTTTT
43201 TTTTTTTTTT TTTTTTTTTT TTTTTTTTTT TTGAGACAGC ATCTTGCCCT
43251 GTCACCCAGG CTGGAGTGCA GTGCTGTGAT CTTGGCTCAT TGCAACCTCT
43301 GTCTCCCAAG CTCAAGTGAT CCTCCCACCT CAGCCTCCTG AGTAGCTGGG
43351 ACTATAAGCG CATGCTGCCA TGCCTAGCTA ATTTTGTTAT TTTTTGTAGA
43401 GAGCATTTCA CTATGTTACC CAGGCTGGTG TCGAACTCCT GGGCTCAAAC
43451 GATCCACCTG CCTTGGCCTC CCAAAGTGCT GGGATTACAG GTGTGAGCCA
43501 CCGCACCCAG CCAGGCAGGT TTTAAGGGTA AGACTGACCA GCCTGGGCAA
43551 CATGGCAAAA CCTCATCTCT ACAAAACATA GAAAAATTAG CTGGGCATGG
43601 TGGTTCATGC CTGTAGTCCC AGCTACTTGG GCTGAGGTGG GAGGATCACC
43651 TGAGCCCAGG GAGGTTGAGG CCGTAGTGAG TTGTGATTGC CTGACTTCAC
43701 TCCAGCCTAA GCAACAGTGA GACTGAAAAA AAAATAGAGA GAGAGAGAGT
43751 GACAGAGCTG AGTGCCAAAG TCTTTAGTGA GTAAGGACTA TGTTTGTCAG
43801 ATGGCACAAT GAAGACGGTT GGATAGCTCC ATAGTCAAAT GGCCTGGACT
43851 TCAACAGAAT AGGAAGAGTG CATTATATAA GAGGGTAGGT TAGTAATGGT
43901 CTGAAAGAGG TAATGGGAAC AATGAGCTCA GCTGTTTACT GTGAAGTAAC
43951 TAGGGTAAAC ATGAACAAAT AGCACTTGAG AGGGCTTAGG GAATGCATTC
44001 TCCACAGGAG GGACCATGGG TTTGATTATT TCAAGGAAGT AGAGGGAATG
44051 CTTTAGAGTA GTTAAGGATA CAGAAAGTTT GTATGATGGA AAGGTTTAGA
44101 GAGTGTTATA GAAGAGGTGG TCTCTGCCTT CTCAGGTGTT TATTCTCTTT
44151 TCCTTACTAT GTTATAATGC ACAAATTATC TCTACTGTAG AATCAAGATT
44201 CTACATGATT TTATAAATAT AAACAGATTT CATATTTTTT AGGGTACATA
44251 AAGTTTTTCT TTCTCTTCCC ATTGACTGGT TTTCGCATCC CTGCATTTGC
44301 TGCTGCTTAC GTATCTCCTT TTCTATTTCA GGACTCATAT GAACGAGCAA
44351 AACATATCTT GAAAACTCAT GCAAGGAGC ATAAGAATCT CGCAGAAGCT
44401 TTATTGACCT ATGAGACTTT GGATGCCAAA GAGATTCAAA TTGTTCTTGA
44451 GGGGAAAAAG TTGGAAGTGA GATGATAACT CTCTTGATAT GGATGCTTGC
44501 TGGTTTTATT GCAAGAATAT AAGTAGCATT GCAGTAGTCT ACTTTTACAA
44551 CGCTTTCCCC TCATTCTTGA TGTGGTGTAA TTGAAGGGTG TGAAATGCTT
44601 TGTCAATCAT TTGTCACATT TATCCAGTTT GGGTTATTCT CATTATGACA
44651 CCTATTGCAA ATTAGCATCC CATGGCAAAT ATATTTTGAA AAAATAAAGA
44701 ACTATCAGGA TTGAAAACAG CTCTTTTGAG GAATGTCAAT TAGTTATTAA
44751 GTTGAAAGTA ATTAATGATT TTATGTTTGG TTACTCTACT AGATTTGATA
44801 AAAATTGTGC CTTTAGCCTT CTATATACAT CAGTGGAAAC TTAAGATGCA
44851 GTAATTATGT TCCAGATTGA CCATGAATAA AATATTTTTT AATCTAAATG
44901 TAGAGAAGTT GGGATTAAAA GCAGTCTCGG AAACACAGAG CCAGGAATAT
44951 AGCCTTTTGG CATGGTGCCA TGGCTCACAT CTGTAATCCC AGCACTTTTG
45001 GAGGCTGAGG CGGGTGGATT GCTTGAGGCC AGGAGTTCGA GACCAGCCTG
45051 GCCAACGTGG TGAAACGCTG TCTCTACTAA AATACAAAAA AATAGGGCTG
45101 GGCGCGGTTG CTCACGCCTG TAATCCCAGC ACTTTTCAGA GGCCAAGGCG
45151 GGCAAATCAC CTGAGGTCAA GAGTTTGAGA CCAGCCTGGC CAACATGGTG
45201 AAACCCCATC TCTACTAAAC ATGCAAAAAT TACCTGGGCA TGGTGGCAGG
45251 TGCTTATAAT CCCAGCTACT CTGGGGGCCA AGGCAGGAGA ATTGCTTGAG
45301 CCTGGGAGAT GGAGGTTGCA GTGAGCCGAG ATCATGCCAC TGCACTCCAG
45351 CCTGGGCAAC AGAGCAAGAC TCTGCCTCAA AAAAAAATTA AAATAAATTT
45401 AAATACAAAA AAAAATAGCC AGGTGTGGGG TGCATGCCTG GAATCCCAGC
45451 TACTTGAGAG GCTGAGGCAC GAGAATTGCT TGAACCCAGG AGGTGGAGGT
45501 TGCAGTGAGC CAAGATCACA GAAGCCACTG CACTCCAGCC TGGGTGACAG
45551 AGTGAGACTC TGTCTCAAAA AAAAATTAAA TAAATTATTA TAACCTTTCA
45601 GAAATGCTGT GTGCATTTTC ATGTTCTTTT TTTTAGCATT ACTGTCACTC
45651 TCCCTAATGA AATGTACTTC AGAGAAGCAG TATTTTGTTA AATAAATACA
45701 TAACCTCATT CTGAATAATG TCCCTCATTT TGACTATAAC TGTGCTTGGT
45751 TTCAAAAGCA AAATTAAACA AAAATCTCAG TCCCCTCCGA AGTGAACTTT
45801 GTGTTACCCT GCGTCAGAAA TGCCAAGTTG TGTTTACTTT TCATTCAGAT
45851 TTTGTGAATA TGAACATGCT GTTATAGGAT CTACAGATGA ATATTTAACT
45901 CAATAGAAAA ATTATTTTAG AACACATTGT ATTGGTATTA CAACCAGATT
45951 ATATTCTTGA CGTTGACTTC ATTAAAATTA TCTACAATTT CCTAATAATT
46001 TAAGCTGTAT ATGGTCTTCA TTGAAAAAAG ATAGATATTG TTACAGGAAG
46051 CTTGTTACAT TATATTCTTG ACCTTTTGGT TGATAATCTT AAATCTTAAT
46101 GTAATTTCAA ACTGGCAGAA ATGTTGCCAG CATAATACAT GGATGTCTCA
```

FIGURE 3, page 13 of 29

```
46151 TATACCCTGC ATCCAGATTT ACCAGTTGTT ATCATTCTGC CCGTTTTTTA
46201 TTGCCCCAAA CCTGTTCTGT CTCCCTCTCT GTATGTACAT ACATACACGT
46251 ATAAAATATT GATGAAGTCT TATCTGTCTT AAATTTTTTT ACATATTTGT
46301 TGAGGTATAA TTTACATATG ATAAAATTCA TTTTAAATGT AGAGTTGAAA
46351 GATGTTGTGT GTGTAATCAT CACCACAATT AGATTTTAGA ACATTTCCAT
46401 CACCCAAAAC ATTGTCATGC AAGTGTTTGG ATTAATTTTT TAAGAAACTT
46451 ATGAACTATT TTCAAAGTGA CTATAATTTT ATGTTCTAAC TAGCAATGTA
46501 GGAGGGTTAT AGTTCTCCA CATCTTTTGC AGTGCTTATA GTCTGCCTTT
46551 ATAATTATGG CCATTCTAGT GGACCACTCA TATCCAAATT AATCTCATCC
46601 AAGTTAGATC ATTTCTCTAG TGACATAAGA TGCTGAGCAT CTTCCGGTGC
46651 TTATTGGCCA TTTGTATATC TTCTTTGGAG AAGTGTCTAT TCAGATCTTT
46701 TACTTCTTTT AATTGGGT
```

FEATURES:

| | |
|---|---|
| Start: | 2140 |
| Exon: | 2140-2172 |
| Intron: | 2173-7309 |
| Exon: | 7310-7444 |
| Intron: | 7445-10762 |
| Exon: | 10763-10925 |
| Intron: | 10926-19907 |
| Exon: | 19908-20017 |
| Intron: | 20018-21311 |
| Exon: | 21312-21462 |
| Intron: | 21463-22170 |
| Exon: | 22171-22254 |
| Intron: | 22255-24496 |
| Exon: | 24497-24579 |
| Intron: | 24580-29662 |
| Exon: | 29663-29753 |
| Intron: | 29754-32751 |
| Exon: | 32752-32904 |
| Intron: | 32905-33477 |
| Exon: | 33478-33610 |
| Intron: | 33611-35002 |
| Exon: | 35003-35065 |
| Intron: | 35066-35903 |
| Exon: | 35904-36016 |
| Intron: | 36017-37000 |
| Exon: | 37001-37156 |
| Intron: | 37157-38722 |
| Exon: | 38723-38874 |
| Intron: | 38875-40104 |
| Exon: | 40105-40231 |
| Intron: | 40232-40316 |
| Exon: | 40317-40390 |
| Intron: | 40391-41842 |
| Exon: | 41843-41929 |
| Intron: | 41930-44331 |
| Exon: | 44332-44472 |
| Stop: | 44473 |

SNPs:

| DNA Position | Major | Minor | Domain | Protein Position | Major | Minor |
|---|---|---|---|---|---|---|
| 343 | C | A G | Beyond ORF(5') | | | |
| 950 | T | G | Beyond ORF(5') | | | |
| 975 | T | C | Beyond ORF(5') | | | |
| 2196 | T | A | Intron | | | |
| 2207 | C | T | Intron | | | |
| 3928 | C | T | Intron | | | |
| 6093 | A | G | Intron | | | |
| 6179 | G | A | Intron | | | |
| 6995 | G | A | Intron | | | |
| 7285 | A | G | Intron | | | |
| 7315 | G | A | Exon | 13 | T | T |
| 7734 | T | C | Intron | | | |
| 8988 | G | T | Intron | | | |

FIGURE 3, page 14 of 29

| | | | |
|---|---|---|---|
| 10290 | G | A | Intron |
| 10315 | C | A | Intron |
| 10495 | - | A | Intron |
| 10566 | T | G | Intron |
| 10608 | G | A | Intron |
| 11648 | G | T | Intron |
| 11665 | G | A | Intron |
| 14162 | G | A | Intron |
| 14226 | A | C | Intron |
| 14250 | T | - | Intron |
| 14483 | G | A | Intron |
| 15966 | A | G | Intron |
| 16162 | A | G | Intron |
| 16565 | T | A | Intron |
| 16815 | T | C | Intron |
| 17110 | G | A | Intron |
| 18464 | G | A | Intron |
| 18500 | T | C | Intron |
| 18864 | G | A | Intron |
| 18975 | C | T | Intron |
| 19780 | T | C | Intron |
| 20201 | C | T | Intron |
| 21014 | A | G | Intron |
| 21022 | A | T | Intron |
| 21712 | T | C | Intron |
| 22809 | A | G | Intron |
| 23025 | C | G | Intron |
| 23029 | C | - | Intron |
| 23208 | G | A | Intron |
| 25083 | T | - | Intron |
| 25186 | A | C | Intron |
| 25741 | T | G | Intron |
| 25764 | G | A | Intron |
| 25831 | C | T | Intron |
| 25927 | G | C | Intron |
| 27184 | T | C | Intron |
| 27235 | G | A | Intron |
| 27313 | T | C | Intron |
| 27362 | - | T | Intron |
| 28123 | T | G | Intron |
| 28318 | T | A | Intron |
| 28598 | - | C | Intron |
| 28630 | A | C | Intron |
| 29472 | T | G | Intron |
| 30809 | - | A T | Intron |
| 31106 | C | G | Intron |
| 32031 | G | A | Intron |
| 32206 | A | G | Intron |
| 32711 | T | A | Intron |
| 33310 | T | C | Intron |
| 34224 | G | C | Intron |
| 34703 | - | A T | Intron |
| 35356 | C | A | Intron |
| 35440 | T | - | Intron |
| 36325 | A | T | Intron |
| 38525 | T | C | Intron |
| 39410 | A | G | Intron |
| 39603 | C | T | Intron |
| 40056 | - | G A | Intron |
| 40283 | T | C | Intron |
| 40857 | T | C | Intron |
| 41705 | G | A T | Intron |
| 44325 | A | G | Intron |
| 45067 | G | A | Beyond ORF(3') |
| 45576 | A | G T | Beyond ORF(3') |
| 46264 | G | A | Beyond ORF(3') |

Context:

DNA

Position

343
CACGCCAGTAATCCCAGCACTTTGGGAGGCCGAGGCGGGAGGAATACGAGGTCAGGGAAT
CGAGACCATCCTGGCTAACACGGTGAAACCCCGTCTCTACTAAAGAAACCCCGTCTCTAC
TAAAAATACAAAAAATCAGCCGGGCGTGGTGACGGGCGCTTGTAGTCCCAGCTCGTCGGG
AGGCCGAGGCAGGGGAATGGCGTGAACCCGGGGGGCGGAGCTTGCAGTGAGTCGAGATTG
CGCCACTGCACTCCAGCCTGGGAAACAGAGCAAGACTCCGCCTCAAAAAAAAATAAAAAA
[C,A,G]
AAACCTAACTCAAGCCAGGGTGAGACTACGAATCACGGCTTTGGCTTTAAGTGCCTGTTG
TACTAAGACCGATGTAATCACCTCGGTCAAGTCCCTTTGCCTTTGGCCTCAGTTTCCTCA
TTTGCTAACGCTGGGCAGGGAGAAGAGAGTCAAACTTTGCTGTTCTCACTGTGCATCTGA
GATATGGAGGGAAGGGCGGAACAGAGGCGAGACACCCGACCCGACCGCTGATGTCGCCCC
AAAAAGAAGTCAGCTCGCAGGGCTCTGGAGGCTTCAGCAAGCCAGGCCACCCAGACTCCT

950
AGCAACCCCGGGGCCTGCCCAAGCCGGTGGGGCAGGAAGGAGGGCCGAAGGGCCTAACCC
CTTCCTTGCTACTCGTTGACTTCCTACCTTTACTGCATACAATTTGCCGCCTTTCTGCCC
CAGATACACTTTCCCGAAGGCGCCCCGGCTAATGGGCTTCACTATGCTGAATTCCTCAAT
GGAGGGCGGTTTTGGCACTGCGATCCTATTCACGCCCTCCTCAGTCGCCGCGCCTCCTCC
AGGCTCCTTCTTGCTTCCCGCGGTGGGATCCATCGCTGGACAGCCTACAGCGGCCCCGCG
[T,G]
ACACTGCCCCTCCGCGAGCAGCCATTCCCGCCAACTGGGTTCAAAGTGAGGCTCCGCCCA
CGCCGCGCGCGGCCGTGACGTCACCCCGCCGCCGCGCCCCGCCCTCGTCACCTCCCCTAC
GCAGACGCGGACGGAGGGGGGCGTCGGGAAAGCCCCGACTTCGCAGCCTTACACTCTTCG
TGGGCGGCGACCGCGGCCCCACTGACATCATTCCTCATGAGGGAGGAGGCACAAACAGTT
CTGGGCCGACCAGAAAAAGGACGACTGGGACTTGACTCTGAATCGCAGGATTTGAAGAGA

975
GGTGGGGCAGGAAGGAGGGCCGAAGGGCCTAACCCCTTCCTTGCTACTCGTTGACTTCCT
ACCTTTACTGCATACAATTTGCCGCCTTTCTGCCCCAGATACACTTTCCCGAAGGCGCCC
CGGCTAATGGGCTTCACTATGCTGAATTCCTCAATGGAGGGCGGTTTTGGCACTGCGATC
CTATTCACGCCCTCCTCAGTCGCCGCGCCTCCTCCAGGCTCCTTCTTGCTTCCCGCGGTG
GGATCCATCGCTGGACAGCCTACAGCGGCCCCGCGTACACTGCCCCTCCGCGAGCAGCCA
[T,C]
TCCCGCCAACTGGGTTCAAAGTGAGGCTCCGCCCACGCCGCGCGCGGCCGTGACGTCACC
CCGCCGCCGCGCCCCGCCCTCGTCACCTCCCCTACGCAGACGCGGACGGAGGGGGGCGTC
GGGAAAGCCCCGACTTCGCAGCCTTACACTCTTCGTGGGCGGCGACCGCGGCCCCACTGA
CATCATTCCTCATGAGGGAGGAGGCACAAACAGTTCTGGGCCGACCAGAAAAAGGACGAC
TGGGACTTGACTCTGAATCGCAGGATTTGAAGAGATTTCTCCTGGCTTCCCAACGAGGCT

2196
CTTGGCCTTGTGGGCGCTCACTTGCCCCGGAAGTACTGTTGAGTTAGCGCCTCGCCTTCC
GGGGCGGATTGTCTGTCGTTGCAGTAGCTGTAGGAAGGGGAGGCCATTTTCCGTTTCTGG
GAGGAGTGAGGGGCAACGGGTCGGAGAAAAAGGAAAAAAGAAGGGCTCAGCGCCTCCCCG
CCGGGCCGTGGACAGAGGGGCACAGTTTCGGCAGGCGGGTGAGGTCGCTGAGGGCCCGCC
GGAGATGTTTTCCTTGTCGAGCACGGTGCAACCCCAGGTAAGCCAGGCATTCAGCCCATT
[T,A]
TTTTTCCTCCCGCCCTGCCCGTGGCTGTTTGCAAATTGCGCTCGTGGAAGCGATTTCTCA
GAAGGGACTCTAGAAATGAAGTGATGTACTCAATGCGAATCCCAGGATTGAGGAGTGGAT
CAGGGGACGACGCTGAGAGTGGGCCGGAGACTTCAGTGCTGACGATGAAGCTGTTGAGGG
CAGAGGCGGGATGTGAGCTCAGTGATAGAGAGAGACCCTGGCTTATCGAACTGATTGCGT
GGAATTTCTGCTAGAGAATCCGTCCGGCATTGTTCAGTGTCCGGCGTTCTGGGGTGGGAA

2207
GGGCGCTCACTTGCCCCGGAAGTACTGTTGAGTTAGCGCCTCGCCTTCCGGGGCGGATTG
TCTGTCGTTGCAGTAGCTGTAGGAAGGGGAGGCCATTTTCCGTTTCTGGGAGGAGTGAGG
GGCAACGGGTCGGAGAAAAAGGAAAAAAGAAGGGCTCAGCGCCTCCCCGCCGGGCCGTGG
ACAGAGGGGCACAGTTTCGGCAGGCGGGTGAGGTCGCTGAGGGCCCGCCGGAGATGTTTT
CCTTGTCGAGCACGGTGCAACCCCAGGTAAGCCAGGCATTCAGCCCATTTTTTTTTCCTCC
[C,T]
GCCCTGCCCGTGGCTGTTTGCAAATTGCGCTCGTGGAAGCGATTTCTCAGAAGGGACTCT
AGAAATGAAGTGATGTACTCAATGCGAATCCCAGGATTGAGGAGTGGATCAGGGGACGAC
GCTGAGAGTGGGCCGGAGACTTCAGTGCTGACGATGAAGCTGTTGAGGGCAGAGGCGGGA
TGTGAGCTCAGTGATAGAGAGAGACCCTGGCTTATCGAACTGATTGCGTGGAATTTCTGC
TAGAGAATCCGTCCGGCATTGTTCAGTGTCCGGCGTTCTGGGGTGGGAAAATGTCTGTAC

3928
GGGAGAGGTGTTTCTGGGTTTGATCAGATGAATGCATTGAAGGTGCTATTTACCAAGATG
ACAGTGTCTGGAGAAGTCCTAGTAATTGTTTGAAAAAGAAGTCTGACATGGCCTATTGAA
TATGGTATTGAAGTTTTTGAAACTCAACTCTTTGCCTTAGTTCACATCAAGAGGCCTGAT
TTTAGGAGAATTTACCATCAACTGAATGGACAGTTAGTAGTATGTGATGTTGGTAGAGAT
GATAAAGGGATTTTTATGTACCCTAGGCAGTCTTAACAGGGCTCAAATATAGTGAGGACT
[C,T]
TCAGGCATTTCTTGCTTTGAAGGATGGTAACACATTTGGAATTCCTTGTTGCTTAATTGG
TTGAATACACTTGAAATTAAATGGTAAAAAGGAAGACACAGAAAATGAACTTTTTCATTG
AGAAGAGCTCAATTCTAAATCCTTTTGTGAAAGAAAAGAGATATAACTAATTCAAATAAA

FIGURE 3, page 16 of 29

```
              AGAGATATAACTAATTCAAATAAATCTTTTCAAAGAGGTAGAAAATATGTATCTTGAAAT
              GATTTGATTATTTTTAAAGTTTCAAAAGAAGTTACTGTTTATTTTTTTTTCTTTTTACTG

6093    TGGCTGGCTTCCTTACTACAACCTGTTTTATCATCACGGTCTTTATGACCTGTATCTTGT
              GCCCACACCCTATCTCATCCTGTAACTTAGAATGCCTAACCTCCTGGGAATGCAACCCAG
              TAGGTCTCAGCCTCATTTACCCTCATTTTGCCCCTACTCCAGATGGAGTCACTCTGGTTC
              AAAAGTCTCTGACAGAACTGTAACAAGAAGTATAATTGTTACTCATTATTATAGCTGTTT
              GAGGATTAAATGGGATGATAGAAGTAAAGCCTGTAGTACTAAACCTGGTATATAATAAGA
              [A,G]
              CCCATTTAATGTATTCATTTACTCAACAAATATTTATTAAGTAAATTTTTTTTTTCTTG
              AGACAGGGTCTTGCCATGTCATTCAGGCTGGAGTGTGGTGGCATGATAGCTCACTGCAGC
              TTCAACTTCCTGGGCTCAAGTGTTTTTTTTGTTTTCATTTTTATTTATTTATTTATTTTG
              AGATGGAGTTTTGCTCTTGTCACCCAGGCTGGAATGCAATGGCATGATCTTGGCTCACTG
              CAACCTCCGCCTCCCAGGTTCGAGTGATTCTCCTGCCTCTGCCTCCCAAGTATCTGGGAT

6179    TTAGAATGCCTAACCTCCTGGGAATGCAACCCAGTAGGTCTCAGCCTCATTTACCCTCAT
              TTTGCCCCTACTCCAGATGGAGTCACTCTGGTTCAAAAGTCTCTGACAGAACTGTAACAA
              GAAGTATAATTGTTACTCATTATTATAGCTGTTTGAGGATTAAATGGGATGATAGAAGTA
              AAGCCTGTAGTACTAAACCTGGTATATAATAAGAACCCATTTAATGTATTCATTTACTCA
              ACAAATATTTATTAAGTAAATTTTTTTTTTCTTGAGACAGGGTCTTGCCATGTCATTCA
              [G,A]
              GCTGGAGTGTGGTGGCATGATAGCTCACTGCAGCTTCAACTTCCTGGGCTCAAGTGTTTT
              TTTTGTTTTCATTTTTATTTATTTATTTATTTTGAGATGGAGTTTTGCTCTTGTCACCCA
              GGCTGGAATGCAATGGCATGATCTTGGCTCACTGCAACCTCCGCCTCCCAGGTTCGAGTG
              ATTCTCCTGCCTCTGCCTCCCAAGTATCTGGGATTACAGGCGCCCAACACCATTCCTGGC
              CAATTTTTTTGTATTTTTAGTGGCGATGGGATTTCACCACGTTGGCCAGGCTGGTCTCGA

6995    CACTGCAACTTCCGCCTCCTGAGATCAAGCAATTCTTCTACCACAGCCTCCCAAGTAGCT
              GAGACTACAGGCGCACACCATCACACCCATCTAATTGTTGTATTTTTGGTAGAGATGGG
              GTTTCACTGTGTTGGTCAGGCTGGTCTTGAACTCCTGACCTCAAGTGATCCACCCACCTC
              GGTCTCCCAAAGTGCTGGGGTTACAGGCGTGAGCCACTGCACTCGACCAGTGGTATCATT
              TGTTTTGCCGCTCCCCTAATGCTGGATGTTTCCAGCTTTCTACTATTTTTAAATGTTTC
              [G,A]
              ATGAGAGTTGTTCTCTATGCATGTGCAAGTACTTGTCAGATTATTTCCTTATAATAAATT
              CCTAGAAGGTGGATTGCTACAAACAAGAAATGTATGTATTTTTGATACTTTTGATTTACA
              TATTCAGAATAATATCCTGAAAGAACATACCAGTTTTCGTCTCACCAGCAGTAAATCTGA
              GTACTTACAGTTTTTAGTATACAGAGTTGATATATAATGTACCTTTAACTCTTAACAAAT
              CCTGACAAAAAAGGAGATTGTTCTGTTTATTTAAAAAAAAAACTACTTAATTTTTAACTT

7285    TAAATGTTTCAATGAGAGTTGTTCTCTATGCATGTGCAAGTACTTGTCAGATTATTTCCT
              TATAATAAATTCCTAGAAGGTGGATTGCTACAAACAAGAAATGTATGTATTTTTGATACT
              TTTGATTTACATATTCAGAATAATATCCTGAAAGAACATACCAGTTTTCGTCTCACCAGC
              AGTAAATCTGAGTACTTACAGTTTTTAGTATACAGAGTTGATATATAATGTACCTTTAAC
              TCTTAACAAATCCTGACAAAAAAGGAGATTGTTCTGTTTATTTAAAAAAAAAACTACTTA
              [A,G]
              TTTTTAACTTTTATCTTTTTCTAGGTTACAGTTCCTCTGAGTCATCTCATCAATGCCTTC
              CATACACCAAAAAACACTTCTGTTTCTCTCAGTGGAGTGTCAGTTTCTCAAAACCAGCAT
              CGAGATGTAGTTCCTGAGCATGAGGCTCCCAGCAGTGAGGTAAGTCTTTATCCTGGTTGT
              GTGAGAAAGCCTTTTTGATATACAGTTGACCCTTAAACAAATGAAGGATTAAGGATATTG
              TCCCTCCCCCGTAGTCAAAAATTTGAGTATAATTTTTGACTCCTGAGAAACTTAACTACT

7315    CATGTGCAAGTACTTGTCAGATTATTTCCTTATAATAAATTCCTAGAAGGTGGATTGCTA
              CAAACAAGAAATGTATGTATTTTTGATACTTTTGATTTACATATTCAGAATAATATCCTG
              AAAGAACATACCAGTTTTCGTCTCACCAGCAGTAAATCTGAGTACTTACAGTTTTTAGTA
              TACAGAGTTGATATATAATGTACCTTTAACTCTTAACAAATCCTGACAAAAAAGGAGAT
              TGTTCTGTTTATTTAAAAAAAAAACTACTTAATTTTTAACTTTTATCTTTTTCTAGGTTAC
              [G,A]
              GTTCCTCTGAGTCATCTCATCAATGCCTTCCATACACCAAAAAACACTTCTGTTTCTCTC
              AGTGGAGTGTCAGTTTCTCAAAACCAGCATCGAGATGTAGTTCCTGAGCATGAGGCTCCC
              AGCAGTGAGGTAAGTCTTTATCCTGGTTGTGTGAGAAAGCCTTTTTGATATACAGTTGAC
              CCTTAAACAAATGAAGGATTAAGGATATTGTCCCTCCCCCGTAGTCAAAAATTTGAGTAT
              AATTTTTGACTCCTGAGAAACTTAACTACTAATACCCTACTATTGACCAGGAAGCCTTGC

7734    CCAGCAGTGAGGTAAGTCTTTATCCTGGTTGTGTGAGAAAGCCTTTTTGATATACAGTTG
              ACCCTTAAACAAATGAAGGATTAAGGATATTGTCCCTCCCCCGTAGTCAAAAATTTGAGT
              ATAATTTTTGACTCCTGAGAAACTTAACTACTAATACCCTACTATTGACCAGGAAGCCTT
              GCCGATAAAATAAAGGGTCCATTAACATATATTTTGTATATTTTATGTATTGTGTACTGT
              ATTCTTACAATAAAGTAAGATGGAGAAAATGTTATTAAGAAAATCATAAGGAAGAGAAA
              [T,C]
              ATATTTACCATTCATTAAGTAGAAGTGGACCATCATAAAGATCTTCATTATCTTCAAGTT
              GAGTGGGCTGAGGAGGAAGAGGAGGGGTTGGTTTTTCTGTCTCTGGTGGCAGAGACCGGA
```

FIGURE 3, page 17 of 29

8988
TATGTTCAGTGACTTCCTGACGAAGCTTAACATTGTTTCAATTGGCAAAGGAAAAATATT
CGAAGGGTACAGATCCATGTTCATGGAGCCAGCAAAAAGGATGAAGAAGAGCTTGGACAC
AACCGATAACTGGCACATCCGTCCAGAACCCTTCTCCCTCTCAATCCCTGTACACTGCGG
GTTTCTCCAAATGCCTATTGTCTATGATTTGTTTTGTCCATCGTTCTTAGTCACGGCTTA
GTTCAGGTTCTTGCCATCTTTCACTTGTTCCATCAGCCTTCTCTCTCATCCAGTCTAGTT
[G,T]
CTTTGTTTGTTTGTTTTATCATTTTTAAATTTTTTGTAAAGACAGGGTCTTGCTTTCTTC
ACCAGGCTGATCTCGAACTCCTGGCCTGAAGCAGTCCTCCCACCTCAGCCTCTCAAAAGT
GTTGGGATTACAGGCTCGAGCCACCATGCTAGGCCAGTCTATCTTCCTTAGTTCTCCATT
TTCTTCTATAAGACAGAACTAATCATGTTACTTAGAGAATTAAATTCAAACATGGCTCTT
CACAGTTTGGCCATAACCTATCTCTTTAATTTTTTCTTTCCTTGAATTTTTTGAGATATT

10290
ACTTTTTTGCCTGATTTTCACACAGTTTTGACTTTAATTTTCTTCTTTATTAGAAGATAT
GGGTAACTTTAGAACCTCTGAGTTCAAGGAAGGATCTAAGCAATGAGGCCAGAGGAGTGA
GATGTCCTATGGTAACCAAGCATACCATTTCTTTGTCAAGTGGGCTTTTGTTTATGGCTG
CTTAGGGGCTTAAAAGCTCCATGGACTGGTGAGGATTATCATTTGAATGGAATTTCCCCA
ATTCAAGAACCTTACTATTATCCTCCAATCAGTTCTACACTGTTGGGGAAAATCCCCTGG
[G,A]
CCTTATATAACATACTTTGTAACCCTGCAGTTAGTTACTCTTACACTCTTGTCATTATAA
ATGCTTGATCAATAGTTGATAGACTAGCTCTTGATCAGAGTACCCTTGTATGGAGAGAAG
GAAAAAATGCCATACATTTCACTTGATTCTGTGAACCATAATGCTTAGGACAGTAGTGGT
TTGGGTTTGATTTAAAAAAAAAAAAGTTTTTCTCATTCATGCTGAAATGTCATCTCTTTA
TTTAAGGATACCATTAGGAATATAATTTTTTAACCTATGTCAAACCTCATATGACTGATC

10315
TTTTGACTTTAATTTTCTTCTTTATTAGAAGATATGGGTAACTTTAGAACCTCTGAGTTC
AAGGAAGGATCTAAGCAATGAGGCCAGAGGAGTGAGATGTCCTATGGTAACCAAGCATAC
CATTTCTTTGTCAAGTGGGCTTTTGTTTATGGCTGCTTAGGGGCTTAAAAGCTCCATGGA
CTGGTGAGGATTATCATTTGAATGGAATTTCCCCAATTCAAGAACCTTACTATTATCCTC
CAATCAGTTCTACACTGTTGGGGAAAATCCCCTGGGCCTTATATAACATACTTTGTAACC
[C,A]
TGCAGTTAGTTACTCTTACACTCTTGTCATTATAAATGCTTGATCAATAGTTGATAGACT
AGCTCTTGATCAGAGTACCCTTGTATGGAGAGAAGGAAAAAATGCCATACATTTCACTTG
ATTCTGTGAACCATAATGCTTAGGACAGTAGTGGTTTGGGTTTGATTTAAAAAAAAAAAA
GTTTTTCTCATTCATGCTGAAATGTCATCTCTTTATTTAAGGATACCATTAGGAATATAA
TTTTTTAACCTATGTCAAACCTCATATGACTGATCTCAGTAAAACGAACTGTGAAAATAT

10495
CTGGTGAGGATTATCATTTGAATGGAATTTCCCCAATTCAAGAACCTTACTATTATCCTC
CAATCAGTTCTACACTGTTGGGGAAAATCCCCTGGGCCTTATATAACATACTTTGTAACC
CTGCAGTTAGTTACTCTTACACTCTTGTCATTATAAATGCTTGATCAATAGTTGATAGAC
TAGCTCTTGATCAGAGTACCCTTGTATGGAGAGAAGGAAAAAATGCCATACATTTCACTT
GATTCTGTGAACCATAATGCTTAGGACAGTAGTGGTTTGGGTTTGATTTAAAAAAAAAAA
[-,A]
GTTTTTCTCATTCATGCTGAAATGTCATCTCTTTATTTAAGGATACCATTAGGAATATAA
TTTTTTAACCTATGTCAAACCTCATATGACTGATCTCAGTAAAACGAACTGTGAAAATAT
TTGCATCAATTTATTTTTAAATATTAAAAAAGGAAATATATTTGTTAGACTTTTAAAAT
CTGATTGTTTAACTGATAATATGTACTCCTTAGGTTAAATATCTTGATAATATTAATGC
ATACCTGGTTGACCCAATCTTTTACAGCCTTCACTTAACTTAAGGGACCTTGGATTATCT

10566
ACACTGTTGGGGAAAATCCCCTGGGCCTTATATAACATACTTTGTAACCCTGCAGTTAGT
TACTCTTACACTCTTGTCATTATAAATGCTTGATCAATAGTTGATAGACTAGCTCTTGAT
CAGAGTACCCTTGTATGGAGAGAAGGAAAAAATGCCATACATTTCACTTGATTCTGTGAA
CCATAATGCTTAGGACAGTAGTGGTTTGGGTTTGATTTAAAAAAAAAAAAGTTTTTCTCA
TTCATGCTGAAATGTCATCTCTTTATTTAAGGATACCATTAGGAATATAATTTTTTAACC
[T,G]
ATGTCAAACCTCATATGACTGATCTCAGTAAAACGAACTGTGAAAATATTTGCATCAATT
TATTTTTAAATATTAAAAAAGGAAATATATTTGTTAGACTTTTAAAATCTGATTGTTTT
AACTGATAATATGTACTCCTTAGGTTAAATATCTTGATAATATTAATGCATACCTGGTTG
ACCCAATCTTTTACAGCCTTCACTTAACTTAAGGGACCTTGGATTATCTGAACTAAAAAT
TGGACAGATTGATCAGCTGGTAGAAAATCTACTTCCTGGATTTTGTAAAGGCAAAACAT

10608
TGTAACCCTGCAGTTAGTTACTCTTACACTCTTGTCATTATAAATGCTTGATCAATAGTT
GATAGACTAGCTCTTGATCAGAGTACCCTTGTATGGAGAGAAGGAAAAAATGCCATACAT
TTCACTTGATTCTGTGAACCATAATGCTTAGGACAGTAGTGGTTTGGGTTTGATTTAAAA
AAAAAAAGTTTTTCTCATTCATGCTGAAATGTCATCTCTTTATTTAAGGATACCATTAG
GAATATAATTTTTTAACCTATGTCAAACCTCATATGACTGATCTCAGTAAAACGAACTGT
[G,A]
AAAATATTTGCATCAATTTATTTTTAAATATTAAAAAAGGAAATATATTTGTTAGACTT

FIGURE 3, page 18 of 29

```
       TTAAAATCTGATTGTTTTAACTGATAATATGTACTCCTTAGGTTAAATATCTTGATAATA
       TTAATGCATACCTGGTTGACCCAATCTTTTACAGCCTTCACTTAACTTAAGGGACCTTGG
       ATTATCTGAACTAAAAATTGGACAGATTGATCAGCTGGTAGAAAATCTACTTCCTGGATT
       TTGTAAAGGCAAAAACATTTCTTCCCATTGGCATACATCCCATGTCTCTGCACAATCCTT

11648  ACCACGCCCGGCTAATTTTTTGTATTTTTAGTAGAGATGGGGTTTCACCGTGTTAGCCAG
       GATGATCTTGATCTCCTGACCTCGTGATCCACCCTCCTCAGCCTCCCAAAGTGCTGGGAT
       TATAGGCGTGAGCCACCGTGCAGGCCTAACATTGGTACCTTATTTTTAACTAAACTACAG
       ACTATTTGAATTTCAACAAAATTTGTTTTCACCAAATCACTAGTTCTCTGCAAGTGTCCT
       TTTTCTTTTCCAGGATCTGATCCAGCATACCACATTGCATTTAGCAGAATGGGGGGGCGG
       [G,T]
       GTTTGTTTTAATTTTAGGTGACACACATTTAATTCCAGGAAACATACTTAATCTTTGAGA
       ATACATTGATTAAAAAAACAGTTGTTATCCCTTTTGTGGAATGTCTACATTTTTTTTTAC
       TTGAATCTCATAACAGTATGGTAGTATAATAAGTGGGTTCATACTAGTCTGAAAAGGGAT
       GTCAACTTTATGAGTTTTTCTTTGGATGGCACTTAAACAGGCCATAAAAATCCAGGAACA
       AAATAGCAGGTTTGACTAGTTTATAATGAAGGTTTGATTTGAAGCTGTCCTTTGCATAAA

11665  TTTTGTATTTTTAGTAGAGATGGGGTTTCACCGTGTTAGCCAGGATGATCTTGATCTCCT
       GACCTCGTGATCCACCCTCCTCAGCCTCCCAAAGTGCTGGGATTATAGGCGTGAGCCACC
       GTGCAGGCCTAACATTGGTACCTTATTTTTAACTAAACTACAGACTATTTGAATTTCAAC
       AAAATTTGTTTTCACCAAATCACTAGTTCTCTGCAAGTGTCCTTTTTCTTTTCCAGGATC
       TGATCCAGCATACCACATTGCATTTAGCAGAATGGGGGGGCGGTGTTTGTTTTAATTTTA
       [G,A]
       GTGACACACATTTAATTCCAGGAAACATACTTAATCTTTGAGAATACATTGATTAAAAAA
       ACAGTTGTTATCCCTTTTGTGGAATGTCTACATTTTTTTTTACTTGAATCTCATAACAGT
       ATGGTAGTATAATAAGTGGGTTCATACTAGTCTGAAAAGGGATGTCAACTTTATGAGTTT
       TTCTTTGGATGGCACTTAAACAGGCCATAAAAATCCAGGAACAAAATAGCAGGTTTGACT
       AGTTTATAATGAAGGTTTGATTTGAAGCTGTCCTTTGCATAAACTTAATTCATTAATTCT

14162  TGCTTGTATCGACATCATTCAAGAGCTCTTCAAAGCATTTGTTCAGATCTTCAGTACTGG
       CCAGGTATGAAGCAACAACCATAAATTGTGGAAAAAAAAATATTTATTTACTATAGTCTG
       ATTTGTCTTTCTTAATGGTATTAATTCTAAACATTCATTTGCAATTCACAGGACCTAAAG
       AGTATTTGGAATTAATGAGTTTGGGTACTTCTGTATAATTTTTAATCTGGAAAATATATA
       GGAGCTAAATTTTGAGCGTGATAGTGCCACAATAAATCAAACTCCAGGGAACTTATCTAC
       [G,A]
       CTTGTTTCAAGATAAATGACTAACCACATTTGCTTACTCATCCTCACTTTCAAAAGCCCA
       TTGAAATTAATTTTATATATATATATATGAGAAAAAAAGAGCAACAACAGAAGCGTTCCG
       TTAACGGACGAGAAATTTGAGGGCTTTCAGTAAGTTGTAAAATAAGTGACATCAAATTGA
       CAGTAAAATCAAATTTGCATTTATTCATATAATTTTTGAATACAAGGCACTAGTGATAGA
       TGTCAGGTGATAGTGATCACTGTAAATGAAAAGACATGTTTTCTACCTTCATGGGACTA

14226  GTATGAAGCAACAACCATAAATTGTGGAAAAAAAAATATTTATTTACTATAGTCTGATTT
       GTCTTTCTTAATGGTATTAATTCTAAACATTCATTTGCAATTCACAGGACCTAAAGAGTA
       TTTGGAATTAATGAGTTTGGGTACTTCTGTATAATTTTTAATCTGGAAAATATATAGGAG
       CTAAATTTTGAGCGTGATAGTGCCACAATAAATCAAACTCCAGGGAACTTATCTACGCTT
       GTTTCAAGATAAATGACTAACCACATTTGCTTACTCATCCTCACTTTCAAAAGCCCATTG
       [A,C]
       AATTAATTTTATATATATATATATGAGAAAAAAAGAGCAACAACAGAAGCGTTCCGTTAA
       CGGACGAGAAATTTGAGGGCTTTCAGTAAGTTGTAAAATAAGTGACATCAAATTGACAGT
       AAAATCAAATTTGCATTTATTCATATAATTTTTGAATACAAGGCACTAGTGATAGATGTC
       AGGTGATAGTGATCACTGTAAATGAAAAGACATGTTTTCTACCTTCATGGGACTAATGG
       TGTCATGAAAGAGGTGGGTACTTCTGTTTCCAGTAGTAGAACTCAGGAAAAACCCCACTT

14250  TGGAAAAAAAATATTTATTTACTATAGTCTGATTTGTCTTTCTTAATGGTATTAATTCT
       AAACATTCATTTGCAATTCACAGGACCTAAAGAGTATTTGGAATTAATGAGTTTGGGTAC
       TTCTGTATAATTTTTAATCTGGAAAATATATAGGAGCTAAATTTTGAGCGTGATAGTGCC
       ACAATAAATCAAACTCCAGGGAACTTATCTACGCTTGTTTCAAGATAAATGACTAACCAC
       ATTTGCTTACTCATCCTCACTTTCAAAAGCCCATTGAAATTAATTTTATATATATATA
       [T,-]
       GAGAAAAAAGAGCAACAACAGAAGCGTTCCGTTAACGGACGAGAAATTTGAGGGCTTTC
       AGTAAGTTGTAAAATAAGTGACATCAAATTGACAGTAAAATCAAATTTGCATTTATTCAT
       ATAATTTTTGAATACAAGGCACTAGTGATAGATGTCAGGTGATAGTGATCACTGTAAATG
       AAAAAGACATGTTTTCTACCTTCATGGGACTAATGGTGTCATGAAAGAGGTGGGTACTTC
       TGTTTCCAGTAGTAGAACTCAGGAAAAACCCCACTTCCAGAGCCAGTAAAATTGGGCACT

14483  TAACCACATTTGCTTACTCATCCTCACTTTCAAAAGCCCATTGAAATTAATTTTATATAT
       ATATATATGAGAAAAAAAGAGCAACAACAGAAGCGTTCCGTTAACGGACGAGAAATTTGA
       GGGCTTTCAGTAAGTTGTAAAATAAGTGACATCAAATTGACAGTAAAATCAAATTTGCAT
       TTATTCATATAATTTTTGAATACAAGGCACTAGTGATAGATGTCAGGTGATAGTGATCAC
       TGTAAATGAAAAGACATGTTTTCTACCTTCATGGGACTAATGGTGTCATGAAAGAGGTG
       [G,A]
```

FIGURE 3, page 19 of 29

```
        GTACTTCTGTTTCCAGTAGTAGAACTCAGGAAAAACCCCACTTCCAGAGCCAGTAAAATT
        GGGCACTGGGATGGGATGGAATAAACAGTTGAAGATTGCCAGAAATGGGCCAATCACAGT
        GCAGATATGGCCTTTAACCTTTAGATAAATTAGCAAAAAACACCTTTCTAATAAGACGTC
        TGTGTGTGTGTGTGTGTGTGTGTGTGTGTGTGTGTGTGTCGAGGGACATCTGTC
        TGTGGAGACTCCTGGTTTGAGCATTGATGCCAAGGAAAGAAAGAAGCTAGCACCCCAGAT

15966   TAGCCAGGCATGGTGGCGTGTGCCTGTAATCCCAGCTACTTGGGAGGCTGAGGCAGGAGA
        ATCACTTGAACCCAGGAGGCGGAGGTTGCAGTGAGCCGAGACCGCGCCACTGAACTCCAG
        CCTGGCAACAGAGCGAGACTCCGTCTCAAAAAACAAAAAAGACAAAAAAAAACCTAAATAC
        TTGAAATTTTTAAAACCCTTTTCTAAATGTCTCACGACTGAATGGAAATAAAACCGGGAT
        TACAGACACTCAGTAATGAACCACAGTGAAAATCTGTATATCAGACTCTTGGTGAGGACA
        [A,G]
        AATGACATTGAGGGCGTTATATAATTTACTGAGAAATCAGGCTGGATGCAGTGGCTTATG
        CCTGTAATCCCAGCACTTTGGGAGGCTGAGTCAGGTGGATCACCTGAGGTCGGGAGTTCA
        AGACCAGCATGGCCAACATGGTAAAACCCCGTTCTCCACTAAAAAAGAAATACAAAATTA
        GCCAGGTGTGGTGGCACATGCCTGTAATCTCAGCTACTCGGGAGGCTGAGGCAGGATAAT
        CGCTTGAACCTGGGAGATGGAAGTTTCAGTGAGCCAAGATGGCACCTCCATCCTGGGCAA

16162   CCTTTTCTAAATGTCTCACGACTGAATGGAAATAAAACCGGGATTACAGACACTCAGTAA
        TGAACCACAGTGAAAATCTGTATATCAGACTCTTGGTGAGGACAAAATGACATTGAGGGC
        GTTATATAATTTACTGAGAAATCAGGCTGGATGCAGTGGCTTATGCCTGTAATCCCAGCA
        CTTTGGGAGGCTGAGTCAGGTGGATCACCTGAGGTCGGGAGTTCAAGACCAGCATGGCCA
        ACATGGTAAAACCCCGTTCTCCACTAAAAAAGAAATACAAAATTAGCCAGGTGTGGTGGC
        [A,G]
        CATGCCTGTAATCTCAGCTACTCGGGAGGCTGAGGCAGGATAATCGCTTGAACCTGGGAG
        ATGGAAGTTTCAGTGAGCCAAGATGGCACCTCCATCCTGGGCAACAGAGCAAGACTTTGT
        CTCAAAAAGAAAAAAAAATTTAAGACATAAAGATAGAAATAAATTGAATTTCTGAAAAA
        TAATAGAAGAAATTAATACACACAAAGCAAACATTTTAAAATAATAGGTGGAAATAGTTT
        TAATTAAACCAAAAACAAATTTAGTATAAAAAAAGGAACAATTTAACAATTCTGATTAAG

16565   AACAGAGCAAGACTTTGTCTCAAAAAGAAAAAAAAATTTAAGACATAAAGATAGAAAATA
        AATTGAATTTCTGAAAAATAATGAAGAAATTAATACACACAAAGCAAACATTTTAAAAT
        AATAGGTGGAAATAGTTTTAATTAAACCAAAAACAAATTTAGTATAAAAAAAGGAACAAT
        TTAACAATTCTGATTAAGAAACAACAGGAAAATACAGACAGTATTAGAAGTATGAGTGGG
        AATTGCCATGGATATGTGAAGGTTTTAAAATTGCAAGGTAGTATGTGTAACTTTATGTCA
        [T,A]
        AAATAAAAATATGTTGAAATGGACAATTGTCTAAGCAATTAATTAACAAAGTTAACCCAA
        GAAGAGATAGGATAATAACCATGAAGTTTAAAAGACAGTATTTTAAAAATATTGTCCCTT
        TGCCCCAGAGGCACTAGGTTCAGATAATTTTTATGGCTGCATTCTTCTAGAATCTTGAGT
        TTCTTTTTAATTTAAAACCTTATTAAAAAGAAAAAGATAGAGTTCCCTATTTATTCCATG
        AGATTGCTGTTAGTAAAACTTTTTAGTATTAGCATAAGGCCAGGCACTGTGGATCACACC

16815   GATATGTGAAGGTTTTAAAATTGCAAGGTAGTATGTGTAACTTTATGTCATAAATAAAAA
        TATGTTGAAATGGACAATTGTCTAAGCAATTAATTAACAAAGTTAACCCAAGAAGAGATA
        GGATAATAACCATGAAGTTTAAAAGACAGTATTTTAAAAATATTGTCCCTTTGCCCCAGA
        GGCACTAGGTTCAGATAATTTTTATGGCTGCATTCTTCTAGAATCTTGAGTTTCTTTTTA
        ATTTAAAACCTTATTAAAAAGAAAAAGATAGAGTTCCCTATTTATTCCATGAGATTGCTG
        [T,C]
        TAGTAAAACTTTTTAGTATTAGCATAAGGCCAGGCACTGTGGATCACACCTGTAATCCCA
        ACACTTTGGGATGATCGCTTGAAGCCAGGAGTTCAAAACAAGCCCAGACATCATCTCAAC
        AACAGCAACAAAAATTAGCCCGTCGTGGTATCATGCCCCTGTAGTTCTGGATACTTGGGA
        GGCTGAGGTGAAAGGTTTGCTTGAGCCCAAAGTTCAAGGTTACAGTGAGCTATGATCATG
        CCACCGTACTTCAGCTTGAGTGACAGCAAGATCCTATCTAAAAAATATATATATGTATAT

17110   TGCTGTTAGTAAAACTTTTTAGTATTAGCATAAGGCCAGGCACTGTGGATCACACCTGTA
        ATCCCAACACTTTGGGATGATCGCTTGAAGCCAGGAGTTCAAAACAAGCCCAGACATCAT
        CTCAACAACAGCAACAAAAATTAGCCCGTCGTGGTATCATGCCCCTGTAGTTCTGGATAC
        TTGGGAGGCTGAGGTGAAAGGTTTGCTTGAGCCCAAAGTTCAAGGTTACAGTGAGCTATG
        ATCATGCCACCGTACTTCAGCTTGAGTGACAGCAAGATCCTATCTAAAAAATATATATAT
        [G,A]
        TATATATGTATGTATCTGTGTCTGAATGTATATACACACGCAAGCACGACAGAGGAACAA
        AATAGATGTGTTTCACTTAACAGAAATCCTAAATAAAATCTGAAGAAAGCAAATCTAGAA
        ATGTGCTAAAAATATTATATCATGATTAAGGAATACAAAAGTGATTTAAGATTATTAGTA
        AGTCAATTTATCATATTGATTAGAAAAGAAAAATATCATTATTTCAATGTATGATAAAAA
        GACATGATATATTTTAATTGCTGTGCTTCCTGAAAACTCTTAGAAAGTTAGAAATGGAAG

18464   AATCAATAAGCAAATGATGGATTATCAAATGTTATCAGCCTAAGTGGCTGTTTTGGAAAA
        ATCAAGTTCTTTTCTTACATCATACCAAAAAAAAAAGTTCCAAATATGTTAAAGGGTTGA
        AAACAAAATATAAAACTGAAAATATTAGAAGTAAGTAGACTACCTTTAAAATCTTAGTT
        TGGCAATGAAACTCTAATCAAGTTAAAATGCAGAAAACACAGCAAAGGTATGGCTGCACT
        GAGCTAATAAATTACTGTATATGATCGAAAGACAAAGCACATTAAAATAAATGTTTACA
```

FIGURE 3, page 20 of 29

```
        [G,A]
        TATATATAACTAAAGATTACTATCTGTAACATCCATATTATCTAAATAAAAATGGAAAAA
        TGTGCAAAGGACATGCATGGTCAATTTACTAAAGAAATAAAAATAAAAATAGTCAATAAA
        AATACAGAGGAAGCTTTTCAAAATTTTCCCACACTTGTAATCTGGGAAATGCAAAGTAAA
        ACAAGGTACTGTTATTTTTGCCCGTCAGACTTGCACAAATTTAAAAGATTCATATTATTT
        AGTGTCGGCAAGGATATGAAGAAAAGGAAACTCATAAGCATTGGTGGGCACATAAATTGA

18500   AGCCTAAGTGGCTGTTTTGGAAAAATCAAGTTCTTTTCTTACATCATACCAAAAAAAAAA
        GTTCCAAATATGTTAAAGGGTTGAAAACAAAAATATAAAACTGAAAATATTAGAAGTAAG
        TAGACTACCTTTAAAATCTTAGTTTGGCAATGAAACTCTAATCAAGTTAAAATGCAGAAA
        ACACAGCAAAGGTATGGCTGCACTGAGCTAATAAATTACTGTATATGATCGAAAGACAAA
        GACACATTAAAATAAATGTTTACAGTATATATAACTAAAGATTACTATCTGTAACATCCA
        [T,C]
        ATTATCTAAATAAAAATGGAAAAATGTGCAAAGGACATGCATGGTCAATTTACTAAAGAA
        ATAAAAATAAAAATAGTCAATAAAAATACAGAGGAAGCTTTTCAAAATTTTCCCACACTT
        GTAATCTGGGAAATGCAAAGTAAAACAAGGTACTGTTATTTTTGCCCGTCAGACTTGCAC
        AAATTTAAAAGATTCATATTATTTAGTGTCGGCAAGGATATGAAGAAAAGGAAACTCATA
        AGCATTGGTGGGCACATAAATTGATAACAGCCTTTTTAGAAAGTAGTCTCTTAGTGTCA

18864   AAAATAAAAATAGTCAATAAAAATACAGAGGAAGCTTTTCAAAATTTTCCCACACTTGTA
        ATCTGGGAAATGCAAAGTAAAACAAGGTACTGTTATTTTTGCCCGTCAGACTTGCACAAA
        TTTAAAAGATTCATATTATTTAGTGTCGGCAAGGATATGAAGAAAAGGAAACTCATAAGC
        ATTGGTGGGCACATAAATTGATAACAGCCTTTTTAGAAAGTAGTCTCTTAGTGTCAAAC
        AAAATTTAAACCTTAACAGTGTTTCTTTCAGGAATTCAGTCTACATCTGCTGACATACAT
        [G,A]
        TATAAGAATGTTCACCACAGTATTGTTTCCAGCAATAAAAACCAGAAAACAAATAATGTT
        CAGGGAAATGGTTGAATGAATTGCACTGTGATAAATTGGAAAAGTGTAAACAGCCATTAA
        ACTGAATGCACTGTTCTGTTCTGAAAAATATGCACGAAAAATGAAAATTGCAAAAAATTA
        GGTACTATTTCTAGAGTAGTTTTTATAGAAAGAGCACCTGTGTGCATGCATACAAGGGTA
        GTCAGAATTGTTAACAGGTTATACTTCTGGGAAGTGGGATTGGGGCTTGAGAAATTAGAA

18975   TTGCACAAATTTAAAAGATTCATATTATTTAGTGTCGGCAAGGATATGAAGAAAAGGAAA
        CTCATAAGCATTGGTGGGCACATAAATTGATAACAGCCTTTTTAGAAAGTAGTCTCTTA
        GTGTCAAACAAAATTTAAACCTTAACAGTGTTTCTTTCAGGAATTCAGTCTACATCTGCT
        GACATACATGTATAAGAATGTTCACCACAGTATTGTTTCCAGCAATAAAAACCAGAAAAC
        AAATAATGTTCAGGGAAATGGTTGAATGAATTGCACTGTGATAAATTGGAAAAGTGTAAA
        [C,T]
        AGCCATTAAACTGAATGCACTGTTCTGTTCTGAAAAATATGCACGAAAAATGAAAATTGC
        AAAAAATTAGGTACTATTTCTAGAGTAGTTTTTATAGAAAGAGCACCTGTGTGCATGCAT
        ACAAGGGTAGTCAGAATTGTTAACAGGTTATACTTCTGGGAAGTGGGATTGGGGCTTGAG
        AAATTAGAAGACACTAATTTGATACACTTACCCTTTTTCAAAAACATTATGTAATTACC
        AAAAACATGTAAAAATCAGTTGTGTAGATTCAATCTATTTTAATTACTTGGTTGGGTTTT

19780   TGCTTGAACCCAGGAGGCGGAGGTTGCAGTGAGCAGCAATGCCTTGCACTCCAGCCTGGG
        CAACAAGAGTGAAACTCCATCTCAAATAAATAAATAAATAAATAAATAAAGTTCCT
        TTTGAAAAAGGAGGATAGAAAAAACTATAAGCTGGGCATGATAGATTTAAGTTCTCAGA
        CCTAATCCCAGCTCTTTGGGAGGCTGAGGCAAGAGGACTGCTTGAGCCCAGGAGTTCAAG
        GCCAGCCTGGGCAATAAAAGGAGACCCCGTCTCTACAAAAAAGAAGGAAACAAAGGAAAA
        [T,C]
        GTATTGAAGTGTCAGGCAAATTAGATAGACTAGGATATACAGGTAGGGTGTCAGACTTTA
        GAATCTTAGGCATTTTTCTTTTCCTGTAACAATTTATAGTGACAGTGAATGGTATTGTTT
        TATTTAGTTTTCATACAGTCTCGGGGTTTTAAAACTTTGAAATCAAGGACACGACGTCTC
        CAGTCTACCTCCGAGAGATTAGCTGAAACACAGAATATAGCGCCATCATTCGTGAAGGTA
        ATTAGACCTTTTTATGATCCAAAAAGCAAATATTTTCAAGTTGTTAGAGTGAGGAGCTTC

20201   TATTTAGTTTTCATACAGTCTCGGGGTTTTAAAACTTTGAAATCAAGGACACGACGTCTC
        CAGTCTACCTCCGAGAGATTAGCTGAAACACAGAATATAGCGCCATCATTCGTGAAGGTA
        ATTAGACCTTTTTATGATCCAAAAAGCAAATATTTTCAAGTTGTTAGAGTGAGGAGCTTC
        AATATCTGATTTCTTTTGTTGGCTGATAGATATTCTTCCTTCTTTCCACTAATAATAAGG
        GATTAGTAACCTGTGTAATCATTATACCTCTAACTCTTCTGGGCACCAGACTTGCCTCTC
        [C,T]
        ACTTACTAGATTTTTTTCCCACAAACCTACACCTGTCGAGGTGTTCTCTGTATTAATGAG
        CAGCATCCACCCAAGCTAAAAACCTGGCTATCAACCTACGTTTGTCCATGTTGCCTTACC
        TCCCACATCCATTAACCACTAAAGTCCTGTTGATCCAACCTCCTAAATATTTCTTACATC
        TGTTCCACTGCCATAGATAGGCTATAACTATTTGTTGCCTAAATTACTGTAATGAATACT
        TGTTTAGTCTCCTTGCCTCTAGTCTTGCTGCGTTCAGTCCAGCCTCCAGACTGCCACCCA

21014   GCCTCCGTCAGATTGTTCATAGTGTTTATTCCCTGTGTTTTAGATGTCCTATTCTCTGTA
        AGGCCTTTTCCATATTCCTGAGGTAGCATTGATTTACCACCATACATAATACTTCTAACA
        TAATATCAAAATGATTTAAGAAACTTAGTTATTTATATATCTTTTTCCAGTAGACTGAAA
        ACTTTAAGATCAGTGGTTTATTTATCTTTACATCTTCAGAACTTATATAAGGCCAAGTAT
```

```
        ATGAACGGTGCTTAGTAGACATTTAGTAAATTAATGAGATTTTTTCCTCTAGCAAAGATA
        [A,G]
        AGGGATAAGAACATTAAGCCAATCAAACCCTAAAATAATATGTGACCTGTTTTCAGTGTA
        GTGTTCGTGCAGAGAATAATGCCACTTTCTTTATATTATTAATTGATTGATGCAGGAATG
        GGATCTAGTGTTAGTTTCCTAGTTATTGATTAATTCATTGCTGAGTCTTAATCTGTTTCT
        TCACATTGACAGTAAAAATTATACAGAATTTTAGTGAATTTTTTGAGTGGTCACAATAT
        TGTTGGGAAGTATCACTGTGTTGTTAACCAGTACTGATGTGTTGTTTGTGTATTCAGGGG

21022   CAGATTGTTCATAGTGTTTATTCCCTGTGTTTTAGATGTCCTATTCTCTGTAAGGCCTTT
        TCCATATTCCTGAGGTAGCATTGATTTACCACCATACATAATACTTCTAACATAATATCA
        AAATGATTTAAGAAACTTAGTTATTTATATCTTTTTCCAGTAGACTGAAAACTTTAAG
        ATCAGTGGTTTATTTATCTTTACATCTTCAGAACTTATATAAGGCCAAGTATATGAACGG
        TGCTTAGTAGACATTTAGTAAATTAATGAGATTTTTTCCTCTAGCAAAGATAAAGGGATA
        [A,T]
        GAACATTAAGCCAATCAAACCCTAAAATAATATGTGACCTGTTTTCAGTGTAGTGTTCGT
        GCAGAGAATAATGCCACTTTCTTTATATTATTAATTGATTGATGCAGGAATGGGATCTAG
        TGTTAGTTTCCTAGTTATTGATTAATTCATTGCTGAGTCTTAATCTGTTTCTTCACATTG
        ACAGTAAAAATTATACAGAATTTTAGTGAATTTTTTTGAGTGGTCACAATATTGTTGGGA
        AGTATCACTGTGTTGTTAACCAGTACTGATGTGTTGTTTGTGTATTCAGGGGTTTCTTTT

21712   GTTTTGCGGAAGGTTTTCTGAAAGCTCAAGCACTCACACAAAAAACCAATGGTAAGTTGA
        ATTGACACCATCCGTGTTTGAGAAGAGTAACTGAAAGGAAGTCATAGTCCTACATTTAAG
        TTTTAAGTAACTTTTCTAAGACCATCTATTGATTAAATTCCACTATATTTGTAACTTAAT
        CTATGTAGAAATGGCGATACTGCTGATGGTTTCCCTTTCTCAAGAGAGAAAACAAATTGG
        AGAACAGGAAGTGTGAATGGCTTCATAAAGGTTTTTGTTTCTTTATTTTTTGTTTGTGTT
        [T,C]
        GTTTTTGAGACACGGTCTTGCTTCATTGCCTAAGCCAGAGTGCAGTGGTGCAATCATGGC
        TCATTGTAGCCTTAACTTTCTGGGCTCAAGTGATCCTCTCACCTCAGCCTCCTGAGTAGC
        TAGGATCACAGGCATGTGCCACCACGCCCAGCTAATTTTTGTGGAGATGGAATCTTGCCC
        TGTTGTCCAGGCTGGTCTTGAACTCCAGGGATCAAGTGATCCTCCTGCCTTGACCTCTTA
        AAATGCTAGGATTACAGGCATGAGCCACCATGCTTGGCCTTAAGTTTTTGATAATAGGGT

22809   ATTTTATAATGGCAATACAAGCTGAAATAGTCTTCTATTTCAAAGATAAACAAATTCAGT
        TTATTCATAAAATCACATTAAATGTTTCCCTTTTTTTAGTTTGCTTATCTGAAATTAAG
        CAATAGTGTCAGACTTACGTGGTTCCAATTACCTTTTCCACTACTGTGCAGTTTTCACCC
        TGTGTTGCCTATTCTCTTAAATATTAAGGATATGTACAGATTCTTAAAAAATACTTTGTG
        GGCCAAAACTATTGGTGTTCATTCTAGAATTACTATTTTAAATTTGTTTTCCCAGCTTCT
        [A,G]
        TGTTCCTGATTTATTAAGCATTTCTCCTTAACCCCATATTTTGCCAGCTCATTTTTCAGC
        CTATCTTAACAGTATTTTGGGCTTCTTCTGAGGAAATTAGAAATTGCTCAATTTACTCAT
        TTATAACTGCTCTAGTTTGGAAGTTTCTACCTGAGTGGGAAAGACTTAAGAAATCCTTGT
        AATAGTTCTCCAAAATTGATCTCAAATATTTTACTCTCCCTATCAGACTTTTTCTGTCTT
        GCTTGTCAGACTTAATGTTGTCATAATTGATAGGTCATTTGAGGGCAAGTAATAACAGTT

23025   CAGATTCTTAAAAAATACTTTGTGGGCCAAAACTATTGGTGTTCATTCTAGAATTACTAT
        TTTAAATTTGTTTTCCCAGCTTCTATGTTCCTGATTTATTAAGCATTTCTCCTTAACCCC
        ATATTTTGCCAGCTCATTTTTCAGCCTATCTTAACAGTATTTTGGGCTTCTTCTGAGGAA
        ATTAGAAATTGCTCAATTTACTCATTTATAACTGCTCTAGTTTGGAAGTTTCTACCTGAG
        TGGGAAAGACTTAAGAAATCCTTGTAATAGTTCTCCAAAATTGATCTCAAATATTTTACT
        [C,G]
        TCCCTATCAGACTTTTTCTGTCTTGCTTGTCAGACTTAATGTTGTCATAATTGATAGGTC
        ATTTGAGGGCAAGTAATAACAGTTGTCAGAGGAAGAAGACTACATGAAAAGTATAATAAT
        GTGTTAAGCCTCAATTTTTTATTAATGTGTGTCAATGTTTTCTGCTAACTTTAAGGCAAT
        GTGTTTCAAAGTGTAGACCTGTGACCAATTAGAATAATTGAAGTGTTTGTTAAAAATGAA
        AATTCTCCTGGGCCCTGTGCTGTGGCCTGAGAATTAACATACTTCTCAAGTGAGTTTTAT

23029   TTCTTAAAAAATACTTTGTGGGCCAAAACTATTGGTGTTCATTCTAGAATTACTATTTTA
        AATTTGTTTTCCCAGCTTCTATGTTCCTGATTTATTAAGCATTTCTCCTTAACCCCATAT
        TTTGCCAGCTCATTTTTCAGCCTATCTTAACAGTATTTTGGGCTTCTTCTGAGGAAATTA
        GAAATTGCTCAATTTACTCATTTATAACTGCTCTAGTTTGGAAGTTTCTACCTGAGTGGG
        AAAGACTTAAGAAATCCTTGTAATAGTTCTCCAAAATTGATCTCAAATATTTTACTCTCC
        [C,-]
        TATCAGACTTTTTCTGTCTTGCTTGTCAGACTTAATGTTGTCATAATTGATAGGTCATTT
        GAGGGCAAGTAATAACAGTTGTCAGAGGAAGAAGACTACATGAAAAGTATAATAATGTGT
        TAAGCCTCAATTTTTTATTAATGTGTGTCAATGTTTTCTGCTAACTTTAAGGCAATGTGT
        TTCAAAGTGTAGACCTGTGACCAATTAGAATAATTGAAGTGTTTGTTAAAAATGAAAATT
        CTCCTGGGCCCTGTGCTGTGGCCTGAGAATTAACATACTTCTCAAGTGAGTTTTATTCAC

23208   AGAAATTGCTCAATTTACTCATTTATAACTGCTCTAGTTTGGAAGTTTCTACCTGAGTGG
        GAAAGACTTAAGAAATCCTTGTAATAGTTCTCCAAAATTGATCTCAAATATTTTACTCTC
        CCTATCAGACTTTTTCTGTCTTGCTTGTCAGACTTAATGTTGTCATAATTGATAGGTCAT
```

FIGURE 3, page 22 of 29

```
         TTGAGGGCAAGTAATAACAGTTGTCAGAGGAAGAAGACTACATGAAAAGTATAATAATGT
         GTTAAGCCTCAATTTTTTATTAATGTGTGTCAATGTTTTCTGCTAACTTTAAGGCAATGT
         [G,A]
         TTTCAAAGTGTAGACCTGTGACCAATTAGAATAATTGAAGTGTTTGTTAAAAATGAAAAT
         TCTCCTGGGCCCTGTGCTGTGGCCTGAGAATTAACATACTTCTCAAGTGAGTTTTATTCA
         CACCAAAGTTTGAGAAACTTTGATTTAAGATTTCTATCATTAGATACTACAATAAGAAGT
         AGAAAATAATTTTTGATTTTATTAACTGAAAAGTACAAATAGGTCATTTTATTTTATTTT
         TTTATTTTATTTCATTTATTTTTTTTGAGATGGAGTCTCGCTCTGTTGCCCAGGCTGGAG

25083    GCAGCCTGGTGTAGTGGAGTGAATGTGGACTTCAGAGTCAAGCTGACTAATGTTTGAAAT
         TCATTTTTATACTTATTAGCTATGAGACCTTGAAGAAATTACTTTAGATCCTGACAGATA
         ATGTATGTGCTTGACACATAGTAGATATTTAATAAATGGTCCTTCTTTACCTGTACCTCT
         TACTGATCTTTGTAACTCCACTATCTAAAACATGTTAGACAATGTATATTTCTTGAATGA
         ATAGAATGGATAAATGCTAGTTTATAGTTGATTAATTTGTTAAATATTTAATAGTATCTA
         [T,-]
         TAAGTGCTAGGCCCTATTTTAGCTGCTGGGATAGAATAAATAATCTCTGCATTCTTAGAG
         TTTAAACTCTAAAAGCAGTAATTGGACACTGATATGTGATGTAAGAAAAAGTAGAGTATG
         TTAAAAGAATAAAAGTGTATGGAGGAAAAAGTAGAGCAGGGTAAAGAGGATTGGGAGTTT
         TGAGAGAAGGCTTACAGTTTTAAATGGAGTGTTCAAGGTGTGATTGATGGAGAAGGTGAC
         ATTTGAGATAAAATCTGAAGGAGAAGATGGAATAAACTGCATTTATCTGAGAAAGGAACG

25186    TTAGATCCTGACAGATAATGTATGTGCTTGACACATAGTAGATATTTAATAAATGGTCCT
         TCTTTACCTGTACCTCTTACTGATCTTTGTAACTCCACTATCTAAAACATGTTAGACAAT
         GTATATTTCTTGAATGAATAGAATGGATAAATGCTAGTTTATAGTTGATTAATTTGTTAA
         ATATTTAATAGTATCTATTAAGTGCTAGGCCCTATTTTAGCTGCTGGGATAGAATAAATA
         ATCTCTGCATTCTTAGAGTTTAAACTCTAAAAGCAGTAATTGGACACTGATATGTGATGT
         [A,C]
         AGAAAAAGTAGAGTATGTTAAAAGAATAAAAGTGTATGGAGGAAAAAGTAGAGCAGGGTA
         AAGAGGATTGGGAGTTTTGAGAGAAGGCTTACAGTTTTAAATGGAGTGTTCAAGGTGTGA
         TTGATGGAGAAGGTGACATTTGAGATAAAATCTGAAGGAGAAGATGGAATAAACTGCATT
         TATCTGAGAAAGGAACGTTTCTGACCAAAGGAACAGTTTGAGCAAAGGCTCTCAAGTAAT
         AGGGTGTCTGACTTGTTCATTTTTGAAAGTAGAACTAATAGGATTTCTTATTGGAACGTA

25741    GTTCATTTTTGAAAGTAGAACTAATAGGATTTCTTATTGGAACGTAGGGTGTAAGAGAAA
         AGAGGAGTCAAAAAGAGCCACAAGATTTTTGGTCTCAGCAATTAGAAGGATAGAATTGAC
         ATTTACTGAGATTTTTGTTTTTGTTTTTGAGACGGAGTTTCGCTATTGTTGCCCAAGCTG
         GCGTGCAATGGCGTGATCTCGGCTCAGTGCAACCTCCACCTCCCAGATTCAAGCGATTCT
         CCTGCCTCAGCCTCCAGAGTAGCTGGGATTACAGGCACGAGCCACCACGCCCAGCTAATT
         [T,G]
         TTTGTGTTTTTAGTAGAAACAGGGTTTTACCATGTTAGCCAGGCTGGTCTTGAACTCCTG
         ACCTCAGGTGATCCACGCAGATCAAAGTGCTGGGATTACAGGCGTGAGCCACGGTGCCCG
         GCCTTTAGTGAGGTTTTAAAAGGCTGTGAGTGGAGCAGATCTGGGGGACAAAGGTTAGAA
         ATTTAGTTTTAGGTATGTTAAGTGTGAGAGATACGAATGAAAGTGTTGAGTAACTTGGAT
         ATACCACTTTGGAGGTATGGGAGAGGTCTGAGCTAGAATTAAAAATAGGAGATTATATTT

25764    ATAGGATTTCTTATTGGAACGTAGGGTGTAAGAGAAAAGAGGAGTCAAAAAGAGCCACAA
         GATTTTTGGTCTCAGCAATTAGAAGGATAGAATTGACATTTACTGAGATTTTTGTTTTTG
         TTTTTGAGACGGAGTTTCGCTATTGTTGCCCAAGCTGGCGTGCAATGGCGTGATCTCGGC
         TCAGTGCAACCTCCACCTCCCAGATTCAAGCGATTCTCCTGCCTCAGCCTCCAGAGTAGC
         TGGGATTACAGGCACGAGCCACCACGCCCAGCTAATTTTTTGTGTTTTTAGTAGAAACAG
         [G,A]
         GTTTTACCATGTTAGCCAGGCTGGTCTTGAACTCCTGACCTCAGGTGATCCACGCAGATC
         AAAGTGCTGGGATTACAGGCGTGAGCCACGGTGCCCGGCCTTTAGTGAGGTTTTAAAAGG
         CTGTGAGTGGAGCAGATCTGGGGGACAAAGGTTAGAAATTTAGTTTTAGGTATGTTAAGT
         GTGAGAGATACGAATGAAAGTGTTGAGTAACTTGGATATACCACTTTGGAGGTATGGGAG
         AGGTCTGAGCTAGAATTAAAAATAGGAGATTATATTTATATGTATGTTAAGTCCACATGT

25831    GGTCTCAGCAATTAGAAGGATAGAATTGACATTTACTGAGATTTTTGTTTTTGTTTTTGA
         GACGGAGTTTCGCTATTGTTGCCCAAGCTGGCGTGCAATGGCGTGATCTCGGCTCAGTGC
         AACCTCCACCTCCCAGATTCAAGCGATTCTCCTGCCTCAGCCTCCAGAGTAGCTGGGATT
         ACAGGCACGAGCCACCACGCCCAGCTAATTTTTTGTGTTTTTAGTAGAAACAGGGTTTTA
         CCATGTTAGCCAGGCTGGTCTTGAACTCCTGACCTCAGGTGATCCACGCAGATCAAAGTG
         [C,T]
         TGGGATTACAGGCGTGAGCCACGGTGCCCGGCCTTTAGTGAGGTTTTAAAAGGCTGTGAG
         TGGAGCAGATCTGGGGGACAAAGGTTAGAAATTTAGTTTTAGGTATGTTAAGTGTGAGAG
         ATACGAATGAAAGTGTTGAGTAACTTGGATATACCACTTTGGAGGTATGGGAGAGGTCTG
         AGCTAGAATTAAAAATAGGAGATTATATTTATATGTATGTTAAGTCCACATGTTTGGATG
         AGATCACCCAGGGAGTGAGTGTAACCAGAAGAGAGATTTAAATACCGAGTTACAGAGCAC

25927    AATGGCGTGATCTCGGCTCAGTGCAACCTCCACCTCCCAGATTCAAGCGATTCTCCTGCC
         TCAGCCTCCAGAGTAGCTGGGATTACAGGCACGAGCCACCACGCCCAGCTAATTTTTTGT
```

FIGURE 3, page 23 of 29

```
              GTTTTTAGTAGAAACAGGGTTTTACCATGTTAGCCAGGCTGGTCTTGAACTCCTGACCTC
              AGGTGATCCACGCAGATCAAAGTGCTGGGATTACAGGCGTGAGCCACGGTGCCCGGCCTT
              TAGTGAGGTTTTAAAAGGCTGTGAGTGGAGCAGATCTGGGGGACAAAGGTTAGAAATTTA
              [G,C]
              TTTTAGGTATGTTAAGTGTGAGAGATACGAATGAAAGTGTTGAGTAACTTGGATATACCA
              CTTTGGAGGTATGGGAGAGGTCTGAGCTAGAATTAAAAATAGGAGATTATATTTATATGT
              ATGTTAAGTCCACATGTTTGGATGAGATCACCCAGGGAGTGAGTGTAACCAGAAGAGAGA
              TTTAAATACCGAGTTACAGAGCACTTACTTGAAGGTTCACAAGACAGAGAAGAGAAGCCA
              GGAACCAAGATGAGAAGGAGCTGCCAGTGAGTTAGGTGACAATGGTATCCTGGAAGAAAA

27184    CCGCAGGAGGGATTTGAAGTACGTGATCTGAGGACTCTTCCAACTCTGAAGAGATTGGTT
              ATGTTATTATTTCTGCTTTTCTTCTTTACTTATTCGTGTCTCTGTTTATACATAACCATG
              TTTTTTCAGCCTTGACTATTGGGGAATAAGGCATTGGGAATCATTATGATAGTTTTACAA
              CCAAGTAGTTCTTTCCTTTCCTTTCCAGTTTAAATGGCTATGAACCCTGTTGGAATTGTA
              TAAAGGGAACAATTGAGGAAGAGGTTGGTGCAGTGATTATTTGAAAACTTCAGTCATCAG
              [T,C]
              GTGGAGGGCCCTTCTCATTGTGTTTGAGGTCTGCATGCCTTTTCTAAATTGAGCCTGTAT
              TAAGGCTGAGGTCAGACACAGCATTGTTATTCTCTGTCTGTAATGTACTTACATACTTAC
              TGAATATATCACACTTCTTTTGGAATGAGAGTTTTTTTTTTTTTTTTTTTTTTTTTTTGA
              GACAGGGTCTTGCTCTCTTGCCCAGGCTGGAGTGCAGTGGCATGATCATGGCTCACTGCA
              GCTTTGACCTTCTGGGCTCAAGTGATACTCCTGCCTTAACCTCCCTTGTAGCTGAGACCA

27235    AGATTGGTTATGTTATTATTTCTGCTTTTCTTCTTTACTTATTCGTGTCTCTGTTTATAC
              ATAACCATGTTTTTTCAGCCTTGACTATTGGGGAATAAGGCATTGGGAATCATTATGATA
              GTTTTACAACCAAGTAGTTCTTTCCTTTCCTTTCCAGTTTAAATGGCTATGAACCCTGTT
              GGAATTGTATAAAGGGAACAATTGAGGAAGAGGTTGGTGCAGTGATTATTTGAAAACTTC
              AGTCATCAGCGTGGAGGGCCCTTCTCATTGTGTTTGAGGTCTGCATGCCTTTTCTAAATT
              [G,A]
              AGCCTGTATTAAGGCTGAGGTCAGACACAGCATTGTTATTCTCTGTCTGTAATGTACTTA
              CATACTTACTGAATATATCACACTTCTTTTGGAATGAGAGTTTTTTTTTTTTTTTTTTT
              TTTTTTTGAGACAGGGTCTTGCTCTCTTGCCCAGGCTGGAGTGCAGTGGCATGATCATGG
              CTCACTGCAGCTTTGACCTTCTGGGCTCAAGTGATACTCCTGCCTTAACCTCCCTTGTAG
              CTGAGACCACAGGCATGCACCACCACACTTGGCTAATTTTTTAATTTAATTTTATTATTC

27313    CCTTGACTATTGGGGAATAAGGCATTGGGAATCATTATGATAGTTTTACAACCAAGTAGT
              TCTTTCCTTTCCTTTCCAGTTTAAATGGCTATGAACCCTGTTGGAATTGTATAAAGGGAA
              CAATTGAGGAAGAGGTTGGTGCAGTGATTATTTGAAAACTTCAGTCATCAGCGTGGAGGG
              CCCTTCTCATTGTGTTTGAGGTCTGCATGCCTTTTCTAAATTGAGCCTGTATTAAGGCTG
              AGGTCAGACACAGCATTGTTATTCTCTGTCTGTAATGTACTTACATACTTACTGAATATA
              [T,C]
              CACACTTCTTTTGGAATGAGAGTTTTTTTTTTTTTTTTTTTTTTTTTGAGACAGGGTC
              TTGCTCTCTTGCCCAGGCTGGAGTGCAGTGGCATGATCATGGCTCACTGCAGCTTTGACC
              TTCTGGGCTCAAGTGATACTCCTGCCTTAACCTCCCTTGTAGCTGAGACCACAGGCATGC
              ACCACCACACTTGGCTAATTTTTTAATTTAATTTTATTATTCTTTCTAGACAGGGTCTGG
              CTCTATCACCCAGACTGAAGTGCAGTAGTGTGATCTTAGCTCACAACAACCTCCTCCTCC

27362    AACCAAGTAGTTCTTTCCTTTCCTTTCCAGTTTAAATGGCTATGAACCCTGTTGGAATTG
              TATAAAGGGAACAATTGAGGAAGAGGTTGGTGCAGTGATTATTTGAAAACTTCAGTCATC
              AGCGTGGAGGGCCCTTCTCATTGTGTTTGAGGTCTGCATGCCTTTTCTAAATTGAGCCTG
              TATTAAGGCTGAGGTCAGACACAGCATTGTTATTCTCTGTCTGTAATGTACTTACATACT
              TACTGAATATATCACACTTCTTTTGGAATGAGAGTTTTTTTTTTTTTTTTTTTTTTTTT
              [-,T]
              GAGACAGGGTCTTGCTCTCTTGCCCAGGCTGGAGTGCAGTGGCATGATCATGGCTCACTG
              CAGCTTTGACCTTCTGGGCTCAAGTGATACTCCTGCCTTAACCTCCCTTGTAGCTGAGAC
              CACAGGCATGCACCACCACACTTGGCTAATTTTTTAATTTAATTTTATTATTCTTTCTAG
              ACAGGGTCTGGCTCTATCACCCAGACTGAAGTGCAGTAGTGTGATCTTAGCTCACAACAA
              CCTCCTCCTCCTGGGCTCCAGCCATCCTCCCGCCTCAGCCTCTCAGGTAGCTAGGACTAC

28123    GCTGATTTATCTTTCTTTTCTTCTTCTTTTTTTGGGGGGTGGGGAGCGGTGTAGAGA
              CAGAGTTTCACTTTGTTGTCCAGGCTGGTCTCAAACTCCTGAGCTCAGGCAGTCCTCCCA
              TCTCAGCCTCACAAAGTGCTGGGGGTAACAGGCATGAGCCACCACGCCTGTCCTGGAATG
              TGGGGATTTCTGAGTACTAAACTAAAGCCATGCTGATAACTAAGCATAGTGAAAGTAGAC
              ATCACAATTAAGGTAGATCCTTACCAAGTTTTCCATGCTAAAATGAATCATTTTATAAT
              [T,G]
              GCTGTAAGACCTAAATTTATATAGAGCAAAGTAATTCAGTAGCATTTACCAGAACAGGTT
              TGCCATTAGGTAGTTCCTGTGACAAATGTTTACCAAATCTCAAAGAGCTTGTATAGGAAT
              GTCATTTCCTTGCCTAGAATTTCTGAATATATGGGCACACTTATATATATAGCCTTAAAA
              ATATTAATAAGGGCTTTTAATAACTTGATTCATTACCTTGATCCCATTAACTATTTTCCT
              TGATAGATCTTATGTTCCTCAAGTGGGGATTCTCTTGCCACAGAATTTGGAGAGAGAATA

28318    ACTAAACTAAAGCCATGCTGATAACTAAGCATAGTGAAAGTAGACATCACAATTAAGGTA
```

FIGURE 3, page 24 of 29

```
        GATCCTTACCAAGTTTTCCATGCTAAAATGAATCAATTTTATAATTGCTGTAAGACCTAA
        ATTTATATAGAGCAAAGTAATTCAGTAGCATTTACCAGAACAGGTTTGCCATTAGGTAGT
        TCCTGTGACAAATGTTTACCAAATCTCAAAGAGCTTGTATAGGAATGTCATTTCCTTGCC
        TAGAATTTCTGAATATATGGGCACACTTATATATATAGCCTTAAAAATATTAATAAGGGC
        [T,A]
        TTTAATAACTTGATTCATTACCTTGATCCCATTAACTATTTTCCTTGATAGATCTTATGT
        TCCTCAAGTGGGGATTCTCTTGCCACAGAATTTGGAGAGAGAATATAGTTTATTTGAGTA
        TTAAATTATGTTTAATCTCTTCTTTATTCCTACAGCTTAAAATTGGAATTATATCTATTA
        TTTTGACCAAATATATTTTAGTCTTCTTTTAGTACATGGATATTATCTTTCAAGTTCTCT
        TTTAATAAACCAGCCAAGTCTTTTTTTAACCATAAATTTCATTGAAGTTTAACAAATTCA

28598   TTAAAAATATTAATAAGGGCTTTTAATAACTTGATTCATTACCTTGATCCCATTAACTAT
        TTTCCTTGATAGATCTTATGTTCCTCAAGTGGGGATTCTCTTGCCACAGAATTTGGAGAG
        AGAATATAGTTTATTTGAGTATTAAATTATGTTTAATCTCTTCTTTATTCCTACAGCTTA
        AAATTGGAATTATATCTATTATTTTGACCAAATATATTTTAGTCTTCTTTTAGTACATGG
        ATATTATCTTTCAAGTTCTCTTTTAATAAACCAGCCAAGTCTTTTTTTAACCATAAATTT
        [-,C]
        ATTGAAGTTTAACAAATTCACACAACAGTGCACAAATCCATAAATTTTCACAAACTGTCT
        GTGTTATAAGTACCCAGCTCAAGAAATAGAACCTTAGCAGAAGCCCAGAACCTCCTTGAT
        GCCTCCTTCTGGTTACTAACCTAGGGACAATTTCCTGTCTAATACCATACATGAATTTTC
        CCTATTTTTGAATTTTAGATAAATGTAATCCATATAGAATATCCTCTTTTGTATGAGGCT
        TCTTTTATTCAACATGTTTGTGAGATCCATCTATGTTACTTGGAGTTGAGGTTTATTTAT

28630   GATTCATTACCTTGATCCCATTAACTATTTTCCTTGATAGATCTTATGTTCCTCAAGTGG
        GGATTCTCTTGCCACAGAATTTGGAGAGAGAATATAGTTTATTTGAGTATTAAATTATGT
        TTAATCTCTTCTTTATTCCTACAGCTTAAAATTGGAATTATATCTATTATTTTGACCAAA
        TATATTTTAGTCTTCTTTTAGTACATGGATATTATCTTTCAAGTTCTCTTTTAATAAACC
        AGCCAAGTCTTTTTTTAACCATAAATTTCATTGAAGTTTAACAAATTCACACAACAGTGC
        [A,C]
        CAAATCCATAAATTTTCACAAACTGTCTGTGTTATAAGTACCCAGCTCAAGAAATAGAAC
        CTTAGCAGAAGCCCAGAACCTCCTTGATGCCTCCTTCTGGTTACTAACCTAGGGACAATT
        TCCTGTCTAATACCATACATGAATTTTCCCTATTTTTGAATTTTAGATAAATGTAATCCA
        TATAGAATATCCTCTTTTGTATGAGGCTTCTTTTATTCAACATGTTTGTGAGATCCATCT
        ATGTTACTTGGAGTTGAGGTTTATTTATCCTTATTGCATAGTATCCCATTATAAGAATA

29472   AGAATAACTTTCAAAGATCATTTCAAGTCTAACAAAAAAACATAACTTTGTTCTTTAATA
        AGTGTAATATTTCCTGGAAATATGCCTGGGAATTTTTCTTGAAATAATAAGCGAATCTTG
        ACATTAATTGGACATTTTCAGAATGCCCTTTGGCGTGAAGCTATGTTTCATGTTTTAGAA
        TGCTCCTCTCTAGGTACTTTCTTTTTAACCCTGTCCAATGTACTTGACTTTTGTTTTCTC
        ACTGAGAAAATGAAAGTTCAGAATGATTTTTTTGGGGATAGTAAGGAGACTTTGCATAAT
        [T,G]
        GGAAATAATGGTCAGGGGAAAACCCTTTGTTTTATAAGGGGCCATTTTTGTATGCTTTTT
        TTACTGAAACAGAGAAGGTCAGGTTAATTCCATATCCAAATTAAATTTATGATTTTCAAA
        AGGGAAGCCTTGATAATCTAACCAAACGTGTCCATTATCTAAAGTTATTTGGAAAATTGT
        GTCACTTTAGGTGGAGGAAGCTAAACAAGAATTACAGGAAGTTGTTGAATTCTTGAAAAA
        TCCACAAAAATTTACTATTCTTGGAGGTAAACTTCCAAAAGGTAAGATATCTTTTCTTTA

30809   GTTTAGGAGGTGGAGGCGGGTGGATTACTTGAGATCAGGAGTTCGAGACCAGTCTGGTCT
        TGAACCAGGGGCCATTGGAGTTCCAACCAGCCTGGCCAACATGGTGAAACCCTGTCTCTA
        CTAAAAAAAGAAATTAGCTGGGCTTGGTGGCAGGCGCCTGTAATCCCAGCTACTCAGGAG
        GCTGAGGCAGGAGAATCGTTTGAACCTAGGAGGCAGAGGTTGCAGTGAGCCGAGATTGTT
        CCCACTGCACTCCAGTCTGGGTGACAAAGCAAGATTCTGTCTCAAAAAAAAAAAAAAAAA
        [-,A,T]
        AGGACATTTAACATACATACAAAACCATTATCAAATTTAGAGTCTATATTCAAATTTCAG
        CATTTGCTCCAATAGTATCCTTTGTAGTGTTGCCCTGATCCCTACCCACTTCCCCAGTTC
        AGGACCTAATCCAGGATCACAGGTAACATTTAGGCTTTTATTGTTTTTTTTTTTTT
        TTTCAAATGAAACAATGAAACAATTCCTTAGCCTTTTGTGAGGGAGTGGAGAGAAGAGGA
        TCTTTCATGATTTTTACAGTTGCAAAGAGTACTTGCCTAATTATTTATAGAATGTTCTCA

31106   AAATAGGACATTTAACATACATACAAAACCATTATCAAATTTAGAGTCTATATTCAAATT
        TCAGCATTTGCTCCAATAGTATCCTTTGTAGTGTTGCCCTGATCCCTACCCACTTCCCCA
        GTTCAGGACCTAATCCAGGATCACAGGTAACATTTAGGCTTTTATTGTTTTTTTTTTTTT
        TTTTTTTCAAATGAAACAATGAAACAATTCCTTAGCCTTTTGTGAGGGAGTGGAGAGAAG
        AGGATCTTTCATGATTTTTACAGTTGCAAAGAGTACTTGCCTAATTATTTATAGAATGTT
        [C,G]
        TCAGTTTAGCTTTGTCTGATGTTTTCTCATGGTTAACATGACTTTTAATGACTTCACAGT
        ATCCTTCTAATTTATGGTTGTATCACAATTTAACCATTTATATTGAATTTTTATATGGTT
        TCCAGTTTTTTTGCTATTAAGAATAGTGCTGTGTTTCATCTTAATTCAAGGCTTTGCCTG
        CATGCTTAATTATTCTTTAGAATAAATTTCTAGAAATGGAATTGCTGAGTTAAAGGATG
        ACACTCCTTTTTAATGCTTGTTTTTATGCTGCCAACTATCTCCACTGAAAATACAGCAGT
```

32031  CTTTCTAATCACAAGGAGTATTTTAAATTTGTAGAAAATTTGAGTAGTATAAATTTGTAG
AAAAATCTTCAGATACCAAGATGTAATCCACAGAAATTAATATGATTTAAACCAGTTAAG
TATAACTAAAACATGACAATACTAGGATAGTCTTAAAGCTATTTTTGAGCTTGAGCTTTC
TTTAAAATTTTTTTTATGTTAAAATGCAGCAAACATGTATGTAAAGAAGTTTTGTTGCTT
TTTAAATGTAATATGTATATTTATAAAAACATATAAATCAGGTAATTCTGTTTTTCTAAC
[G,A]
TGAAAATCTTTGGTGTTATGAAAATTTGCAAACATGGAAAACCTTGAAAGAACAGTACAA
TTAACATCCATATCCTATCCACTTAGACTCAACAATTGTTAACATTCTGTCATATTTGCT
TTCTGTGTTATGTGTGTATTTTTCCCCCTGAACATTTGAAAGAAAACTATAAACATCAAC
TACTTGACATCTAAAGACTTTCTTGTACATCACCTAAGAATAAGGACAGTGTCCTAAATA
AACATAATAACCTTATCCCACCAAAGGAAATTATGCCTATTTCCTTAATATCATGTACTC

32206  CTTTCTTTAAAATTTTTTTTATGTTAAAATGCAGCAAACATGTATGTAAAGAAGTTTTGT
TGCTTTTTAAATGTAATATGTATATTTATAAAAACATATAAATCAGGTAATTCTGTTTTT
CTAACGTGAAAATCTTTGGTGTTATGAAAATTTGCAAACATGGAAAACCTTGAAAGAACA
GTACAATTAACATCCATATCCTATCCACTTAGACTCAACAATTGTTAACATTCTGTCATA
TTTGCTTTCTGTGTTATGTGTGTATTTTTCCCCCTGAACATTTGAAAGAAAACTATAAAC
[A,G]
TCAACTACTTGACATCTAAAGACTTTCTTGTACATCACCTAAGAATAAGGACAGTGTCCT
AAATAAACATAATAACCTTATCCCACCAAAGGAAATTATGCCTATTTCCTTAATATCATG
TACTCTCAGTCTTGTTTAAATGTTTTCACCAGATGTCTCTAGAATTTTTTGTTCTTTATG
AAAAAGCATCAAATCAGGATTCACTAATTACATTTGGTTGTTTAGTCTTTTAATCTATTT
TTACATGAATTTTATCTTATTTAGTGATAAATGGGTTTATATTTTTTGCCTCAAGATTC

32711  TAATTACATTTGGTTGTTTAGTCTTTTAATCTATTTTTACATGAATTTTATCTTATTTAG
TGATAAATGGGTTTATATTTTTTTGCCTCAAGATTCTCCCTGTCATGTCTCTTGTTGATA
TGGAAACAATATTTATATAATACAGGAACATTAATTTTGGACAAGATTCTGAAGTGAACC
ATTAGCAGAGACAAGTACGGTTTGCTGTGTTTCAAAATATTGGTTATTGGTGTGACCTCA
GCCTGAAAATTATATAAATGAATAATTATTTATTTTATAGGTTCATATCGAGGGATTTTT
[T,A]
AAAAATACTTTGAATCATTCTCGTTTTCATTTTCTTTTAGGAATTCTTTTAGTTGGACCC
CCAGGGACTGGAAAGACACTTCTTGCCCGAGCTGTGGCGGGAGAAGCTGATGTTCCTTTT
TATTATGCTTCTGGATCCGAATTTGATGAGATGTTTGTGGGTGTGGGAGCCAGCCGTATC
AGAAATCTTTTTAGTACGTTTTGGTGTATCTTTGATGCAGTGCTAAATTTTGTTAAGGGA
AGTGTGTATCTTACCCTTTCTTTGCTAATTACTTTTTTCTTCCTTTTTTAATTTCTAT

33310  ATTTTTTGGGGCCTCCAGCTTTGCATGCTAATTAGTTTTGATTGATAGTTAAAATAGCCA
TTGTGGGACCTTGGTTTGGGTAACTTACTATATGAATTATCGGAAGAGCTAGTGGAAGTG
CAAGATGAAGTTGGAGGCTACCAAAAATCTCTTAGTGTTTTTCATTTTATTCATCAATT
TTGTAGTATGGAATTAAGGAGTAATTAGCTTCAAACCTGATTGTATATATTTGTATAGCT
GGAAAGAATGAATGAATGCCCAACTGTTTTGTTTTATATCATTTCTTTGGTATAGTTTTT
[T,C]
CCCCCCTGAAGATACTATTTTTAAGTCAGTAAAAAATGACGTCCTTTTCTTTCAGTGAAT
ATTTTTTGTTGGCTTTTGACAGTTGTATAGGATTTTAATATTTATCTCGTTTTGTTCAAA
AGTGTTGACTTTCTTTCAGCTTATTTGAATGTTTTTTGTTTTCTTAGGGGAAGCAAAGGC
GAATGCTCCTTGTGTTATATTTATTGATGAATTAGATTCTGTTGGTGGGAAGAGAATTGA
ATCTCCAATGCATCCATATTCAAGGCAGACCATAAATCAACTTCTTGCTGAAATGGATGG

34224  TAGTCTATTTGAAGAAATACAGTTGTTTCTACATAATTTATGACTAACTTTGAGTGTTGT
GGCAGATTTAAAGCTTACATCAATGTTCATAATATAAGAAGCAAGAGGTGATGTTGCTTT
GAAAGAAGTATCTTAAAACTCAATATAAGACATTTTGAAACCACATAGGAAGCCCAGGAG
CAAATAATTTGAATTGGTATACTTGAAAGTAATTTTTCAAAAATTAACCAGGCACCTAAG
CTTTTTATATCAGGTTATCTTTTCCTGCATAGACCAGATAATTGTGAAGGTATGTAGTCA
[G,C]
AGATGAATTGGTGGTTTATTATCAGTTTCTTTTCTTGGCTGTTATTTGATTAATGAAGCT
GGGCATGGTGGCTCACGCCTGTAATGCCAGGACTTTTGGAAGCCAAGGTGGGAGGATTGC
TTGAGGCCAGGAGTTCAAAACCAGCCTGGTCAAGATAGCAAGACCCCTATCTCTACTAAAA
ATAAAAACAGTCACCGGGCACAGTAGCTCAAGCCTATAATCCTAGCACTTTGGGAGGCTG
AGGCGGGTGTATTGCTTGAGGTCAGGAGTTCAAGACCAACCTGGCCAACATGGTGAAACC

34703  AAATAAAAACAGTCACCGGGCACAGTAGCTCAAGCCTATAATCCTAGCACTTTGGGAGGC
TGAGGCGGGTGTATTGCTTGAGGTCAGGAGTTCAAGACCAACCTGGCCAACATGGTGAAA
CCCCGTCTTTACTAAAAATATAAGAATTAGCTGGGTGTGGTGGCAGGCGCCTGTAATCCT
GGCTACTCAGGAAGCTGAGACATGAGAATTGCTTGAACCTGGGAGATGGAGGTTGCAGTG
AGCGCCATTGAACTCCAACCTGGGTGACAGTGAGACTCCATCTCCAAAAAAAAAAAAAAA
[-,A,T]
AGTGGCTTGTACCTAGAAATTGGGGAGAAAAGATTTAAAAATAAATAAAAAATAAATTAG
TCAGATATGTTGGCATGCACCTGTCATTCCAGCTACTTGAGAGGTTGAGGCAGAAGGTTC
ACTTCAACCCAGGAGTTTGAGGCAGCAGTGAGCTATGATCATACTGGTGCGCTTCAGCCT
AGGCCACAAAGCGAGTCCTAGTCTCAAAAAAAGAAAACAAACCAGTTTTGTGTAGAGCAT
TTCTACATGTGTGCTGTGCTTCAGTGTTAGTAAAAGATACTATTTTTTTTCCAATATAGT

35356  CATTAGATAAGTAAGTATTAAAAGAAGATTTTTGTGAAGTACTGTTACATGCTACAAAAT
TGTGCTAAAAGAAGTCCGTTGCAAAAGATCACATCAACACTGTATGATTCCATTTATATG
CAATATCCAGAATAAGCAAATTCACAGAGACAAATTGGGTTAGCGGTTACCAGAGGTTAG
GGAGAATGGGGAATGGCTGTCATTGGATATGGGATTTCTTTGTGGGGGATGGGAATATTC
TAAAATTAGATTGTGGTGATGGTTGTACAATTCTGAATGTATTAAAAACCACTGAAGTAT
[C,A]
CACTTTAAATTATGTGAATTACATCTCAATAAAACTTAAAATATTTATTTGTTATATGTC
ACAAAAGTTGTATGTAGAGAGGGTTTTTAAAATAAATTAACTGTAGTATTATAACTAGGT
TTAAAGTTACTATGAAAAAATTTTACTGTAGAAGTTATTCGTATTTTCATTTGATCAGTA
GTTTGTCACTGCCTAAGACTCTAGTCTAACATTCTGTACTTAGCAGTTGAGATGGATGTG
TGGTTCTCATAATAGTTTGTTGTGGAATTATTTGTTCCTGGACTGAATTACCTGCATGCT

35440  AAGATCACATCAACACTGTATGATTCCATTTATATGCAATATCCAGAATAAGCAAATTCA
CAGAGACAAATTGGGTTAGCGGTTACCAGAGGTTAGGGAGAATGGGGAATGGCTGTCATT
GGATATGGGATTTCTTTGTGGGGGATGGGAATATTCTAAAATTAGATTGTGGTGATGGTT
GTACAATTCTGAATGTATTAAAAACCACTGAAGTATCCACTTTAAATTATGTGAATTACA
TCTCAATAAAACTTAAAATATTTATTTGTTATATGTCACAAAAGTTGTATGTAGAGAGGG
[T,-]
TTTTAAAATAAATTAACTGTAGTATTATAACTAGGTTTAAAGTTACTATGAAAAAATTTT
ACTGTAGAAGTTATTCGTATTTTCATTTGATCAGTAGTTTGTCACTGCCTAAGACTCTAG
TCTAACATTCTGTACTTAGCAGTTGAGATGGATGTGTGGTTCTCATAATAGTTTGTTGTG
GAATTATTTGTTCCTGGACTGAATTACCTGCATGCTTTTGTTTCTGAGGGGTAGGCTACC
TAGGTACACACGTGTATCTAAATGAACCTTTGTTCTGCTTTCTGGTTATTGACACTGTTA

36325  CAAAACAAACATTTGTCATTTCTGTAAAGTGGTAATATACCACTCACCCTGTTTGTGGTC
CTTTCATGATACATGTATTAACATTAAAAGACCAGTTCATTTTTGTCTTTTTTTTTTCCA
TTAGTATGTTCGTTTAAAAGTCCATTCCTTAGTGTATATCCAGGAGATTCTATTGTTTTG
AACCCTGAGTCTAAAGAAAGGTTTTTTTAGAGTATTCAGACAGATAATATTTGAGGATAC
ATACATATACATACACACACACACATTTTTTTAAGATGAATGTAAAATGCAAAATAATTT
[A,T]
AAAAAGCTGCAGAAACAGTAACTCATGATATAGTCAGTGTGGGGCCAAAAGAGAAGAAAG
CAAATTATAAAACAAAACACATGGAAATTTATTACTCACTTGAGTAATAAATGAAATTAT
TAAAGCTGCAGTAGTTTCAGAGATAGCTGTATCAATTCATTAAACTATACATGTTTCCTA
TAAGGGCAGCTTTTATGTCTAAAGTATTTCCAGATGAAATTCAGAGAAAAAGTGACTAAA
CTATGGCTCAGAATAGCTAGCTATTTTCTTTTTTCCCTTGGAATGTGAGGTGTTTTTTTT

38525  GGTGGGTGGATTGCTTGAGGCTAAGAGTTCAAGGTTGGAGTGAGCTATAATAAGAATGAC
TTTAAGGAGAATGAGTTTTTTGTTTTATAATATTAATCCCATATCAGATACATTCACCTC
TCAGTATCCACTGAAGGGGTGGGGATTGGTTCCAGGACCCATGTGGATACCAAAATTCAG
GGATGCTCAAGTGTCTTTTATAAAATGGTGTACTATTTGCATATACCTACATAATTCTCC
TGTATACTTCAAATCATCTCTAGATTACTAATACAATATAAATGCTCTGTAAATAGTTGT
[T,C]
ATAATGTATTTTTTTCATTTGTATTATTTTTATTGTTCCTCTTCCCCATAGTTTTAATC
CTTATTTGGTTGAATCTATGGATGCAGAATCTGCTGATAGGAAGGGTGGAGTGTATTTGA
TTTGCAGACAAGAATGTGTTTTGTTGATTTAAATATACCTTTCTAATGGAGTATTTACTC
AATTAAATTTATCTTAGGGCCTGAAAGAAGAAGTGTGGAAATTGATAACAAAAACAAAAC
CATCACAGCATATCATGAATCTGGTCATGCCATTATTGCATATTACACAAAAGATGCAAT

39410  CTGCCTCAGTCTCCCAAAGTGCTGGGATTACAGGCGTGAGCCACCATGCCCTGCCTAATT
CTTAAATATCTAATTACTCCGCTGCCCCAAAAGGGAAAACATTATGTTTTGTAGTAACTG
ATTCAGTAGTTTCTCTAAGATTTTTATCATTTAGTACAAGTTTATCAGATCTTTCAACAT
TGTAGACATTTAAAAAATTTCTATGCACCTGGGGAGAAAACAGTCCTATTGCAGCATTAT
CCACCTATTGTTGTTGCTTTATAAAGGATGTTTTATTCTCTAATTGCTGGTTTTCATC
[A,G]
GTCCCCTGATGACCAGCTTTCAGCAACATGGTATAAAGTACTTTAGTGAGAGCTAAATGA
TAATTCTGGTTTGTATTTTTTATTTTGCCCAGTCTTACGGTGCTGAAATTCTGGTTTTT
AATGTAACTATATCAGAACTGTATCTGAATTTTTTTAAATTTTTATTTTATTTATATT
GATGGAGTCTCGCGATGTTGCCCAGGCTACTCTCAAACTCCTGGGCTCAAGTGATCCTCA
CACCTCAGCCTCCCAAAGTGCTGAGACTACAGGTATGAGCCACTGCACCCAGCCTGTATC

39603  AAAATTTCTATGCACCTGGGGAGAAAACAGTCCTATTGCAGCATTATCCACCTATTGTTG
TTGCTTTATAAAGGATGTTTTATTCTCTAATTGCTGGTTTTCATCAGTCCCCTGATGA
CCAGCTTTCAGCAACATGGTATAAAGTACTTTAGTGAGAGCTAAATGATAATTCTGGTTT
GTATTTTTTATTTTGCCCAGTCTTACGGTGCTGAAATTCTGGTTTTTAATGTAACTATA
TCAGAACTGTATCTGAATTTTTTTAAATTTTTATTTTATTTTATATTGATGGAGTCTCG
[C,T]
GATGTTGCCCAGGCTACTCTCAAACTCCTGGGCTCAAGTGATCCTCACACCTCAGCCTCC
CAAAGTGCTGAGACTACAGGTATGAGCCACTGCACCCAGCCTGTATCTGAATTTCTTTCA
TTACATTTTATTTTATTTAATTTAATTTGGTTTTATTTTATTTATTGTATTTTATTTTT
GAGATGGAGTTTCACTCTTGTTGCCCAGGCTAGAGTGCAATGGCATGATCTCAGCTCACT

FIGURE 3, page 27 of 29

```
              GCAACCTCTGTCTCCTCGCTTCAAGTGAGTCTTCTGCCTTAGCCTCCCAAGTAGTTGGGA
40056         TTTATTTTATTTATTGTATTTTATTTTTGAGATGGAGTTTCACTCTTGTTGCCCAGGCTA
              GAGTGCAATGGCATGATCTCAGCTCACTGCAACCTCTGTCTCCTGGCTTCAAGTGAGTCT
              TCTGCCCTTAGCCTCCCAAGTAGTTGGGATTATAGCCATGCACCACCATGCCTGCCTAATT
              TTGTATTTTTAGTAGAGACAGGATTTCTCCATGTTGGTCAGGCTGGTCTCGAACTCCCAA
              CCTCAGGTGATCCACCCACCTCGCCTGCCAAAGTGCTGGGATTCAGGCGTGAGCCACCGC
              [-,G,A]
              CCCAGCCTCTTTCCTTATTTTTTATCTGATTAATTTTTAATTGTCTAGGTGTCCCTGTTA
              CCTGAGAATGACAGATGGAATGAAACTAGAGCCCAGCTGCTTGCACAAATGGATGTTAGT
              ATGGGAGGAAGAGTGGCAGAGGAGCTTATATTTGGAACCGACCATATTACAACAGGTTAG
              CTTTAAAGAATGGCTTTAGTTCAAATTATATGTGGTCTTAAAGATATGTTTTAAAATGGT
              ATGTTTTATTTTATTTTAGGTGCTTCCAGTGATTTTGATAATGCCACTAAAATAGCAAA
40283         CTCGAACTCCCAACCTCAGGTGATCCACCCACCTCGCCTGCCAAAGTGCTGGGATTCAGG
              CGTGAGCCACCGCACCCAGCCTCTTTCCTTATTTTTTATCTGATTAATTTTTAATTGTCT
              AGGTGTCCCTGTTACCTGAGAATGACAGATGGAATGAAACTAGAGCCCAGCTGCTTGCAC
              AAATGGATGTTAGTATGGGAGGAAGAGTGGCAGAGGAGCTTATATTTGGAACCGACCATA
              TTACAACAGGTTAGCTTTAAAGAATGGCTTTAGTTCAAATTATATGTGGTCTTAAAGATA
              [T,C]
              GTTTTAAAATGGTATGTTTTTATTTTATTTTAGGTGCTTCCAGTGATTTTGATAATGCCA
              CTAAAATAGCAAAGCGGATGGTTACCAAATTTGGAATGAGTGAAAAGGTAATAGATTTTT
              TAAATCCTTTTCATGTATCAAATTATGTGTCAAGTGTTGATTTGAGAGCTGGTTCTGATT
              ATAAATTGGTAATATTCACTTTTTCTCTCACTCCAAATGGATTTGAGGCTCTTTATTCTG
              AACATTGTTATTCTCTGAATAAAGAAAATGGACCTTCTCTTAGCTGCTGAGAATGAGCTG
40857         CTTCTCTTAGCTGCTGAGAATGAGCTGCCCAGATAGTAACTATTACTTCACGAGTTAATT
              AAGTGATAAAGCAAGGTGAATTCCTTAGCTTTTCCATGTGGCATGAAAGAGTCTACTTTC
              TAAGTTTGGTTACTTTACTGTTTCCCTCTATTTCATATTTTCATCTTGTCATTGTTCCTT
              GAAGCACTACTATACTCTGTGAATTATGGATTTCTATATTTGAAGTAGCTGCCAAGGTTT
              TCAAGAAAGTACTGAGAACCAGACTTAAAATGATTTTAGGCTGGGCACTGTGGCTCACA
              [T,C]
              CTGTAATCCCAGCACTTTGGGAGGCTGAGGAGACTGTATTGCTTGAGCCCAGGAGTGAGT
              TCTGGACCAGCCTGGGCAACATGGCACAACCCCATCTCTAAAAAAATACAAAAATTAGCC
              AGGCTATGGTGGTGTGTGCCTGTAATCCCAGCTACTTGGGAGTCTGAGGTGGGAGGATTCT
              CTGAACCCAGGAGGTCGAGGCTACAGTGAGTCCACTGCACTCTACCTGGGTGACAGAGCA
              AGACCCTGTCTCCAAAAAAAAAAAAAAAGATTTTAAATGTTCTGTCTTGCTCATACTTTT
41705         TTTATTTTTATTTTTTTGGAGACGGAGTCTCGCTCTGTCACCTAGGCTGGAGTGCAGTG
              GCGCAATGTCAGCTTACTGCAACCACCGCCTCCTGGGTTCAAGCGATTCTCCTGCCTCAG
              CCTCCTGAGTAGCTGTGATTACAGGCACGTGCCGCTATGCCCAGCTATTTTTTGTGTTTT
              TAGAAGAAATGGCGTTTCTCCGTGTTTCCAGGCTGGTCTCGAACTCCTAACCTCAGGTGA
              TCCACCCGCCTCGGCCTCCCAAAATCCTAGGATTACAGGTGTGAGCCACTGTGCCCGGCC
              [G,A,T]
              CAAATGCAGTTTCTATTGTACTTCTTTCTTGTCCCCCGTATATTTGTTTCCTTATATAT
              AGGATAGTACTTTCTCTTTCAAATTTGTTGGTGTTTGGGGGTTTTCTGTTCAATTACTTT
              CTTCCTTTTGGTTTTAGCTTGGAGTTATGACCTACAGTGATACAGGGAAACTAAGTCCAG
              AAACCCAATCTGCCATCGAACAAGAAATAAGAATCCTTCTAAGGGTAATAATATTTTTG
              TGCTTATTTATTTTCTTAGGAACAATGTGCTTAAATAGTCAGGTTCTTAAAAAATAACAG
44325         ATTATTTCAAGGAAGTAGAGGGAATGCTTTAGAGTAGTTAAGGATACAGAAAGTTTGTAT
              GATGGAAAGGTTTAGAGAGTGTTATAGAAGAGGTGGTCTCTGCCTTCTCAGGTGTTTATT
              CTCTTTTCCTTACTATGTTATAATGCACAAATTATCTCTACTGTAGAATCAAGATTCTAC
              ATGATTTTATAAATATAAACAGATTTCATATTTTTAGGGTACATAAAGTTTTTCTTTCT
              CTTCCCATTGACTGGTTTTCGCATCCCTGCATTTGCTGCTGCTTACGTATCTCCTTTTCT
              [A,G]
              TTTCAGGACTCATATGAACGAGCAAAACATATCTTGAAAACTCATGCAAAGGAGCATAAG
              AATCTCGCAGAAGCTTTATTGACCTATGAGACTTTGGATGCCAAAGAGATTCAAATTGTT
              CTTGAGGGGAAAAAGTTGGAAGTGAGATGATAACTCTCTTGATATGGATGCTTGCTGGTT
              TTATTGCAAGAATATAAGTAGCATTGCAGTAGTCTACTTTTACAACGCTTTCCCCTCATT
              CTTGATGTGGTGTAATTGAAGGGTGTGAAATGCTTTGTCAATCATTTGTCACATTTATCC
45067         GATTTTATGTTTGGTTACTCTACTAGATTTGATAAAAATTGTGCCTTTAGCCTTCTATAT
              ACATCAGTGGAAACTTAAGATGCAGTAATTATGTTCCAGATTGACCATGAATAAAATATT
              TTTTAATCTAAATGTAGAGAAGTTGGGATTAAAAGCAGTCTCGGAAACACAGAGCCAGGA
              ATATAGCCTTTTGGCATGGTGCCATGGCTCACATCTGTAATCCCAGCACTTTGGAGGCT
              GAGGCGGGTGGATTGCTTGAGGCCAGGAGTTCGAGACCAGCCTGGCCAACGTGGTGAAAC
              [G,A]
              CTGTCTCTACTAAAATACAAAAAAATAGGGCTGGGCGCGGTTGCTCACGCCTGTAATCCC
              AGCACTTTTCAGAGGCCAAGGCGGGCAAATCACCTGAGGTCAAGAGTTTGAGACCAGCCT
              GGCCAACATGGTGAAACCCCATCTCTACTAAACATGCAAAAATTACCTGGGCATGGTGGC
```

```
          AGGTGCTTATAATCCCAGCTACTCTGGGGGCCAAGGCAGGAGAATTGCTTGAGCCTGGGA
          GATGGAGGTTGCAGTGAGCTGAGATCATGCCACTGCACTCCAGCCTGGGCAACAGAGCAA

45576     GGCCAAGGCAGGAGAATTGCTTGAGCCTGGGAGATGGAGGTTGCAGTGAGCTGAGATCAT
          GCCACTGCACTCCAGCCTGGGCAACAGAGCAAGACTCTGCCTCAAAAAAAAATTAAAATA
          AATTTAAATACAAAAAAAAATAGCCAGGTGTGGGGTGCATGCCTGGAATCCCAGCTACTT
          GAGAGGCTGAGGCACGAGAATTGCTTGAACCCAGGAGGTGGAGGTTGCAGTGAGCCAAGA
          TCACAGAAGCCACTGCACTCCAGCCTGGGTGACAGAGTGAGACTCTGTCTCAAAAAAAAA
          [A,G,T]
          TAAATAAATTATTATAACCTTTCAGAAATGCTGTGTGCATTTTCATGTTCTTTTTTTTAG
          CATTACTGTCACTCTCCCTAATGAAATGTACTTCAGAGAAGCAGTATTTTGTTAAATAAA
          TACATAACCTCATTCTGAATAATGTCCCTCATTTTGACTATAACTGTGCTTGGTTTCAAA
          AGCAAAATTAAACAAAAATCTCAGTCCCCTCCGAAGTGAACTTTGTGTTACCCTGCGTCA
          GAAATGCCAAGTTGTGTTTACTTTTCATTCAGATTTTGTGAATATGAACATGCTGTTATA

46264     TGACTTCATTAAAATTATCTACAATTTCCTAATAATTTAAGCTGTATATGGTCTTCATTG
          AAAAAAGATAGATATTGTTACAGGAAGCTTGTTACATTATATTCTTGACCTTTTGGTTGA
          TAATCTTAAATCTTAATGTAATTTCAAACTGGCAGAAATGTTGCCAGCATAATACATGGA
          TGTCTCATATACCCTGCATCCAGATTTACCAGTTGTTATCATTCTGCCCGTTTTTTATTG
          CCCCAAACCTGTTCTGTCTCCCTCTCTGTATGTACATACATACACGTATAAAATATTGAT
          [G,A]
          AAGTCTTATCTGTCTTAAATTTTTTTACATATTTGTTGAGGTATAATTTACATATGATAA
          AATTCATTTTAAATGTAGAGTTGAAAGATGTTGTGTGTGTAATCATCACCACAATTAGAT
          TTTAGAACATTTCCATCACCCAAAACATTGTCATGCAAGTGTTTGGATTAATTTTTTAAG
          AAACTTATGAACTATTTTCAAAGTGACTATAATTTTATGTTCTAACTAGCAATGTAGGAG
          GGTTATAGTTTCTCCACATCTTTTGCAGTGCTTATAGTCTGCCTTTATAATTATGGCCAT
```

Chromsome map:
Chromosome 10

FIGURE 3, page 29 of 29

SEQUENCE LISTING

<160> NUMBER OF SEQ ID NOS: 4

<210> SEQ ID NO 1
<211> LENGTH: 2488
<212> TYPE: DNA
<213> ORGANISM: Human

```
<400> SEQUENCE: 1
attttccgtt tctgggagga gtgaggggca acgggtcgga gaaaaggaa aaagaaggg       60 ctcagcgcct ccccgccggg ccgtggacag aggggcacag tttcggcagg cgggtgaggt    120
cgctgagggc ccgccggaga tgttttcctt gtcgagcacg gtgcaacccc aggttacagt    180
tcctctgagt catctcatca atgccttcca tacaccaaaa aacacttctg tttctctcag    240
tggagtgtca gtttctcaaa accagcatcg agatgtagtt cctgagcatg aggctcccag    300
cagtgagcct tcacttaact taagggacct tggattatct gaactaaaaa ttggacagat    360
tgatcagctg gtagaaaatc tacttcctgg attttgtaaa ggcaaaaaca tttcttccca    420
ttggcataca tcccatgtct ctgcacaatc cttctttgaa aataaatatg ttttcataca    480
gtctcggggt tttaaaactt tgaaatcaag gacacgacgt ctccagtcta cctccgagag    540
attagctgaa acacagaata tagcgccatc attcgtgaag gggtttcttt tgcgggacag    600
aggatcagat gttgagagtt tggacaaact catgaaaacc aaaatatac ctgaagctca     660 ccaagatgca tttaaaactg gttttgcgga aggttttctg aaagctcaag cactcacaca    720
aaaaaccaat gattccctaa ggcgaacccg tctgattctc ttcgttctgc tgctattcgg    780
catttatgga cttctaaaaa acccattttt atctgtccgc ttccggacaa caacagggct    840
tgattctgca gtagatcctg tccagatgaa aaatgtcacc tttgaacatg ttaaagggg    900 ggaggaagct aaacaagaat tacaggaagt tgttgaattc ttgaaaaatc cacaaaaatt    960
tactattctt ggaggtaaac ttccaaaagg aattctttta gttggacccc cagggactgg   1020
aaagacactt cttgcccgag ctgtggcggg agaagctgat gttcctttt attatgcttc    1080 tggatccgaa tttgatgaga tgtttgtggg tgtgggagcc agccgtatca gaaatctttt   1140
tagggaagca aaggcgaatg ctccttgtgt tatatttatt gatgaattag attctgttgg   1200
tgggaagaga attgaatctc caatgcatcc atattcaagg cagaccataa atcaacttct   1260
tgctgaaatg gatggtttta aacccaatga aggagttatc ataataggag ccacaaactt   1320
cccagaggca ttagataatg ccttaatacg tcctggtcgt tttgacatgc aagttacagt   1380
tccaaggcca gatgtaaaag gtcgaacaga aattttgaaa tggtatctca ataaaataaa   1440
gtttgatcaa tccgttgatc cagaaattat agctcgaggt actgttggct tttccggagc   1500
agagttggag aatcttgtga accaggctgc attaaaagca gctgttgatg aaaagaaat    1560 ggttaccatg aaggagctgg agttttccaa agacaaaatt ctaatggggc ctgaaagaag   1620
aagtgtggaa attgataaca aaaacaaaac catcacagca tatcatgaat ctggtcatgc   1680
cattattgca tattacacaa aagatgcaat gcctatcaac aaagctacaa tcatgccacg   1740
ggggccaaca cttggacatg tgtccctgtt acctgagaat gacagatgga atgaaactag   1800
agcccagctg cttgcacaaa tggatgttag tatgggagga gagtggcag aggagcttat    1860 atttggaacc gaccatatta aacaggtgc ttccagtgat tttgataatg ccactaaaat    1920
agcaaagcgg atggttacca aatttggaat gagtgaaaag cttggagtta tgacctacag   1980
tgatacaggg aaactaagtc cagaaccca atctgccatc gaacaagaaa taagaatcct    2040
tctaagggac tcatatgaac gagcaaaaca tatcttgaaa actcatgcaa aggagcataa   2100
gaatctcgca gaagctttat tgacctatga gactttggat gccaagagaa ttcaaattgt   2160
tcttgagggg aaaaagttgg aagtgagatg ataactctct tgatatggat gcttgctggt   2220
tttattgcaa gaatataagt agcattgcag tagtctactt ttacaacgct ttcccctcat   2280
tcttgatgtg gtgtaattga agggtgtgaa atgctttgtc aatcatttgt cacatttatc   2340
```

```
cagtttgggt tattctcatt atgacaccta ttgcaaatta gcatcccatg gcaaatatat    2400
tttgaaaaaa taaagaacta tcaggattga aaacaaaaaa aaaaaaaaaa aaaaaaaaaa    2460
ccaaaaaaaa aaaaaaaaaa aaaaaaaa                                       2488
```

<210> SEQ ID NO 2
<211> LENGTH: 683
<212> TYPE: PRT
<213> ORGANISM: Human

<400> SEQUENCE: 2

```
Met Phe Ser Leu Ser Ser Thr Val Gln Pro Gln Val Thr Val Pro Leu
 1               5                  10                  15

Ser His Leu Ile Asn Ala Phe His Thr Pro Lys Asn Thr Ser Val Ser
                20                  25                  30

Leu Ser Gly Val Ser Val Ser Gln Asn Gln His Arg Asp Val Val Pro
            35                  40                  45

Glu His Glu Ala Pro Ser Ser Glu Pro Ser Leu Asn Leu Arg Asp Leu
        50                  55                  60

Gly Leu Ser Glu Leu Lys Ile Gly Gln Ile Asp Gln Leu Val Glu Asn
65                  70                  75                  80

Leu Leu Pro Gly Phe Cys Lys Gly Lys Asn Ile Ser Ser His Trp His
                85                  90                  95

Thr Ser His Val Ser Ala Gln Ser Phe Phe Glu Asn Lys Tyr Val Phe
                100                 105                 110

Ile Gln Ser Arg Gly Phe Lys Thr Leu Lys Ser Arg Thr Arg Arg Leu
            115                 120                 125

Gln Ser Thr Ser Glu Arg Leu Ala Glu Thr Gln Asn Ile Ala Pro Ser
        130                 135                 140

Phe Val Lys Gly Phe Leu Leu Arg Asp Arg Gly Ser Asp Val Glu Ser
145                 150                 155                 160

Leu Asp Lys Leu Met Lys Thr Lys Asn Ile Pro Glu Ala His Gln Asp
                165                 170                 175

Ala Phe Lys Thr Gly Phe Ala Glu Gly Phe Leu Lys Ala Gln Ala Leu
                180                 185                 190

Thr Gln Lys Thr Asn Asp Ser Leu Arg Arg Thr Arg Leu Ile Leu Phe
            195                 200                 205

Val Leu Leu Leu Phe Gly Ile Tyr Gly Leu Leu Lys Asn Pro Phe Leu
        210                 215                 220

Ser Val Arg Phe Arg Thr Thr Gly Leu Asp Ser Ala Val Asp Pro
225                 230                 235                 240

Val Gln Met Lys Asn Val Thr Phe Glu His Val Lys Gly Val Glu Glu
                245                 250                 255

Ala Lys Gln Glu Leu Gln Glu Val Val Glu Phe Leu Lys Asn Pro Gln
                260                 265                 270

Lys Phe Thr Ile Leu Gly Gly Lys Leu Pro Lys Gly Ile Leu Leu Val
            275                 280                 285

Gly Pro Pro Gly Thr Gly Lys Thr Leu Leu Ala Arg Ala Val Ala Gly
        290                 295                 300

Glu Ala Asp Val Pro Phe Tyr Tyr Ala Ser Gly Ser Glu Phe Asp Glu
305                 310                 315                 320

Met Phe Val Gly Val Gly Ala Ser Arg Ile Arg Asn Leu Phe Arg Glu
                325                 330                 335

Ala Lys Ala Asn Ala Pro Cys Val Ile Phe Ile Asp Glu Leu Asp Ser
```

```
                    340                 345                 350
Val Gly Gly Lys Arg Ile Glu Ser Pro Met His Pro Tyr Ser Arg Gln
                355                 360                 365
Thr Ile Asn Gln Leu Leu Ala Glu Met Asp Gly Phe Lys Pro Asn Glu
            370                 375                 380
Gly Val Ile Ile Ile Gly Ala Thr Asn Phe Pro Glu Ala Leu Asp Asn
385                 390                 395                 400
Ala Leu Ile Arg Pro Gly Arg Phe Asp Met Gln Val Thr Val Pro Arg
                405                 410                 415
Pro Asp Val Lys Gly Arg Thr Glu Ile Leu Lys Trp Tyr Leu Asn Lys
                420                 425                 430
Ile Lys Phe Asp Gln Ser Val Asp Pro Glu Ile Ile Ala Arg Gly Thr
            435                 440                 445
Val Gly Phe Ser Gly Ala Glu Leu Glu Asn Leu Val Asn Gln Ala Ala
            450                 455                 460
Leu Lys Ala Ala Val Asp Gly Lys Glu Met Val Thr Met Lys Glu Leu
465                 470                 475                 480
Glu Phe Ser Lys Asp Lys Ile Leu Met Gly Pro Glu Arg Arg Ser Val
                485                 490                 495
Glu Ile Asp Asn Lys Asn Lys Thr Ile Thr Ala Tyr His Glu Ser Gly
                500                 505                 510
His Ala Ile Ile Ala Tyr Tyr Thr Lys Asp Ala Met Pro Ile Asn Lys
            515                 520                 525
Ala Thr Ile Met Pro Arg Gly Pro Thr Leu Gly His Val Ser Leu Leu
        530                 535                 540
Pro Glu Asn Asp Arg Trp Asn Glu Thr Arg Ala Gln Leu Leu Ala Gln
545                 550                 555                 560
Met Asp Val Ser Met Gly Gly Arg Val Ala Glu Glu Leu Ile Phe Gly
                565                 570                 575
Thr Asp His Ile Thr Thr Gly Ala Ser Ser Asp Phe Asp Asn Ala Thr
            580                 585                 590
Lys Ile Ala Lys Arg Met Val Thr Lys Phe Gly Met Ser Glu Lys Leu
            595                 600                 605
Gly Val Met Thr Tyr Ser Asp Thr Gly Lys Leu Ser Pro Glu Thr Gln
        610                 615                 620
Ser Ala Ile Glu Gln Glu Ile Arg Ile Leu Leu Arg Asp Ser Tyr Glu
625                 630                 635                 640
Arg Ala Lys His Ile Leu Lys Thr His Ala Lys Glu His Lys Asn Leu
                645                 650                 655
Ala Glu Ala Leu Leu Thr Tyr Glu Thr Leu Asp Ala Lys Glu Ile Gln
            660                 665                 670
Ile Val Leu Glu Gly Lys Lys Leu Glu Val Arg
        675                 680

<210> SEQ ID NO 3
<211> LENGTH: 46718
<212> TYPE: DNA
<213> ORGANISM: Human
<220> FEATURE:
<221> NAME/KEY: misc_feature
<222> LOCATION: (1)...(46718)
<223> OTHER INFORMATION: n = A,T,C or G

<400> SEQUENCE: 3
accttttgga tttagaaacc taactcgccg ggcgcggtgg ctcacgccag taatcccagc      60
```

-continued

```
actttgggag gccgaggcgg gaggaatacg aggtcaggga atcgagacca tcctggctaa    120
cacggtgaaa ccccgtctct actaaagaaa ccccgtctct actaaaaata caaaaaatca    180
gccgggcgtg gtgacgggcg cttgtagtcc cagctcgtcg ggaggccgag gcaggggaat    240
ggcgtgaacc cggggggcgg agcttgcagt gagtcgagat tgcgccactg cactccagcc    300
tgggaaacag agcaagactc cgcctcaaaa aaaataaaa aagaaaccta actcaagcca    360
gggtgagact acgaatcacg gctttggctt taagtgcctg ttgtactaag accgatgtaa    420
tcacctcggt caagtccctt tgcctttggc ctcagtttcc tcatttgcta cgctgggca    480 gggagaagag agtcaaactt tgctgttctc actgtgcatc tgagatatgg agggaagggc    540
ggaacagagg cgagacaccc gacccgaccg ctgatgtcgc cccaaaaaga agtcagctcg    600
cagggctctg gaggcttcag caagccaggc cacccagact cctcgctcca gcaacccgg     660 ggcctgccca gccggtggg gcaggaagga gggccgaagg gcctaacccc ttccttgcta    720
ctcgttgact tcctaccttt actgcataca atttgccgcc tttctgcccc agatacactt    780
tcccgaaggc gccccggcta atgggcttca ctatgctgaa ttcctcaatg gagggcggtt    840
ttggcactgc gatcctattc acgccctcct cagtcgccgc gcctcctcca ggctccttct    900
tgcttcccgc ggtgggatcc atcgctggaa agcctacagc ggccccgcgt acactgcccc    960
tccgcgagca gccattcccg ccaactgggt tcaaagtgag gctccgccca cgccgcgcgc    1020
ggccgtgacg tcaccccgcc gccgcgcccc gccctcgtca cctccctac gcagacgcgg    1080 acggaggggg gcgtcgggaa agcccgact tcgcagcctt acactcttcg tgggcggcga    1140
ccgcggcccc actgacatca ttcctcatga gggaggaggc acaaacagtt ctgggccgac    1200
cagaaaaagg acgactggga cttgactctg aatcgcagga tttgaagaga tttctcctgg    1260
cttcccaacg aggctggtgg gaagcggtcc tcctcccata cacgacctcc caccctcgcg    1320
aggcgtagaa accagttctg actgtacagt aaagcgaggg ccaggctga ggtctggaag    1380 ctaatgaaag cacagaaagt gtcgaaactg gatgagcagg aagcgagtgg cctcccctgt    1440
catctgacgt tttcccagga tgtaatttgc ctgactgaaa cagatcagga ccaacaggga    1500
gagttttcga tttagtgtga ggaaaagagc actaaattgt agcaaaagac cttattgctc    1560
aaggcccagt cagaagattt cataaggaag ctgtagaaaa tcttaagagg aaatcagccg    1620
ggcgtggtgg cggcaccctg taatcccagc tactccggag gctgaggcag gagaatcgct    1680
tgaacccggg gagcagaggt tgcagtgagc cgagatcgcg ccactgtacg ccagcctggg    1740
cgaaagaacg aaactccgtc tccaaaaaaa aaaaaaacga agaaaaagtc caaagagggt    1800
aaaggctgtt ctccccttaa aaaacagcta agaccttg ggggcgctgc tccttgtaaa     1860
tgtcaactac ttccgcggga agaacgcgc aggcacttgg ccttgtgggc gctcacttgc    1920
cccggaagta ctgttgagtt agcgcctcgc cttccgggc ggattgtctg tcgttgcagt     1980
agctgtagga aggggaggcc attttccgtt tctgggagga gtgagggca acgggtcgga    2040 gaaaaggaa aaagaaggg ctcagcgcct cccgccggg ccgtggacag aggggcacag      2100
tttcggcagg cgggtgaggt cgctgagggc ccgccggaga tgttttcctt gtcgagcacg    2160
gtgcaacccc aggtaagcca ggcattcagc ccattttttt tcctcccgcc ctgcccgtgg    2220
ctgtttgcaa attgcgctcg tggaagcgat ttctcagaag ggactctaga aatgaagtga    2280
tgtactcaat gcgaatccca ggattgagga gtggatcagg ggacgacgct gagagtgggc    2340
cggagacttc agtgctgacg atgaagctgt tgagggcaga ggcgggatgt gagctcagtg    2400
atagagagag accctggctt atcgaactga ttgcgtggaa tttctgctag aaatccgtc     2460
```

-continued

```
cggcattgtt cagtgtccgg cgttctgggg tgggaaaatg tctgtaccat acattaaagg    2520
gagcaggtaa tgttcccttt tttccgactt ccagtggct ttagtgttca cagcccctat     2580
cccctgctct ttatttcctt ttaaatggaa tttaaattta acccaaacat ggtataatat    2640
ttcggatggc cagccatgca agttttttc tcattttgac cagaagtaac taaaatgtgt     2700
atttccgagt cgtaaactgt ttgcagttaa aatttttgatt cagcctcatc ctcatcgttt   2760
tgtaaaacaa aaggtagtga agagaaaaat gatttcaagg gttttcatta cgctcttggg   2820
caatcacttg tgacaatgtt ttattcttgc ttcattccag tctcttttt tgatggtaac    2880 attttaatag attttttgag agttcctaca gttttgcaaa gaaatagttt ttaaaacatt    2940
gagttttttt aaaacataat ttttaagaaa atcgacactc ttaggttctt gatttaagca   3000
tatgattgtg ttcctttgtg taacttttac tccccctcat tttaagaatt tttaatttt   3060 tgtgctagta ctggctaaca aactgaagca gctgcttgtt attgggcatc agttatgtac   3120
caggtgagca aagcaaatgt ggaatcttct cttaatattg atatgaagta aatatgagta   3180
ggacttagca aggtgaagag tgaacaggta tcacaggcat acagaaaaat acctggaggt   3240
cctgagttag gaaagggttt agcaggttga aggaacaaaa ataaggctag tgtggctaga   3300
acatagtagt taaggggggt agtgacagaa gaggttggag aaaagacttg aggcagatca   3360
tacagggagt aaaggatata ttatggctga tttcatttta agtgtattgg gaaccattga   3420
aagttttaaa acatgattag attttcattt ttaagagatg actggctttt gctatatgga   3480
gaataggaga gggcaagagt ggaagatgtt atcagctaaa aatacccacc cacccccaa    3540 ttaaagctgt tgcagtggtt atggaaagaa gagaatgaga tatattttga agaaagtgga   3600
attgcatgag agatcagaga gatgatgggg agaggtgttt ctgggtttga tcagatgaat   3660
gcattgaagg tgctatttac caagatgaca gtgtctggag aagtcctagt aattgtttga   3720 aaagaagtc tgacatggcc tattgaatat ggtattgaag ttttttgaaac tcaactcttt    3780 gccttagttc acatcaagag gcctgatttt aggagaattt accatcaact gaatggacag   3840
ttagtagtat gtgatgttgg tagagatgat aaagggattt ttatgtaccc taggcagtct   3900
taacagggct caaatatagt gaggactctc aggcatttct tgctttgaag gatggtaaca   3960
catttggaat tccttgttgc ttaattggtt gaatacactt gaaattaaat ggtaaaaagg   4020
aagacacaga aaatgaactt tttcattgag aagagctcaa ttctaaatcc ttttgtgaaa   4080
gaaaagagat ataactaatt caaataaaag agatataact aattcaaata aatcttttca   4140
aagaggtaga aaatatgtat cttgaaatga tttgattatt tttaaagttt caaaagaagt   4200
tactgtttat ttttttttct ttttactgcc cccaggctgt aaggaactta ctgtttcttt   4260
ctgactctaa aaatgataca ttgcttcact tgactagcct taaaacaaat ccatgttttt   4320
ttgctaaaaa tgctgaaagt ataaataaga tcgcccataa tctcattact cagggatacg   4380
tatcttagac taaattcttt cacacatttt tttctataaa caaacacggg tatgcatact   4440
ttttttattt ttaattttt ttttttttta agatggagtc tcgctctgtc gcccaggctg   4500
gagtgcagtg gcgcgatctc cgctcactgc aagctccgcc tcccaggttc acgccattct   4560
cctgcctcag cctcccaagt agctgggacc acaggcgccc gccaccacgc ccggctaatt   4620
ttttgtattt ttagtagaga tggggtttca ccgtgttagc caggatggtc tccatcccct   4680
gaccttgtga tccgtccgcc tcggcctccc agagtgctgg gattacaggc gtgagccacc   4740
gcgcccccac gggtatgcat acttaaggta gttttacggt cagctttatt ccttagtatg   4800
```

-continued

```
tcacgaattt atttgtgtat caatatccat gggatgagaa gtctggaatt ttgagtcaga      4860
ttctaaatct tgttgtctt catctattaa atggtctgta cccacaataa tggcgttagt       4920
ccattgatga gggcagagcc ctcctgaact aaatgcctct aaaggtccc acctcttaac       4980 aggattacag tggcaactaa gtttgccatt gttctcaact caaacttgag ttttgaagga      5040
gataaacact ggaatttta ctggaagtgg gccctgatcc agaccccaag agagggttgt       5100
tggatctcgc acaagaattc gagagagtcg ccaggcgcgg ggactcacgc atgtaatccc      5160
agcactttgg gaggcagagg cgagcggatc acgaggtcag gagatcaaga tcctggctaa      5220
catggtgaaa ctccatctct actaaaaata caaaaaaata gctgggtgtg gtggcctgcg      5280
cctgtagtcc cagctactcg ggaggctgag gcaggagaat cactcgaacc caggaggcgg      5340
tggttgcagt gagccgagat tgcatcactg cactccagtc tgggcgacaa agcgagattc      5400
catctcaaaa aaaaaaaaaa aaaaaaagg cgagagagtc tataaagtga aagcaagttt       5460
attaagaagg taaggagta aagaatgggg tactccatag gcagaggagc tgcttgggct       5520
tgtccacgaa ggatacctac agttagttat ttcttgattt tatgctaaac aatgtgtgat      5580
tattcataag ttttcaggga aaggggacc cctaaggttc ctccccttt tagaccacat        5640 agggtaactt cttgatgttg ccatggcatt tttaaactgt catggtctgg tgggagtgtc      5700
ttttagcatg ctaatgcatt ataattagca cataatgagc agtgaggact agcagaagtc      5760
actctcctct ccatcttagt tttggtggga tttggctggc ttccttacta caacctgttt      5820
tatcatcacg gtctttatga cctgtatctt gtgcccacac cctatctcat cctgtaactt      5880
agaatgccta acctcctggg aatgcaaccc agtaggtctc agcctcattt accctcattt      5940
tgcccctact ccagatggag tcactctggt tcaaaagtct ctgacagaac tgtaacaaga      6000
agtataattg ttactcatta ttatagctgt ttgaggatta aatgggatga tagaagtaaa      6060
gcctgtagta ctaaacctgg tatataataa gaacccattt aatgtattca tttactcaac      6120
aaatatttat taagtaaatt ttttttttc ttgagacagg gtcttgccat gtcattcagg       6180
ctggagtgtg gtggcatgat agctcactgc agcttcaact tcctgggctc aagtgttttt      6240
tttgttttca ttttattta tttatttatt ttgagatgga gttttgctct tgtcacccag       6300
gctggaatgc aatggcatga tcttggctca ctgcaacctc cgcctcccag gttcgagtga      6360
ttctcctgcc tctgcctccc aagtatctgg gattacaggc gcccacacc attcctggcc       6420 aatttttttg tatttttagt ggcgatggga tttcaccacg ttggccaggc tggtctcgaa      6480
ctcctgacct caggtatcta cctgccttgg cctcccaaag tgctgggatt acaggcatga      6540
gccaccattc ccgcctact tactatttt ttttttta atgttggatg tatttcattc          6600
tgtggtagtt tccttttttt tttttttt tttttttga gagacaggtc tcaccctgtt         6660
gccctggcta gagtgcagtg gcatgatcac agctcactgc aacttccgcc tcctgagatc      6720
aagcaattct tctaccacag cctcccaagt agctgagact acaggcgcac accatcacac      6780
ccatctaatt gttgtatttt ttggtagaga tggggtttca ctgtgttggt caggctggtc      6840
ttgaactcct gacctcaagt gatccaccca cctcggtctc ccaaagtgct ggggttacag      6900
gcgtgagcca ctgcactcga ccagtggtat catttgtttt gccgctcccc taatgctgga      6960
tgtttccagc tttctactat ttttttaaatg tttcaatgag agttgttctc tatgcatgtg     7020
caagtacttg tcagattatt tccttataat aaattcctag aaggtggatt gctacaaaca      7080
agaaatgtat gtatttttga tactttttgat ttacatattc agaataatat cctgaaagaa     7140
cataccagtt ttcgtctcac cagcagtaaa tctgagtact tacagttttt agtatacaga      7200
```

-continued

```
gttgatatat aatgtacctt taactcttaa caaatcctga caaaaaaagg agattgttct    7260
gtttatttaa aaaaaaacta cttaattttt aacttttatc ttttttctagg ttacagttcc    7320 tctgagtcat ctcatcaatg ccttccatac accaaaaaac acttctgttt ctctcagtgg    7380
agtgtcagtt tctcaaaacc agcatcgaga tgtagttcct gagcatgagg ctcccagcag    7440
tgaggtaagt ctttatcctg gttgtgtgag aaagcctttt tgatatacag ttgaccctta    7500
aacaaatgaa ggattaagga tattgtccct cccccgtagt caaaaatttg agtataattt    7560
ttgactcctg agaaacttaa ctactaatac cctactattg accaggaagc cttgccgata    7620
aaataaaggg tccattaaca tatattttgt atattttatg tattgtgtac tgtattctta    7680
caataaagta agatggagaa aatgttatta agaaaatcat aaggaagaga aaatatattt    7740
accattcatt aagtagaagt ggaccatcat aaagatcttc attatcttca agttgagtgg    7800
gctgaggagg aagaggaggg gttggttttt ctgtctctgg tggcagagac cggagaaagt    7860
ccacgtatct gtggatctgt gcagctttaa tctgtgttgt tcaaggatca cctgaggtca    7920
ggagttcaag actagcctga ccaatatggt gaaatcccat ctctactaga aatacaaaaa    7980
ttagccgggt gtggtggcgt gcgcctgtag tcccagctac tcaggaggct gagacaagag    8040
aatagcttga gcctaggagg cagaggtcgc gtgagccaa gatcgcacca ctgcactcca    8100
gcctgggtga caacaagact ctgtctcaaa aataaataaa taaataaata aatataaaaa    8160
tgtaatctca tttttttggtt taatctaaaa aaaaacacct gttttttacag ggaagtggaa    8220 taggtaggga tttaagaagt aaataaaact cttaaaaaaa taaaggacca gcagatttag    8280
ggagcagctc atacttctag ggctgagata gagtcaggaa gagttctcca tccccagggc    8340
tgagatcctg acattgttgg cgaaggcatg gccttggctc actgaatggt agaaaagttg    8400
ctgtgatgtc atgccagggt aacgtgctag aaatctggga agtctgccct ctaggatact    8460
gggaaaagct gttcctgggg atgtgtccta ctagagaagc tgttacacga gtggtgccag    8520
gggaagctgc taggtcctgc tggccattgt gcacgccagg agccagggtt tggtgaaact    8580
gcacaattga caggagccag atgctataga aaccacgggt gttacagaca ggaacttgct    8640
aaatgagcat accacaacca ggaatcaaaa cctctcttcc tacagtgtat gttcagtgac    8700
ttcctgacga agcttaacat tgtttcaatt ggcaaaggaa aaatattcga agggtacaga    8760
tccatgttca tggagccagc aaaaaggatg aagaagagct tggacacaac cgataactgg    8820
cacatccgtc cagaaccctt ctccctctca atccctgtac actgcgggtt tctccaaatg    8880
cctattgtct atgatttgtt ttgtccatcg ttcttagtca cggcttagtt caggttcttg    8940
ccatctttca cttgttccat cagccttctc tctcatccag tctagttgct ttgtttgttt    9000
gttttatcat ttttaaattt tttgtaaaga cagggtcttg ctttcttcac caggctgatc    9060
tcgaactcct ggcctgaagc agtcctccca cctcagcctc tcaaaagtgt tgggattaca    9120
ggctcgagcc accatgctag gccagtctat cttccttagt tctccatttt cttctataag    9180
acagaactaa tcatgttact tagagaatta aattcaaaca tggctcttca cagtttggcc    9240
ataacctatc tctttaattt tttctttcct tgaattttttt gagatattcc agacccttgg    9300
atggcttttt gtttgcccccc gtccctaagc cgccttgatc attttttaata gcttaaaaag    9360 tactttaag tattttatt catcatgcct ttaactgtct tttactatgt gctgtcatgt    9420
tgtatgctag gatacgtaga tgagtaaggc atgatctctg cctttgatcc ttactattag    9480
gaaataaggt gtatttatta gttatgttag tattgagaaa atgaattcta agaatatgag    9540
```

```
ttatagctaa tttaaaaagt accgtattcc cagacatcag tccagagcta tataatccgt   9600
gtccatgcct cttttaaaaa aaactttatt tttagagaca gggtctcccc tttgtagccc   9660
aggctgaagt gcagtgatgc tgtcatagct cactgcaacc tccagctcct gggctcaaac   9720
atttctcctg agtagctggt gctgcggtg cataccacca tgcccagcta atttttaaat    9780
ttttcatcaa gatgatgtct taccatgttg ctcaggctgg tctcaaactc ctggcctcaa   9840
acgatcttcc caccttagct gttttgggtt tgagtaacat gtaattgtta cttgccttta   9900
agtgcctctc tttcagctca tgtggacaag aaaataatcc ctatcctgtt gtttaaaagt   9960
gggtatacac acatttttgt gatttttaga cttttttgcc tgattttcac acagttttga  10020
ctttaatttt cttctttatt agaagatatg ggtaacttta gaacctctga gttcaaggaa  10080
ggatctaagc aatgaggcca gaggagtgag atgtcctatg gtaaccaagc ataccatttc  10140
tttgtcaagt gggcttttgt ttatggctgc ttagggctt aaaagctcca tggactggtg    10200
aggattatca tttgaatgga atttccccaa ttcaagaacc ttactattat cctccaatca  10260
gttctacact gttggggaaa atcccctggg ccttatataa catactttgt aaccctgcag  10320
ttagttactc ttacactctt gtcattataa atgcttgatc aatagttgat agactagctc  10380
ttgatcagag taccctttgta tggagagaag gaaaaaatgc catacatttc acttgattct  10440
gtgaaccata atgcttagga cagtagtggt ttgggtttga tttaaaaaaa aaaagttttt  10500
tctcattcat gctgaaatgt catctcttta tttaaggata ccattaggaa tataatttt   10560
taacctatgt caaacctcat atgactgatc tcagtaaaac gaactgtgaa atatttgca   10620
tcaatttatt tttaaatatt aaaaaaagga aatatatttg ttagactttt aaaatctgat  10680
tgttttaact gataatatgt actccttagg ttaaatatct tgataatatt aatgcatacc  10740
tggttgaccc aatctttac agccttcact taacttaagg gaccttggat tatctgaact    10800
aaaaattgga cagattgatc agctggtaga aaatctactt cctggatttt gtaaaggcaa  10860
aaacatttct tcccattggc atacatccca tgtctctgca caatccttct ttgaaaataa  10920
atatggtatg ttaatgtgtt ttttgttcca attaaatatt ttagcactat taataattat   10980
agataccatt tcttagcttt cacagtagcg tttattgtgg gctgggttct ttcctgaagt  11040
gttttttttt ttgtttttttt ttttgcaatt tttcatattg aaatagtacc agatttacag  11100
gaaagttgca aagatagtac agaattttgc ttccactaat tttggcatct tacataatca  11160
tgttacattt gttaaaacta ggaaattaac attggtacaa taatttttt tttgagacgg    11220
agtctccttc tgtcagccag gctggagtgc agtggcacaa tctccgctca ctgcaagctc  11280
cgcctcccgc gttcacacca ttctcttgcc tcggcctccc aagtagctgg gactacaggc  11340
gcccgccacc acgcccggct aatttttttgt attttagta gagatggggt ttcaccgtgt   11400
tagccaggat gatcttgatc tcctgacctc gtgatccacc ctcctcagcc tcccaaagtg  11460
ctgggattat aggcgtgagc caccgtgcag gcctaacatt ggtaccttat ttttaactaa  11520
actacagact atttgaattt caacaaaatt tgttttcacc aaatcactag ttctctgcaa  11580
gtgtcctttt tcttttccag gatctgatcc agcataccac attgcattta gcagaatggg  11640
ggggcggtgt ttgtttttaat tttaggtgac acacatttaa ttccaggaaa catacttaat  11700
ctttgagaat acattgatta aaaaaacagt tgttatccct tttgtggaat gtctacattt  11760
tttttttactt gaatctcata acagtatggt agtataataa gtgggttcat actagtctga  11820
aaagggatgt caacttatg agtttttctt tggatggcac ttaaacaggc cataaaaatc   11880
caggaacaaa atagcaggtt tgactagttt ataatgaagg tttgatttga agctgtcctt   11940
```

```
tgcataaact taattcatta attcttgacc cttcctttgc ctttatttca gtgtaagggc   12000
ataaaaaacc gtaagtgtga ggaaaaaatg aaatggtttt gagcttgggg cttagacta    12060 aaagtttgcc tctgcctaaa gttgccttct tataaaatat ttggcccata ccaagtgttc   12120
aatagaataa aattctttt gttactatgt tattatgatt attcctactg ctcttctagt    12180
ctgcatattt acatttactc ttaagattgt tcctcatacc accagctgct tgctaggttt   12240
aggcaggcag aggtattagg aagagatttt ttgactggat gctaagggac cttgaaaaaa   12300
gtccctaaat tctaactgag acacacaaat agatgatagc cactgtttgt ttctgctgtt   12360
gctgctgatg accttttccc taggatcttg gatataaaat aggatgagac acactagtca   12420
agagaagcag ttaggaagga tcagtgaagt attcatggct tgacctttct ttttacccaa   12480
tgactaggga agctttatga gggaaagata atagtagcta tgattcacag tgttttatta   12540
taccattaga gcttttgaaa ttgtctctaa gaaacagcag ttctttatct ctttatgttc   12600
ttaactaaaa gtaattttag cctaaacaca gtacatcttt tttttttttt tttttaaaga   12660
gacgagtctt gctgtgttgc ccaggctgga gtgcagtggg gcaatctcgg ctcactgtaa   12720
gctctgcctt cccagttcac gccattctcc tgcctcagcc tcccgagcag ctgggactac   12780
acgcatccgc caccacgccc ggctaatttt tgtattttta gtagagacga ggtttcacca   12840
tgttagccag gatggtctgt atctcctgac ctcgtgatcc gcccgcctca gcctcccaaa   12900
gtgctgggat tacaggcgtg aggcaccgcg cctggcctta aacacagtac atcttttatc   12960
actggttttg ttttgttttg tttttgagac tgagtttcac tcttgttgcc caggcgggag   13020
tgcaatggcg cgatctcagc tcaccacaac ttctccctcc cgggttcaag tgattctcct   13080
gnnnnnnnnn nnnnnnnnn nnnnnnnnnn nnnnnnnnnn nnnnnnnnnn nnnnnnnnnn    13140
nnnnnnnnnn nnnnnnnnnn nnnnnnnnnn nnnnnnnnnn nnnnnnnnnn nnnnnnnnnn   13200
nnnnnnnnnn nnacgccact gcactctagc ctgggcgaca gagcaaaact ccatctcaaa   13260
aaacaacaac aaaacaaaca aaaaggcaa gacccggcca ggcgcggtga cttcgcctg    13320 taatcccagc actttgggag gccgaggagg gtggatcacg aggtcaggaa atcgagacca   13380
tcttgactaa cagtgaaacc ctgtctctac taaaaataca aaaaattagc tgggcgtggt   13440
ggccggcgcc tgtagccagt cccagctact cgggaggctg aggcaggaga atggcgtgaa   13500
cccgggaggc ggagcttgcg gtgagccgag gtcgtgccac tgcactccag cctgggcgac   13560
agagcgggac tccgtctcaa aaaacaata aataataaa aataatgtaa ccaacaagtg    13620
atagctagta aatggaagaa ctgtgagatg tagttaaatt agcgatgctt tagatatttt   13680
cataaaagca gtcatatcat ggataaataa aagttgaaac tcatattgtg atttccctaa   13740
tatttgatag aattatttat atttcatagg attttgttt tttggtttgg aaattagaaa    13800
atttactttt tgcaatttcc ctccaggtaa cttagatata tttagtacat tacgttcctc   13860
ttgcttgtat cgacatcatt caagagctct tcaaagcatt tgttcagatc ttcagtactg   13920
gccaggtatg aagcaacaac cataaattgt ggaaaaaaa atatttattt actatagtct    13980
gatttgtctt tcttaatggt attaattcta aacattcatt tgcaattcac aggacctaaa   14040
gagtatttgg aattaatgag tttgggtact tctgtataat ttttaatctg gaaaatatat   14100
aggagctaaa ttttgagcgt gatagtgcca caataaatca aactccaggg aacttatcta   14160
cgcttgtttc aagataaatg actaaccaca tttgcttact catcctcact ttcaaaagcc   14220
cattgaaatt aattttatat atatatat gagaaaaaaa gagcaacaac agaagcgttc    14280
```

-continued

| | |
|---|---|
| cgttaacgga cgagaaattt gagggctttc agtaagttgt aaaataagtg acatcaaatt | 14340 |
| gacagtaaaa tcaaatttgc atttattcat ataattttg aatacaaggc actagtgata | 14400 |
| gatgtcaggt gatagtgatc actgtaaatg aaaaagacat gttttctacc ttcatgggac | 14460 |
| taatggtgtc atgaaagagg tgggtacttc tgtttccagt agtagaactc aggaaaaacc | 14520 |
| ccacttccag agccagtaaa attgggcact gggatgggat ggaataaaca gttgaagatt | 14580 |
| gccagaaatg ggccaatcac agtgcagata tggcctttaa cctttagata aattagcaaa | 14640 |
| aaacacctt ctaataagac gtctgtgtgt gtgtgtgtgt gtgtgtgtgt gtgtgtgtgt | 14700 |
| gtgtgtgtcg agggacatct gtctgtggag actcctggtt tgagcattga tgccaaggaa | 14760 |
| agaaagaagc tagcacccca gattactttg gttttgaatt acacattcgc taaagtattc | 14820 |
| tgctcattta gcatagtcca tgttttatat tctaagtata tttacttttg ctagtgttga | 14880 |
| ggatacccat ttgtagtcaa tactgatgac tgtatttgtt ttgttttgtt ttgttttga | 14940 |
| gatggagttt tcctcttgtg acccaggctg gagtgcagtg gcacttcctg ggttcaagca | 15000 |
| attctcctgc ctcagcctcc tgaggagctg ggattacagg ttcccaccac caggcccagc | 15060 |
| taattttgt attttagta gagacggggt ttcaccatgt tggccgggct ggtctcagaa | 15120 |
| ctcctgacct taggtgatcc gcctgccttg gccttctaaa gtgttgggat gacagcatga | 15180 |
| gccacggtgc caggccctga tcactgtatt cttatttata aatacaaatg gattaccaag | 15240 |
| aatccacata tttgaggaaa acttaaagca taaagagag gcaccaattt cagcaaagag | 15300 |
| actaataacc ctctaaagaa atagttaatg cagaagacag aagaagacag ctgatacgtt | 15360 |
| tttagctatt gttggaagat gtataaaaac tgagcgtgtg ttacctaggg tatgaaaact | 15420 |
| atcttaataa attttcctaa tgttgtaact ctgaggttag attctctcaa tgtcagaaaa | 15480 |
| taaagataaa aatccagtaa cagaaaagac agcttaaaaa aatacctaaa tacggccagg | 15540 |
| cacagtggct tatgcctgta atcccagcac tttggtaggc cgaggagggt ggatcacaag | 15600 |
| gtcagaagtt caagaccagc ctggccaaca tagtgaaacc ccatctctac taaaaataca | 15660 |
| aaaattagcc aggcatggtg gcgtgtgcct gtaatcccag ctacttggga ggctgaggca | 15720 |
| ggagaatcac ttgaacccag gaggcggagg ttgcagtgag ccgagaccgc gccactgaac | 15780 |
| tccagcctgg caacagagcg agactccgtc tcaaaaaaca aaaagacaa aaaaacccta | 15840 |
| aatacttgaa attttaaaa cccttttcta aatgtctcac gactgaatgg aaataaaacc | 15900 |
| gggattacag acactcagta atgaaccaca gtgaaaatct gtatatcaga ctcttggtga | 15960 |
| ggacaaaatg acattgaggg cgttatataa tttactgaga aatcaggctg gatgcagtgg | 16020 |
| cttatgcctg taatcccagc actttgggag gctgagtcag gtggatcacc tgaggtcggg | 16080 |
| agttcaagac cagcatggcc aacatggtaa aaccccgttc tccactaaaa aagaaataca | 16140 |
| aaattagcca ggtgtggtgg cacatgcctg taatctcagc tactcgggag gctgaggcag | 16200 |
| gataatcgct tgaacctggg agatggaagt ttcagtgagc caagatggca cctccatcct | 16260 |
| gggcaacaga gcaagacttt gtctcaaaaa gaaaaaaaaa tttaagacat aaagatagaa | 16320 |
| aataaattga atttctgaaa aataatagaa gaattaata cacacaaagc aaacatttta | 16380 |
| aaataatagg tggaaatagt tttaattaaa ccaaaaacaa atttagtata aaaaaggaa | 16440 |
| caatttaaca attctgatta agaaacaaca ggaaaataca gacagtatta gaagtatgag | 16500 |
| tgggaattgc catggatatg tgaaggtttt aaaattgcaa ggtagtatgt gtaacttat | 16560 |
| gtcataaata aaaatatgtt gaaatggaca attgtctaag caattaatta acaaagttaa | 16620 |
| cccaagaaga gataggataa taaccatgaa gtttaaaaga cagtatttta aaatatgtgt | 16680 |

-continued

```
ccctttgccc cagaggcact aggttcagat aatttttatg gctgcattct tctagaatct    16740
tgagtttctt tttaatttaa aaccttatta aaaagaaaaa gatagagttc cctatttatt    16800
ccatgagatt gctgttagta aaacttttta gtattagcat aaggccaggc actgtggatc    16860
acacctgtaa tcccaacact tgggatgat cgcttgaagc caggagttca aaacaagccc     16920
agacatcatc tcaacaacag caacaaaaat tagcccgtcg tggtatcatg ccctgtagt     16980
tctggatact tgggaggctg aggtgaaagg tttgcttgag cccaaagttc aaggttacag    17040
tgagctatga tcatgccacc gtacttcagc ttgagtgaca gcaagatcct atctaaaaaa    17100
tatatatatg tatatatgta tgtatctgtg tctgaatgta tatacacacg caagcacgac    17160
agaggaacaa aatagatgtg tttcacttaa cagaaatcct aaataaaatc tgaagaaagc    17220
aaatctagaa atgtgctaaa aatattatat catgattaag gaatacaaaa gtgatttaag    17280
attattagta agtcaatta tcatattgat tagaaaagaa aaatatcatt atttcaatgt     17340
atgataaaaa gacatgatat attttaattg ctgtgcttcc tgaaaactct tagaaagtta    17400
gaaatggaag gaaacttaaa atttattaaa catctattat gttcctgtta atttgagaaa    17460
catggagtat cctggttttt ttttcagcat taatttggag attctgaaca atatgattta    17520
aaagaaaacg aaatgagcca tatgtaagtc aaagaagga gtaaaattat aatttgcagg     17580
tgataacgat tgtttaccag aaaattcaag aaaatcatcc aaaggctgt tgaaataaag     17640
agttcactgc attgtccata ccagataaat gcataaaaat caatagcttt cttatattct    17700
agcggcaggt tttatttaca atttctttaa aacccagtaa atgttttatc ctgacaggaa    17760
atatacaaca tacatatata cacacataca cacgtgtgtg tatgaagctt tactgaagga    17820
aatgaaagag gaactgagtg aaataaaata aggccataat cctatttgga agaactaggt    17880
attacaacag tatcaattta catccaaatt tgtaaagtca atacaacccc aatcaaaact    17940
ctaatgaccc acttgggaaa tcgagaagtt gattttaaac ttaatttgga ataactgagt    18000
acatgttaaa agaatactaa tgaaggggat tttatcctac ttaagtacat gaaaatacag    18060
atatttagcc atggaaatca gtagtgtagt attacaaata actaaaatta aaaaatttaa    18120
cctagtgctg acatacatca gtgcaacaaa attaagaatt ttgaatcaat aagcaaatga    18180
tggattatca aatgttatca gcctaagtgg ctgttttgga aaaatcaagt tcttttctta    18240
catcatacca aaaaaaaaag ttccaaatat gttaaagggt tgaaaacaaa aatataaaac    18300
tgaaaatatt agaagtaagt agactacctt taaaatctta gtttggcaat gaaactctaa    18360
tcaagttaaa atgcagaaaa cacagcaaag gtatggctgc actgagctaa taaattactg    18420
tatatgatcg aaagacaaag acacattaaa ataaatgttt acagtatata taactaaaga    18480
ttactatctg taacatccat attatctaaa taaaaatgga aaaatgtgca aaggacatgc    18540
atggtcaatt tactaaagaa ataaaaataa aaatagtcaa taaaaataca gaggaagctt    18600
ttcaaaattt tcccacactt gtaatctggg aaatgcaaag taaaacaagg tactgttatt    18660
tttgcccgtc agacttgcac aaatttaaaa gattcatatt atttagtgtc ggcaaggata    18720
tgaagaaaag gaaactcata agcattggtg ggcacataaa ttgataacag cctttttag     18780
aaagtagtct cttagtgtca aacaaatttt aaaccttaac agtgtttctt tcaggaattc    18840
agtctacatc tgctgacata catgtataag aatgttcacc acagtattgt ttccagcaat    18900
aaaaaccaga aaacaaataa tgttcaggga aatggttgaa tgaattgcac tgtgataaat    18960
tggaaaagtg taaacagcca ttaaactgaa tgcactgttc tgttctgaaa aatatgcacg    19020
```

```
aaaaatgaaa attgcaaaaa attaggtact atttctagag tagttttat agaaagagca    19080
cctgtgtgca tgcatacaag ggtagtcaga attgttaaca ggttatactt ctgggaagtg    19140
ggattggggc ttgagaaatt agaagacact aatttgatac acttacccct ttttcaaaaa    19200
cattatgtaa ttaccaaaaa catgtaaaaa tcagttgtgt agattcaatc tattttaatt    19260
acttggttgg gtttttttt tttttgaaat cacagtttat cagagttgat actcagtttt    19320
ttaaattata ctgtataacc ctctgacttc tctatttacc tttatcccct atcaacataa    19380
aaaataggcc aggcgtggtg gctcacgcct ataatcccag cactgtggga ggccaaggca    19440
ggtggatcac ctgaggttag gaggctgagg caggatagtt gcttgaaccc aggaggcgga    19500
ggttgcagtg agcagcaatg ccttgcactc cagcctgggc aacaagagtg aaactccatc    19560
tcaaataaat aaataaataa ataaataaat aaagttcctt ttgaaaaaag gaggatagaa    19620
aaaactataa gctgggcatg atagatttaa gttctcagac ctaatcccag ctctttggga    19680
ggctgaggca agaggactgc ttgagcccag gagttcaagg ccagcctggg caataaaagg    19740
agacccgtc tctacaaaaa agaaggaaac aaaggaaaat gtattgaagt gtcaggcaaa    19800
ttagatagac taggatatac aggtagggtg tcagacttta gaatcttagg cattttcctt    19860
ttcctgtaac aatttatagt gacagtgaat ggtattgttt tatttagttt tcatacagtc    19920
tcggggtttt aaaactttga aatcaaggac acgacgtctc cagtctacct ccgagagatt    19980
agctgaaaca cagaatatag cgccatcatt cgtgaaggta attagacctt tttatgatcc    20040
aaaaagcaaa tattttcaag ttgttagagt gaggagcttc aatatctgat ttcttttgtt    20100
ggctgataga tattcttcct tctttccact aataataagg gattagtaac ctgtgtaatc    20160
attataccctc taactcttct gggcaccaga cttgcctctc cacttactag atttttttcc    20220
cacaaaccta cacctgtcga ggtgttctct gtattaatga gcagcatcca cccaagctaa    20280
aaacctggct atcaacctac gtttgtccat gttgccttac ctcccacatc cattaaccac    20340
taaagtcctg ttgatccaac ctcctaaata tttcttacat ctgttccact gccatagata    20400
ggctataact atttgttgcc taaattactg taatgaatac ttgtttagtc tccttgcctc    20460
tagtcttgct gcgttcagtc cagcctccag actgccaccc atcaatcttt ctaaaataat    20520
gatctagtta tattactctg ctttattgct tacctccacc tgatacactg ggaatttcat    20580
catttgatct ctacctgcca tgtttctctt ctcaccattc aatatgcccc tctgtttccc    20640
tgctcctctc ttggcattga agtcttatat aagattgctt acagttcttg agcactgaag    20700
gctattgatt catgcctccg tcagattgtt catagtgttt attccctgtg ttttagatgt    20760
cctattctct gtaaggcctt ttccatattc ctgaggtagc attgatttac caccatacat    20820
aatacttcta acataatatc aaaatgattt aagaaactta gttatttata tatcttttc    20880
cagtagactg aaaactttaa gatcagtggt ttatttatct ttacatcttc agaacttata    20940
taaggccaag tatatgaacg gtgcttagta gacatttagt aaattaatga gatttttttcc    21000
tctagcaaag ataaagggat aagaacatta agccaatcaa accctaaaat aatatgtgac    21060
ctgttttcag tgtagtgttc gtgcagagaa taatgccact ttctttatat tattaattga    21120
ttgatgcagg aatgggatct agtgttagtt tcctagttat tgattaattc attgctgagt    21180
cttaatctgt ttcttcacat tgacagtaaa aattatacag aattttagtg aattttttg     21240
agtggtcaca atattgttgg gaagtatcac tgtgttgtta accagtactg atgtgttgtt    21300
tgtgtattca ggggtttctt ttgcgggaca gaggatcaga tgttgagagt ttggacaaac    21360
tcatgaaaac caaaaatata cctgaagctc accaagatgc atttaaaact ggttttgcgg    21420
```

```
aaggttttct gaaagctcaa gcactcacac aaaaaaccaa tggtaagttg aattgacacc   21480
atccgtgttt gagaagagta actgaaagga agtcatagtc ctacatttaa gttttaagta   21540
acttttctaa gaccatctat tgattaaatt ccactatatt tgtaacttaa tctatgtaga   21600
aatggcgata ctgctgatgg tttccctttc tcaagagaga aaacaaattg gagaacagga   21660
agtgtgaatg gcttcataaa ggttttgtt tctttatttt ttgtttgtgt ttgttttga    21720 gacacggtct tgcttcattg cctaagccag agtgcagtgg tgcaatcatg gctcattgta   21780
gccttaactt tctgggctca agtgatcctc tcacctcagc ctcctgagta gctaggatca   21840
caggcatgtg ccaccacgcc cagctaattt ttgtggagat ggaatcttgc cctgttgtcc   21900
aggctggtct tgaactccag ggatcaagtg atcctcctgc cttgacctct aaaatgcta    21960 ggattacagg catgagccac catgcttggc cttaagtttt tgataatagg gtacttacag   22020
gaaatcatag cagttgtgag aaagaatgcc agattccaaa attggatgtg atgaaatatg   22080
attattaaca ataacctaat atttgcattt cattgagctg tcatatttca taaatgtgat   22140
ttcatgtaaa gcttttctt tctctcctag attccctaag gcgaacccgt ctgattctct    22200
tcgttctgct gctattcggc atttatggac ttctaaaaaa cccattttta tctggtaaaa   22260 gctttttta tttgtctaac ttatttctta ttcctttaaa tacatgattc cttttaatgc    22320
ctaatctaac ccttaaagaa agaacatatt aatgtttaca gtactagaat taggctttca   22380
ttcctagtag tggttagttt cccagatttt tagaaaatga tacctgtcca attataaaat   22440
ttaaaaatta tcctggtcaa cagggtgaaa ggaaaattaa ttaattaatt ttaaaattat   22500
gtagaagaat tttataatgg caatacaagc tgaaatagtc ttctatttca aagataaaca   22560
aattcagttt attcataaaa tcacattaaa tgtttccctt ttttttagtt tgcttatctg   22620
aaattaagca atagtgtcag acttacgtgg ttccaattac cttttccact actgtgcagt   22680
tttcaccctg tgttgcctat tctcttaaat attaaggata tgtacagatt cttaaaaaat   22740
actttgtggg ccaaaactat tggtgttcat tctagaatta ctattttaaa tttgttttcc   22800
cagcttctat gttcctgatt tattaagcat ttctccttaa ccccatattt tgccagctca   22860
tttttcagcc tatcttaaca gtattttggg cttcttctga ggaaattaga aattgctcaa   22920
tttactcatt tataactgct ctagtttgga agtttctacc tgagtgggaa agacttaaga   22980
aatccttgta atagttctcc aaaattgatc tcaaatattt tactctccct atcgagactt    23040
ttctgtcttg cttgtcagac ttaatgttgt cataattgat aggtcatttg agggcaagta   23100
ataacagttg tcagaggaag aagactacat gaaaagtata ataatgtgtt aagcctcaat   23160
tttttattaa tgtgtgtcaa tgttttctgc taactttaag gcaatgtgtt tcaaagtgta   23220
gacctgtgac caattagaat aattgaagtg tttgttaaaa atgaaaattc tcctgggccc   23280
tgtgctgtgg cctgagaatt aacatacttc tcaagtgagt tttattcaca ccaaagtttg   23340
agaaactttg atttaagatt tctatcatta gatactacaa taagaagtag aaaataattt   23400
ttgattttat taactgaaaa gtacaaatag gtcattttat tttattttt tatttttatt    23460 catttatttt ttttgagatg gagtctcgct ctgttgccca ggctggagtg cagtggggca   23520
atcttggctc gctgcaacct cctcctcctg gggttcaagc aatttcactg cctcagcctc   23580
ccgagtagct gggactacag gcttgcgcca ccatgcccag ctaattttt gtgttttag    23640 tagagacggc gtttcaccgt tagccaagat ggtctcgatc tcctcacctt gcgatctgcc   23700
cgcctcagcc tcccaaagtg ctgggattac aggtgtgagc caccacgccc agtctttatt   23760
```

```
attttttatt ttttccaagt ttattaagaa agtaaaggaa taaagaatg gctactccat    23820 aggcagagca gccgaaannn nnnnnnnnnn nnnnnnnnnn nnnnnnnnnn nnnnnnnnnn    23880
nnnnnnncaa caacactaaa caaccaccta ccagacaaac acaatgaaag cgcaaactcc    23940 gacccccaa ctcaatcaac acatacaaaa aagatgctct accatcatac caaatcaact     24000
aagcacctag caggaaggta aagacatcca gttcaccagc ctcccggaga ggcctacatc    24060
ctgtaatccc agcacattcg gaggcgcact cggaaagatc accgaacgtc aaaaattcaa    24120
gaccagcctg accaacatgg aaaaaccctg tctctgctaa aaatacaaaa ttagccgggt    24180
ttggtggcgc atgcctgtaa tcccagctac ttgggaggct gaggcaggag aatcgcttga    24240
acctgggagg ttgaggttgc agtgagccaa gatcgtgccg ctgcactcca gcctggtaac    24300
agagcaagac tctgtcaaaa agaaaaaaaa agaaatccag aagacctagt ttctattcct    24360
cactctgatt tgatatgtga agttaggtca cttagacatt taattttct aggctttgct     24420 ttcttgcatc taaaaaacaa ggtgattgga atgttattaa tctatcaaat ataaacattt    24480
cttttcttcc ctttagtccg cttccggaca caacagggc ttgattctgc agtagatcct     24540
gtccagatga aaaatgtcac ctttgaacat gttaaagggg taagttaaga agattgcctt    24600
gccttcttca tacatcctct aattgatact ctatatgagg tcgatatttg attctacagt    24660
gtattctaga ataggtaaaa ttgtgtccaa agtattaga aacattagta ttttgggata     24720
aataataata gccaaggatc aaatcttgct ttatggcagg ggatagtata atttatgaag    24780
gagcagcctg gtgtagtgga gtgaatgtgg acttcagagt caagctgact aatgtttgaa    24840 attcatttt atacttatta gctatgagac cttgaagaaa ttactttaga tcctgacaga     24900
taatgtatgt gcttgacaca tagtagatat ttaataaatg gtccttcttt acctgtacct    24960
cttactgatc tttgtaactc cactatctaa aacatgttag acaatgtata tttcttgaat    25020
gaatagaatg gataaatgct agtttatagt tgattaattt gttaaatatt taatagtatc    25080
tattaagtgc taggccctat tttagctgct gggatagaat aaataatctc tgcattctta    25140
gagtttaaac tctaaaagca gtaattggac actgatatgt gatgtaagaa aaagtagagt    25200
atgttaaaag aataaaagtg tatggaggaa aaagtagagc agggtaaaga ggattgggag    25260
ttttgagaga aggcttacag ttttaaatgg agtgttcaag gtgtgattga tggagaaggt    25320
gacatttgag ataaaatctg aaggagaaga tggaataaac tgcatttatc tgagaaagga    25380
acgtttctga ccaaaggaac agtttgagca aaggctctca agtaataggg tgtctgactt    25440
gttcattttt gaaagtagaa ctaataggat ttcttattgg aacgtagggt gtaagagaaa    25500
agaggagtca aaaagagcca caagattttt ggtctcagca attagaagga tagaattgac    25560
atttactgag atttttgttt ttgttttga gacggagttt cgctattgtt gcccaagctg     25620
gcgtgcaatg gcgtgatctc ggctcagtgc aacctccacc tcccgattc aagcgattct     25680 cctgcctcag cctccagagt agctgggatt acaggcacga gccaccacgc ccagctaatt    25740
ttttgtgttt ttagtagaaa cagggttta ccatgttagc caggctggtc ttgaactcct     25800
gacctcaggt gatccacgca gatcaaagtg ctgggattac aggcgtgagc cacggtgccc    25860
ggcctttagt gaggttttaa aaggctgtga gtggagcaga tctgggggac aaaggttaga    25920
aatttagttt taggtatgtt aagtgtgaga gatacgaatg aaagtgttga gtaacttgga    25980
tataccactt tggaggtatg ggagaggtct gagctagaat taaaaatagg agattatatt    26040
tatatgtatg ttaagtccac atgtttggat gagatcaccc agggagtgag tgtaaccaga    26100
agagagattt aaataccgag ttacagagca cttacttgaa ggttcacaag acagagaaga    26160
```

-continued

```
gaagccagga accaagatga aaggagctg ccagtgagtt aggtgacaat ggtatcctgg    26220
aagaaaatat ttctatgatg aggggagtga tcagcaatgt gaaatgctat tgatgggcca    26280
agtgagaact aaccatttga tttagcagta ggtcattggt gtacctgata aagagcaatg    26340
ttagtggagt agcaggggtt aaattccaat tgcagtgggt ttacaagagg tggaaagaaa    26400
tgagatggaa tagaggattg caaacaattc ttggattttg tctgacagaa gagcacagat    26460
aatgtatctc ataatacaaa ataaagttgg aatgttggta aactgttagg tggggggtt     26520 tgtgggaaat tgatagaatc aaggtcacca gcagagagaa tatggctggg agaggaggaa    26580
tgagtggtta atggaggaag taaattgtgt agcaatagga gaatgaatgg aaacaggaaa    26640
taaaactgtt gtgctcactt gaattttggg atcatgaatt tatattaaga caagtcaaaa    26700
tgagtggttt ttctactgat tttttttttt attttatctt ttccaaatgt gaattctgca    26760
actttagtac cacactgtgc tcttctctgt gctttgccat tatatctgct ctattacatt    26820
tgatttctca gaactgtagt ggctgggtaa ttatctttca ggagtgtttt agaagaaatt    26880
cttccgcagg agggatttga agtacgtgat ctgaggactc ttccaactct gaagagattg    26940
gttatgttat tatttctgct tttcttcttt acttattcgt gtctctgttt atacataacc    27000
atgttttttc agccttgact attggggaat aaggcattgg gaatcattat gatagtttta    27060
caaccaagta gttctttcct ttcctttcca gtttaaatgg ctatgaaccc tgttggaatt    27120
gtataaaggc aacaattgag gaagaggttg gtgcagtgat tatttgaaaa cttcagtcat    27180
cagcgtggag ggcccttctc attgtgtttg aggtctgcat gccttttcta aattgagcct    27240
gtattaaggc tgaggtcaga cacagcattg ttattctctg tctgtaatgt acttacatac    27300
ttactgaata tatcacactt cttttggaat gagagttttt tttttttttt tttttttttt    27360
ttgagacagg tcttgctctc ttgcccaggc tggagtgca gtggcatgat catggctcac    27420
tgcagctttg accttctggg ctcaagtgat actcctgcct taacctccct tgtagctgag    27480
accacaggca tgcaccacca cacttggcta attttttaat ttaattttat tattctttct    27540
agacagggtc tggctctatc acccagactg aagtgcagta gtgtgatctt agctcacaac    27600
aacctcctcc tcctgggctc cagccatcct cccgcctcag cctctcaggt agctaggact    27660
acaggcgtgt gcccctatgc ctggctaatt tttgtagttt tttttttatag agtcgggatt    27720 tagctgcgtt gcccaggctg gtcttgatct cctgagctca agtgatccac ccatctttgc    27780
ctcccaaagt gctgggatta taggcatcag ccaccaagcc cagctgattt atctttcttt    27840
ttcttcttct tttttttggg gggtggggga gcggtgtaga gacagagttt cactttgttg    27900
tccaggctgg tctcaaactc ctgagctcag gcagtcctcc catctcagcc tcacaaagtg    27960 ctggggggtaa caggcatgag ccaccacgcc tgtcctggaa tgtgggggatt tctgagtact    28020 aaactaaagc catgctgata actaagcata gtgaaagtag acatcacaat taaggtagat    28080
ccttaccaag ttttccatgc taaaatgaat caattttata attgctgtaa gacctaaatt    28140
tatatagagc aaagtaattc agtagcattt accagaacag gtttgccatt aggtagttcc    28200
tgtgacaaat gtttaccaaa tctcaaagag cttgtatagg aatgtcattt ccttgcctag    28260
aatttctgaa tatatgggca cacttatata tatagcctta aaaatattaa taaggctttt    28320
taataacttg attcattacc ttgatccat taactatttt ccttgataga tcttatgttc     28380
ctcaagtggg gattctcttg ccacagaatt tggagagaga atatagttta tttgagtatt    28440
aaattatgtt taatctcttc tttattccta cagcttaaaa ttggaattat atctattatt    28500
```

```
ttgaccaaat atattttagt cttcttttag tacatggata ttatcttcca agttctcttt    28560
taataaacca gccaagtctt ttttaacca taaatttcat tgaagtttaa caaattcaca    28620
caacagtgca caaatccata aattttcaca aactgtctgt gttataagta cccagctcaa    28680
gaaatagaac cttagcagaa gcccagaacc tccttgatgc ctccttctgg ttactaacct    28740
agggacaatt tcctgtctaa taccatacat gaattttccc tattttttgaa ttttagataa    28800
atgtaatcca tatagaatat cctcttttgt atgaggcttc ttttattcaa catgtttgtg    28860
agatccatct atgttacttg gagttgaggt ttatttatcc tttattgcat agtatcccat    28920
tataagaata ctacaacacg gtgcaattac actactttag ggtggacatt tatttctagt    28980
ttttggttca aatacagctg gtgtgactac tttttataca agtctcttgg tgaacatatg    29040
tacacgcttc tcctggacct aggaatggac aaagctttgt tttgtatttt tttaaatact    29100
ctgaaaagaa aatgctatgt ttttaaccat taacttgatt aaaacattat tacatttta     29160
attatttaat cagaataact ttcaaagatc atttcaagtc taacaaaaaa acataacttt     29220
gttcttaat aagtgtaata tttcctggaa atatgcctgg gaattttttct tgaaataata    29280
agcgaatctt gacattaatt ggacattttc agaatgccct ttggcgtgaa gctatgtttc     29340
atgttttaga atgctcctct ctaggtactt tcttttaac cctgtccaat gtacttgact     29400
tttgttttct cactgagaaa atgaaagttc agaatgattt ttttgggat agtaaggaga     29460
ctttgcataa ttggaaataa tggtcagggg aaaacccttt gttttataag gggccatttt    29520
tgtatgcttt tttactgaa acagagaagg tcaggttaat tccatatcca aattaaattt    29580
atgattttca aaagggaagc cttgataatc taaccaaacg tgtccattat ctaaagttat    29640
ttggaaaatt gtgtcacttt aggtggagga agctaaacaa gaattacagg aagttgttga    29700
attcttgaaa aatccacaaa aatttactat tcttggaggt aaacttccaa aaggtaagat    29760
atcttttctt tatcatgatt tgatggaaaa aacaaaaaca aagaaacaaa caaaaaaaac    29820
ctatattact tatttaattt taactgatta aagtttaagt cttaattgct attttacaaa    29880
atagatgttc attctgaaca tacaattcca tagccttttt tttttggtaa ctgcaagttt    29940
ttatatactt tcaaatttaa agttacaaga atagtacata gaatgctcct catacccttt    30000
acctagactc acaaattttt aatatttagt ttccttttta gacccaggct tgagtgcagt    30060
gatgcaatca tggctcgctg tagccacaac ctcccgagtt caggcggccc tcccaagtag    30120
ctgagaccac aggtacacac caccatgctg gctaattttt gtattttttg tagagatgag    30180
gttactccat gttgcccagg ctgctcttga actcctgggc tcaagcgatc cactgacttt    30240
ggcctcctaa agtactagga ctgcaggcat gagccagcgc actcaaccta actccatttt    30300
aaaaatcatt cactttgtct ctttatgtat atataaatat aaaaattatt tgtaaataaa    30360
taaatttta actatttgag agtaaattgt aaacaatcac cccaagtgtg tatttcctaa    30420
gaataaggat attcttctat gtaactccag aataatatta aaattaggac attactgggt    30480
gtggtggctc acgcctttaa tcccagcagt ttaggaggtg gaggcgggtg gattacttga    30540
gatcaggagt tcgagaccag tctggtcttg aaccaggggc cattggagtt ccaaccagcc    30600
tggccaacat ggtgaaaccc tgtctctact aaaaaaagaa attagctggg cttggtggca    30660
ggcgcctgta atcccagcta ctcaggaggc tgaggcagga gaatcgtttg aacctaggag    30720
gcagaggttg cagtgagccg agattgttcc cactgcactc cagtctgggt gacaaagcaa    30780
gattctgtct caaaaaaaaa aaaaaaaata ggacatttaa catacataca aaaccattat    30840
caaatttaga gtctatattc aaatttcagc atttgctcca atagtatcct ttgtagtgtt    30900
```

```
gccctgatcc ctacccactt ccccagttca ggacctaatc caggatcaca ggtaacattt    30960
aggcttttat tgtttttttt ttttttttt ttcaaatgaa acaatgaaac aattccttag     31020 cctttgtga gggagtggag agaagaggat ctttcatgat ttttacagtt gcaaagagta     31080
cttgcctaat tatttataga atgttctcag tttagctttg tctgatgttt tctcatggtt    31140
aacatgactt ttaatgactt cacagtatcc ttctaattta tggttgtatc acaatttaac    31200
catttatatt gaattttat atggtttcca gttttttgc tattaagaat agtgctgtgt      31260
ttcatcttaa ttcaaggctt tgcctgcatg cttaattatt tctttagaat aaatttctag   31320
aaatggaatt gctgagttaa aggatgacac tccttttaa tgcttgtttt tatgctgcca     31380
actatctcca ctgaaaatac agcagtgtat gaaattattt gcagtaacct ttgctaattt   31440
agggtacatt tattaaatca gtgcttaata atgataactt tagctaatat cactggcaaa   31500
agccttatca acatcatgta cttcctgatg ctctagaaag gacccaagtg atggcttatg   31560
tggtgtccac gcaaaaagga attaaaaaag agcacaatct caatacaatc atgagaaaac   31620
actggaaaag cccatatcag gagacattcc acataccacc tttacattta tttaaacatc   31680
acagagtgaa tgtttaaaac catagaagta ttaatagtta cactcttcct ctttctaatc   31740
acaaggagta ttttaaattt gtagaaaatt tgagtagtat aaatttgtag aaaaatcttc   31800
agataccaag atgtaatcca cagaaattaa tatgatttaa accagttaag tataactaaa   31860
acatgacaat actaggatag tcttaaagct atttttgagc ttgagctttc tttaaaattt   31920
tttttatgtt aaaatgcagc aaacatgtat gtaaagaagt tttgttgctt tttaaatgta   31980
atatgtatat ttataaaaac atataaatca ggtaattctg tttttctaac gtgaaaatct   32040
ttggtgttat gaaaatttgc aaacatggaa accttgaaa gaacagtaca attaacatcc    32100
atatcctatc cacttagact caacaattgt taacattctg tcatatttgc tttctgtgtt   32160
atgtgtgtat ttttccccct gaacatttga agaaaacta taaacatcaa ctacttgaca    32220
tctaaagact ttcttgtaca tcacctaaga ataaggacag tgtcctaaat aaacataata   32280
accttatccc accaaaggaa attatgccta tttccttaat atcatgtact ctcagtcttg   32340
tttaaatgtt tcaccagat gtctctagaa ttttttgttc tttatgaaaa agcatcaaat    32400
caggattcac taattacatt tggttgttta gtcttttaat ctattttac atgaattta    32460 tcttatttag tgataaatgg gtttatattt ttttgcctca agattctccc tgtcatgtct   32520
cttgttgata tggaaacaat atttatataa tacaggaaca ttaattttgg acaagattct   32580
gaagtgaacc attagcagag acaagtacgg tttgctgtgt ttcaaaatat tggttattgg   32640
tgtgacctca gcctgaaaat tatataaatg aataattatt tattttatag gttcatatcg   32700
agggattttt taaaaatact ttgaatcatt ctcgttttca ttttctttta ggaattcttt   32760
tagttggacc cccagggact ggaaagacac ttcctgcccg agctgtggcg ggagaagctg   32820
atgttccttt ttattatgct tctggatccg aatttgatga gatgtttgtg ggtgtgggag   32880
ccagccgtat cagaaatctt tttagtacgt tttggtgtat ctttgatgca gtgctaaatt   32940
ttgttaaggg aagtgtgtat cttaccctt ctttgctaat tactttttt cttccttttt     33000 ttaatttcta ttttttgggg cctccagctt tgcatgctaa ttgttttga ttgatagtta    33060 aaatagccat tgtgggacct tggtttgggt aacttactat atgaattatc ggaagagcta   33120
gtggaagtgc aagatgaagt tggaggctac caaaaatctc ttagtgtttt ttcatttat    33180 tcatcaattt tgtagtatgg aattaaggag taattagctt caaacctgat tgtatatatt   33240
```

-continued

| | | | |
|---|---|---|---|
| tgtatagctg gaaagaatga atgaatgccc aactgttttg ttttatatca tttctttggt | 33300 |
| atagttttt ccccctgaa gatactattt ttaagtcagt aaaaaatgac gtcctttct | 33360 |
| ttcagtgaat attttttgtt ggcttttgac agttgtatag gattttaata tttatctcgt | 33420 |
| tttgttcaaa agtgttgact ttctttcagc ttatttgaat gttttttgtt ttcttagggg | 33480 |
| aagcaaaggc gaatgctcct tgtgttatat ttattgatga attagattct gttggtggga | 33540 |
| agagaattga atctccaatg catccatatt caaggcagac cataaatcaa cttcttgctg | 33600 |
| aaatggatgg gtaattgagt cttcttttt cttagaatat ggtgatgcct cccagcattt | 33660 |
| gatatacgta gaattgatct tatgcaaatt atttccataa ggcatttcat atctagagat | 33720 |
| atgaaaaatg tgatgtgtat aggaaacaga gtagtccctc atgcaagaac tcaagacaag | 33780 |
| cttttctct cagtattgta ttgttttcat tactaactgg atatttgaat atcaactcat | 33840 |
| cttatttaat ttatggtatt tatatccttt ttcatttatt gttacactta tgacagaaaa | 33900 |
| acaatgattt atgccgagac tagtagtcta tttgaagaaa tacagttgtt tctacataat | 33960 |
| ttatgactaa ctttgagtgt tgtggcagat ttaaagctta catcaatgtt cataatataa | 34020 |
| gaagcaagag gtgatgttgc tttgaaagaa gtatcttaaa actcaatata agacattttg | 34080 |
| aaaccacata ggaagcccag gagcaaataa tttgaattgg tatacttgaa agtaattttt | 34140 |
| caaaaattaa ccaggcacct aagctttta tatcaggtta tctttcctg catagaccag | 34200 |
| ataattgtga aggtatgtag tcagagatga attggtggtt tattatcagt ttctttctt | 34260 |
| ggctgttatt tgattaatga agctgggcat ggtggctcac gcctgtaatg ccaggacttt | 34320 |
| tggaagccaa ggtgggagga ttgcttgagg ccaggagttc aaaaccagcc tggtcaagat | 34380 |
| agcaagaccc tatctctact aaaaataaaa acagtcaccg gcacagtag ctcaagccta | 34440 |
| taatcctagc actttgggag gctgaggcgg gtgtattgct tgaggtcagg agttcaagac | 34500 |
| caacctggcc aacatggtga aacccgtct ttactaaaaa tataagaatt agctgggtgt | 34560 |
| ggtggcaggc gcctgtaatc ctggctactc aggaagctga gacatgagaa ttgcttgaac | 34620 |
| ctgggagatg gaggttgcag tgagcgccat tgaactccaa cctgggtgac agtgagactc | 34680 |
| catctccaaa aaaaaaaaa aatagtggct tgtacctaga aattggggag aaaagattta | 34740 |
| aaataaata aaaaataaat tagtcagata tgttggcatg cacctgtcat tccagctact | 34800 |
| tgagaggttg aggcagaagg ttcacttcaa cccaggagtt tgaggcagca gtgagctatg | 34860 |
| atcatactgg tgcgcttcag cctaggccac aaagcgagtc ctagtctcaa aaaagaaaa | 34920 |
| caaaccagtt ttgtgtagag catttctaca tgtgtgctgt gcttcagtgt tagtaaaaga | 34980 |
| tactatttt ttttccaatat agttttaaac ccaatgaagg agttatcata ataggagcca | 35040 |
| caaacttccc agaggcatta gataagtaag tattaaaaga agattttgt gaagtactgt | 35100 |
| tacatgctac aaaattgtgc taaagaagt ccgttgcaaa agatcacatc aacactgtat | 35160 |
| gattccattt atatgcaata tccagaataa gcaaattcac agagacaaat tgggttagcg | 35220 |
| gttaccagag gttagggaga atggggaatg gctgtcattg gatatgggat ttctttgtgg | 35280 |
| gggatgggaa tattctaaaa ttagattgtg gtgatggttg tacaattctg aatgtattaa | 35340 |
| aaaccactga agtatccact ttaaattatg tgaattacat ctcaataaaa cttaaaatat | 35400 |
| ttatttgtta tatgtcacaa aagttgtatg tagagagggt tttaaaata aattaactgt | 35460 |
| agtattataa ctaggtttaa agttactatg aaaaattt actgtagaag ttattcgtat | 35520 |
| tttcatttga tcagtagttt gtcactgcct aagactctag tctaacattc tgtacttagc | 35580 |
| agttgagatg gatgtgtggt tctcataata gtttgttgtg gaattatttg ttcctggact | 35640 |

-continued

```
gaattacctg catgcttttg tttctgaggg gtaggctacc taggtacaca cgtgtatcta   35700
aatgaacctt tgttctgctt tctggttatt gacactgtta cttgagccat gttttaaagg   35760
aactatctga atatttatgt acaaaactcc atctgcgctc tggctgccat tggcttccca   35820
gtcatgtcat tagggtgtca gtcctgttga atttgagctt aaatagtttt aatttatatt   35880
ttccttttgc attcttcctg tagtgcctta atacgtcctg gtcgttttga catgcaagtt   35940
acagttccaa ggccagatgt aaaggtcga acagaaattt tgaaatggta tctcaataaa   36000
ataaagtttg atcaatgtaa gtatcaaaac aaacatttgt catttctgta aagtggtaat   36060
ataccactca ccctgtttgt ggtcctttca tgatacatgt attaacatta aaagaccagt   36120
tcatttttgt cttttttttt tccattagta tgttcgttta aaagtccatt ccttagtgta   36180
tatccaggag attctattgt tttgaaccct gagtctaaag aaaggttttt ttagagtatt   36240
cagacagata atatttgagg atacatacat atacatacac acacacacat ttttttaaga   36300
tgaatgtaaa atgcaaaata atttaaaaaa gctgcagaaa cagtaactca tgatatagtc   36360
agtgtgggc caaagagaa gaaagcaaat tataaaacaa aacacatgga aatttattac   36420
tcacttgagt aataaatgaa attattaaag ctgcagtagt ttcagagata gctgtatcaa   36480
ttcattaaac tatacatgtt tcctataagg gcagctttta tgtctaaagt atttccagat   36540
gaaattcaga gaaaagtga ctaaactatg gctcagaata gctagctatt ttcttttttc   36600
ccttggaatg tgaggtgttt ttttttttgg tttttttttg agacaagagt tttgcccttt   36660
ttgcctaggc tggagtggag tggcacaatc ttggcttact gcaacctcca cctcccgggt   36720
tcaagtgatt cttctgcctc agccttctga atagctggga ttacaggtgc atgccaccat   36780
gcccagctaa ttttttgtatt tttagtagag atggggtttc accatgttgg ccaggatggt   36840
ctccaactcc tgtccttagg tgatctgcct gccccagcct cccaaagtgc tgggattaca   36900
ggcatgagcc aacgcaccca gttggaatgt gagttctttg tgaagagctt tcttttacct   36960
gttttagact tattagcgtt gtgttctctt tttacattag ccgttgatcc agaaattata   37020
gctcgaggta ctgttggctt ttccggagca gagttggaga atcttgtgaa ccaggctgca   37080
ttaaaagcag ctgttgatgg aaaagaaatg gttaccatga aggagctgga gttttccaaa   37140
gacaaaattc taatgggtag gttccttttc ttttttttct gtcttttact tttcattgtg   37200
ttagataatt catttagggg caaatactct attcaaacag ctaaagccat ggctatgttg   37260
aatctaatct tactctaaaa cttcagtgtc tgggttttca agatttgtaa taaatgattt   37320
tacaaaattc ccaacttaac atcaaacaaa tgccattaaa ctgtaacatt tcttgacaa   37380
taatcttgtc agtgatacag aactgatttt atagtgtacc acatttatta gttttgtctc   37440
tttcttagaa aaccttttt tctgactgga aagctttaaa aagtgatggg aacatgaaaa   37500
tatatacttg acaacaccac aatttggcat cttacgaaac aaatatattc tagttgctta   37560
tgtaattata tagttaaact ggtagtgggg agatgaggca cgtatacatt tcctcttgtc   37620
agacattgct gcgaaaaagg atactttatt ctgtgcttaa tttcgatttt aaatcttgga   37680
ttggcttaaa atcacattaa ttatgatatt cttgttaaac tggaagttta tttatagaa   37740
atagaaataa gttttcccctt ttgaattaag atgatagttt tgcagttttt ggttttcagt   37800
taaattgtta aagtttgtat gtgttaggaa tgaattctgc ccatttttaaa aaactttgta   37860
gactgggcgt ggtggctcac acctgtaatc ccagcacttt gggaggccaa ggcaggagga   37920
ctgcttgagc ccagaatcgt tggagttcaa gatcagctgg gcaacatagc aagactccat   37980
```

-continued

```
ctctaccaaa aattttaaaa attagttggg tggggtggca tgcgactgtg gtcccatcta    38040
cttgggagtc ctaggtggga ggattactta agtccaagaa gttaaagcta cagtgagcca    38100
tgatcatgcc actgtattcc agcctgggtt acagaccctg tttaaaaaga aacaaaatta    38160
ctaaaaatta ctaaagctag gtgcagtggc acatgcctgt aatcccagca ctttgggaag    38220
ctgaggtggg tggattgctt gaggctaaga gttcaaggtt ggagtgagct ataataagaa    38280
tgactttaag gagaatgagt tttttgtttt ataatattaa tcccatatca gatacattca    38340
cctctcagta tccactgaag gggtggggat tggttccagg acccatgtgg ataccaaaat    38400
tcagggatgc tcaagtgtct tttataaaat ggtgtactat ttgcatatac ctacataatt    38460
ctcctgtata cttcaaatca tctctagatt actaatacaa tataaatgct ctgtaaatag    38520
ttgttataat gtattttttt catttgtatt attttttatt gttcctcttc cccatagttt    38580
taatccttat ttggttgaat ctatggatgc agaatctgct gataggaagg gtggagtgta    38640
tttgatttgc agacaagaat gtgttttgtt gatttaaata tacctttcta atggagtatt    38700
tactcaatta aatttatctt agggcctgaa agaagaagtg tggaaattga taacaaaaac    38760
aaaaccatca cagcatatca tgaatctggt catgccatta ttgcatatta cacaaaagat    38820
gcaatgccta tcaacaaagc tacaatcatg ccacgggggc caacacttgg acatgtaagt    38880 ttttttgtagt gtctcgccct gtcacccagg ctggagtgca atggcgcgat ctcagctcac    38940
tgcaacctct gccttccgga ttcaaacgat tctttcacct cagcctccca agtaactggg    39000
attacaggtg cccaccacca cgcccagcta attttttgtaa ttttagtaga gatgggtttt    39060
caccatgttg gccaggctgc tctagaactc ctgacctcag gtgatccacc tgcctcagtc    39120
tcccaaagtg ctgggattac aggcgtgagc caccatgccc tgcctaattc ttaaatatct    39180
aattactccg ctgccccaaa agggaaaaca ttatgttttg tagtaactga ttcagtagtt    39240
tctctaagat ttttatcatt tagtacaagt ttatcagatc tttcaacatt gtagacattt    39300
aaaaaatttc tatgcacctg gggagaaaac agtcctattg cagcattatc cacctattgt    39360
tgttgcttta taaggatgt ttttattctc taattgctgg tttttcatca gtcccctgat    39420
gaccagcttt cagcaacatg gtataaagta ctttagtgag agctaaatga taattctggt    39480
ttgtattttt ttattttgcc cagtcttacg gtgctgaaat tctggttttt aatgtaacta    39540
tatcagaact gtatctgaat tttttttaaa tttttatttt attttatatt gatggagtct    39600
cgcgatgttg cccaggctac tctcaaactc ctgggctcaa gtgatcctca cacctcagcc    39660
tcccaaagtg ctgagactac aggtatgagc cactgcaccc agcctgtatc tgaatttctt    39720
tcattacatt ttattttatt ttaatttaat ttggttttat tttatttatt gtattttatt    39780
tttgagatgg agtttcactc ttgttgccca ggctagagtg caatggcatg atctcagctc    39840
actgcaacct ctgtctcctg gcttcaagtg agtcttctgc cttagcctcc caagtagttg    39900
ggattatagc catgcaccac catgcctgcc taattttgta ttttttagtag acacaggatt    39960 tctccatgtt ggtcaggctg gtctcgaact cccaacctca ggtgatccac ccacctcgcc    40020
tgccaaagtg ctgggattca ggcgtgagcc accgcaccca gcctctttcc ttatttttta    40080
tctgattaat ttttaattgt ctaggtgtcc ctgttacctg agaatgacag atggaatgaa    40140
actagagccc agctgcttgc acaaatggat gttagtatgg gaggaagagt ggcagaggag    40200
cttatatttg gaaccgacca tattacaaca ggttagcttt aaagaatggc tttagttcaa    40260
attatatgtg gtcttaaaga tatgttttaa aatggtatgt tttatttta ttttaggtgc    40320 ttccagtgat tttgataatg ccactaaaat agcaaagcgg atggttacca aatttggaat    40380
```

```
gagtgaaaag gtaatagatt ttttaaatcc ttttcatgta tcaaattatg tgtcaagtgt    40440
tgatttgaga gctggttctg attataaatt ggtaatattc acttttttctc tcactccaaa   40500 tggatttgag gctcttttatt ctgaacattg ttattctctg aataaagaaa atggaccttc   40560
tcttagctgc tgagaatgag ctgcccagat agtaactatt acttcacgag ttaattaagt   40620
gataaagcaa ggtgaattcc ttagcttttc catgtggcat gaaagagtct actttctaag   40680
tttggttact ttactgtttc cctctatttc atattttcat cttgtcattg ttccttgaag   40740
cactactata ctctgtgaat tatggatttc tatatttgaa gtagctgcca aggttttttca  40800 agaaagtact gagaaccaga cttaaaatga ttttaggctg ggcactgtgg ctcacatctg   40860
taatcccagc actttgggag gctgaggaga ctgtattgct tgagcccagg agtgagttct   40920
ggaccagcct gggcaacatg gcacaacccc atctctaaaa aaatacaaaa attagccagg  40980
tatggtggtg tgtgcctgta atcccagcta cttgggagtc tgaggtggga ggattctctg   41040
aacccaggag gtcgaggcta cagtgagtcc actgcactct acctgggtga cagagcaaga   41100
ccctgtctcc aaaaaaaaaa aaaaagattt taaatgttct gtcttgctca tacttttact   41160
attttgatat tagtgttttt ttgtttcttt gttttttgaga cggagtcttg ctctgttgcc   41220
caggctgtag tgcagtggcg tgatgttggc tcactgcagc taccgcctcc cgggttcaag   41280
cgattctcct gcctcagcct cccaagtagc tgggattaca gtcaacctgc caccatgcct   41340
ggctaaatgt tagtctttat actttcagaa gaatgtggaa atttctttgc cctcaaatgc   41400 agttttttatt tttatttttt ttggagacgg agtctcgctc tgtcacctag gctggagtgc   41460
agtggcgcaa tgtcagctta ctgcaaccac cgcctcctgg gttcaagcga ttctcctgcc   41520
tcagcctcct gagtagctgt gattacaggc acgtgccgct atgcccagct attttttgtg   41580
tttttagaag aaatggcgtt tctccgtgtt tccaggctgg tctcgaactc ctaacctcag   41640
gtgatccacc cgcctcggcc tcccaaaatc ctaggattac aggtgtgagc cactgtgccc   41700
ggcctcaaat gcagttttct attgtacttc tttcttgtcc cccgtatatt tgtttccctta   41760 tataggat agtactttct ctttcaaatt tgttggtgtt tgggggtttt ctgttcaatt     41820
actttcttcc ttttggtttt agcttggagt tatgacctac agtgatacag ggaaactaag   41880
tccagaaacc caatctgcca tcgaacaaga aataagaatc cttctaaggg taataatatt   41940
ttttgtgctt atttattttc ttaggaacaa tgtgcttaaa tagtcaggtt cttaaaaaat   42000
aacagctgaa ggccctctgt tcactagaaa catcatttta taaaataaag ataatagtca   42060
ccatggtgtc tgggggaaaaa attaaaaaat aaagataata gttgcagcat ttcagcaatg   42120
atttaaatgt tattaaggca cctctctgtt catgaacctg gacacgggct aagaacagtt   42180
ctatattgca tggttgtaaa aattcaattc tcagggtgag ggacaaaata actacatatt   42240
aggtattagg tacagtgtac actatgtagg tatggataca ctaaaatccc agactttacc   42300
actatacaat tcatccatgt aaccaaaacc acttgtaccc cataagctgt tgaaataaaa   42360
tctatatata aaattttata tgtatataaa attcaattgt actttagctg caaaactgta   42420
agaggtaata gaatgggaag agtattgttt attgagtctt tgacatgtat tcaacaaata   42480 aattttttt tttttttta tggagtctca ttctgctgcc caggctagag tgtagtggca   42540
tgatctcggc tcactgcaac ctaagaaata agtttagtag gtgttttatt gttggttttt   42600
tgtgggtttt gtcatttttt tttttaaggg gatgggtctt gctatattgc ccaggctgga   42660
cttgaactcc tgggctcaag tcaacctccc aagtagctgg ggctacaggc acacaccact   42720
```

```
atgcctagct ctatgatttc agttttttgg ttttgttttt tctttttttt tttttttttga    42780 gacagagttc tgctcttgtt gcccaggctg gagtgcagta gtgctatctc ggctcattgc    42840
aacttccgcc cttctgggtt caaagtgatt ctcctgcctc agccttctga gtagctggga    42900
ttacaggcgc gtgccaccat gcctggctaa tttttttgtat ttttagtaga gacagggttt    42960
cactatattg gccaggctga tctcaaactc tgacctcagg cgatccaccc acctcggcct    43020
cccaaagtgc tgggattaca ggcatgagcc actgcgcccg gcccaatttc agtattatgt    43080
atgttgaatt tgaggcatct tagttggaaa tagatgtggg aacttagtgg agagattggt    43140
tatgtattgc atttgaatgt tgaagctacc cattcatgaa ggcaggtctt tttttttttt    43200
tttttttttt tttttttttt tttttttttt ttgagacagc atcttgccct gtcacccagg    43260
ctggagtgca gtgctgtgat cttggctcat tgcaacctct gtctcccaag ctcaagtgat    43320
cctcccacct cagcctcctg agtagctggg actataagcg catgctgcca tgcctagcta    43380
attttgttat tttttgtaga gagcatttca ctatgttacc caggctggtg tcgaactcct    43440
gggctcaaac gatccacctg ccttggcctc ccaaagtgct gggattacag gtgtgagcca    43500
ccgcacccag ccaggcaggt tttaagggta agactgacca gcctgggcaa catggcaaaa    43560
cctcatctct acaaaacata gaaaaattag ctgggcatgg tggttcatgc ctgtagtccc    43620
agctacttgg gctgaggtgg gaggatcacc tgagcccagg gaggttgagg ccgtagtgag    43680
ttgtgattgc ctgacttcac tccagcctaa gcaacagtga gactgaaaaa aaatagaga    43740 gagagagagt gacagagctg agtgccaaag tctttagtga gtaaggacta tgtttgtcag    43800
atggcacaat gaagacggtt ggatagctcc atagtcaaat ggcctggact tcaacagaat    43860
aggaagagtg cattatataa gagggtaggt tagtaatggt ctgaaagagg taatgggaac    43920
aatgagctca gctgtttact gtgaagtaac tagggtaaac atgaacaaat agcacttgag    43980
agggcttagg gaatgcattc tccacaggag ggaccatggg tttgattatt tcaaggaagt    44040
agagggaatg ctttagagta gttaaggata cagaaagttt gtatgatgga aaggtttaga    44100
gagtgttata gaagaggtgg tctctgcctt ctcaggtgtt tattctcttt tccttactat    44160
gttataatgc acaaattatc tctactgtag aatcaagatt ctacatgatt ttataaatat    44220
aaacagattt catatttttt agggtacata agtttttct ttctcttccc attgactggt    44280
tttcgcatcc ctgcatttgc tgctgcttac gtatctcctt ttctatttca ggactcatat    44340
gaacgagcaa aacatatctt gaaaactcat gcaaaggagc ataagaatct cgcagaagct    44400
ttattgacct atgagacttt ggatgccaaa gagattcaaa ttgttcttga ggggaaaaag    44460
ttggaagtga gatgataact ctcttgtatt ggatgcttgc tggttttatt gcaagaatat    44520
aagtagcatt gcagtagtct acttttacaa cgctttcccc tcattcttga tgtggtgtaa    44580
ttgaagggtg tgaaatgctt tgtcaatcat ttgtcacatt tatccagttt gggttattct    44640
cattatgaca cctattgcaa attagcatcc catggcaaat atattttgaa aaataaaga    44700 actatcagga ttgaaaacag ctcttttgag gaatgtcaat tagttattaa gttgaaagta    44760
attaatgatt ttatgtttgg ttactctact agatttgata aaaattgtgc ctttagcctt    44820
ctatatacat cagtggaaac ttaagatgca gtaattatgt tccagattga ccatgaataa    44880
aatatttttt aatctaaatg tagagaagtt gggattaaaa gcagtctcgg aaacacagag    44940
ccaggaatat agccttttgg catggtgcca tggctcacat ctgtaatccc agcacttttg    45000
gaggctgagg cgggtggatt gcttgaggcc aggagttcga gaccagcctg gccaacgtgg    45060
tgaaacgctg tctctactaa aatacaaaaa aatagggctg ggcgcggttg ctcacgcctg    45120
```

-continued

```
taatcccagc acttttcaga ggccaaggcg ggcaaatcac ctgaggtcaa gagtttgaga    45180
ccagcctggc caacatggtg aaaccccatc tctactaaac atgcaaaaat tacctgggca    45240
tggtggcagg tgcttataat cccagctact ctggggggcca aggcaggaga attgcttgag   45300
cctgggagat ggaggttgca gtgagctgag atcatgccac tgcactccag cctgggcaac    45360
agagcaagac tctgcctcaa aaaaaaatta aaataaattt aaatacaaaa aaaaatagcc    45420
aggtgtgggg tgcatgcctg gaatcccagc tacttgagag gctgaggcac gagaattgct    45480
tgaacccagg aggtggaggt tgcagtgagc caagatcaca gaagccactg cactccagcc    45540
tgggtgacag agtgagactc tgtctcaaaa aaaaattaaa taaattatta taaccttca     45600
gaaatgctgt gtgcattttc atgttctttt ttttagcatt actgtcactc tccctaatga    45660
aatgtacttc agagaagcag tattttgtta aataaataca taacctcatt ctgaataatg    45720
tccctcattt tgactataac tgtgcttggt ttcaaaagca aaattaaaca aaatctcag     45780
tcccctccga agtgaacttt gtgttaccct gcgtcagaaa tgccaagttg tgtttacttt    45840
tcattcagat tttgtgaata tgaacatgct gttataggat ctacagatga atatttaact    45900
caatagaaaa attattttag aacacattgt attggtatta caaccagatt atattcttga    45960
cgttgacttc attaaaatta tctacaattt cctaataatt taagctgtat atggtcttca    46020
ttgaaaaaag atagatattg ttacaggaag cttgttacat tatattcttg accttttggt    46080
tgataatctt aaatcttaat gtaatttcaa actggcagaa atgttgccag cataatacat    46140
ggatgtctca tataccctgc atccagattt accagttgtt atcattctgc ccgttttta    46200
ttgccccaaa cctgttctgt ctccctctct gtatgtacat acatacacgt ataaaatatt    46260
gatgaagtct tatctgtctt aaattttttt acatatttgt tgaggtataa tttacatatg    46320
ataaaattca ttttaaatgt agagttgaaa gatgttgtgt gtgtaatcat caccacaatt   46380
agattttaga acatttccat cacccaaaac attgtcatgc aagtgtttgg attaattttt    46440
taagaaactt atgaactatt ttcaaagtga ctataatttt atgttctaac tagcaatgta    46500
ggagggttat agtttctcca catcttttgc agtgcttata gtctgccttt ataattatgg    46560
ccattctagt ggaccactca tatccaaatt aatctcatcc aagttagatc atttctctag    46620
tgacataaga tgctgagcat cttccggtgc ttattggcca tttgtatatc ttctttggag    46680
aagtgtctat tcagatcttt tacttctttt aattgggt                            46718
```

<210> SEQ ID NO 4  
<211> LENGTH: 716  
<212> TYPE: PRT  
<213> ORGANISM: Human

<400> SEQUENCE: 4

```
Met Phe Ser Leu Ser Ser Thr Val Gln Pro Gln Val Thr Val Pro Leu
 1               5                  10                  15

Ser His Leu Ile Asn Ala Phe His Thr Pro Lys Asn Thr Ser Val Ser
            20                  25                  30

Leu Ser Gly Val Ser Val Ser Gln Asn Gln His Arg Asp Val Val Pro
        35                  40                  45

Glu His Glu Ala Pro Ser Ser Glu Pro Ser Leu Asn Leu Arg Asp Leu
    50                  55                  60

Gly Leu Ser Glu Leu Lys Ile Gly Gln Ile Asp Gln Leu Val Glu Asn
65                  70                  75                  80

Leu Leu Pro Gly Phe Cys Lys Gly Lys Asn Ile Ser Ser His Trp His
```

```
                    85                  90                  95
Thr Ser His Val Ser Ala Gln Ser Phe Glu Asn Lys Tyr Gly Asn
                100                 105                 110
Leu Asp Ile Phe Ser Thr Leu Arg Ser Ser Cys Leu Tyr Arg His His
            115                 120                 125
Ser Arg Ala Leu Gln Ser Ile Cys Ser Asp Leu Gln Tyr Trp Pro Val
        130                 135                 140
Phe Ile Gln Ser Arg Gly Phe Lys Thr Leu Lys Ser Arg Thr Arg Arg
145                 150                 155                 160
Leu Gln Ser Thr Ser Glu Arg Leu Ala Glu Thr Gln Asn Ile Ala Pro
                165                 170                 175
Ser Phe Val Lys Gly Phe Leu Leu Arg Asp Arg Gly Ser Asp Val Glu
                180                 185                 190
Ser Leu Asp Lys Leu Met Lys Thr Lys Asn Ile Pro Glu Ala His Gln
            195                 200                 205
Asp Ala Phe Lys Thr Gly Phe Ala Glu Gly Phe Leu Lys Ala Gln Ala
        210                 215                 220
Leu Thr Gln Lys Thr Asn Asp Ser Leu Arg Arg Thr Arg Leu Ile Leu
225                 230                 235                 240
Phe Val Leu Leu Leu Phe Gly Ile Tyr Gly Leu Leu Lys Asn Pro Phe
                245                 250                 255
Leu Ser Val Arg Phe Arg Thr Thr Thr Gly Leu Asp Ser Ala Val Asp
                260                 265                 270
Pro Val Gln Met Lys Asn Val Thr Phe Glu His Val Lys Gly Val Glu
            275                 280                 285
Glu Ala Lys Gln Glu Leu Gln Glu Val Val Glu Phe Leu Lys Asn Pro
        290                 295                 300
Gln Lys Phe Thr Ile Leu Gly Gly Lys Leu Pro Lys Gly Ile Leu Leu
305                 310                 315                 320
Val Gly Pro Pro Gly Thr Gly Lys Thr Leu Leu Ala Arg Ala Val Ala
                325                 330                 335
Gly Glu Ala Asp Val Pro Phe Tyr Tyr Ala Ser Gly Ser Glu Phe Asp
            340                 345                 350
Glu Met Phe Val Gly Val Gly Ala Ser Arg Ile Arg Asn Leu Phe Arg
        355                 360                 365
Glu Ala Lys Ala Asn Ala Pro Cys Val Ile Phe Ile Asp Glu Leu Asp
        370                 375                 380
Ser Val Gly Gly Lys Arg Ile Glu Ser Pro Met His Pro Tyr Ser Arg
385                 390                 395                 400
Gln Thr Ile Asn Gln Leu Leu Ala Glu Met Asp Gly Phe Lys Pro Asn
                405                 410                 415
Glu Gly Val Ile Ile Ile Gly Ala Thr Asn Phe Pro Glu Ala Leu Asp
            420                 425                 430
Asn Ala Leu Ile Arg Pro Gly Arg Phe Asp Met Gln Val Thr Val Pro
        435                 440                 445
Arg Pro Asp Val Lys Gly Arg Thr Glu Ile Leu Lys Trp Tyr Leu Asn
        450                 455                 460
Lys Ile Lys Phe Asp Gln Ser Val Asp Pro Glu Ile Ile Ala Arg Gly
465                 470                 475                 480
Thr Val Gly Phe Ser Gly Ala Glu Leu Glu Asn Leu Val Asn Gln Ala
                485                 490                 495
Ala Leu Lys Ala Ala Val Asp Gly Lys Glu Met Val Thr Met Lys Glu
            500                 505                 510
```

```
Leu Glu Phe Ser Lys Asp Lys Ile Leu Met Gly Pro Glu Arg Arg Ser
            515                 520                 525
Val Glu Ile Asp Asn Lys Asn Lys Thr Ile Thr Ala Tyr His Glu Ser
    530                 535                 540
Gly His Ala Ile Ile Ala Tyr Tyr Thr Lys Asp Ala Met Pro Ile Asn
545                 550                 555                 560
Lys Ala Thr Ile Met Pro Arg Gly Pro Thr Leu Gly His Val Ser Leu
                565                 570                 575
Leu Pro Glu Asn Asp Arg Trp Asn Glu Thr Arg Ala Gln Leu Leu Ala
            580                 585                 590
Gln Met Asp Val Ser Met Gly Gly Arg Val Ala Glu Glu Leu Ile Phe
            595                 600                 605
Gly Thr Asp His Ile Thr Thr Gly Ala Ser Ser Asp Phe Asp Asn Ala
    610                 615                 620
Thr Lys Ile Ala Lys Arg Met Val Thr Lys Phe Gly Met Ser Glu Lys
625                 630                 635                 640
Leu Gly Val Met Thr Tyr Ser Asp Thr Gly Lys Leu Ser Pro Glu Thr
                645                 650                 655
Gln Ser Ala Ile Glu Gln Glu Ile Arg Ile Leu Leu Arg Asp Ser Tyr
                660                 665                 670
Glu Arg Ala Lys His Ile Leu Lys Thr His Ala Lys Glu His Lys Asn
            675                 680                 685
Leu Ala Glu Ala Leu Leu Thr Tyr Glu Thr Leu Asp Ala Lys Glu Ile
    690                 695                 700
Gln Ile Val Leu Glu Gly Lys Lys Leu Glu Val Arg
705                 710                 715
```

ISOLATED HUMAN PROTEASE PROTEINS, NUCLEIC ACID MOLECULES ENCODING HUMAN PROTEASE PROTEINS, AND USES THEREOF

FIELD OF THE INVENTION

The present invention is in the field of protease proteins that are related to the ATP-dependent metalloprotease subfamily, recombinant DNA molecules, and protein production. The present invention specifically provides novel peptides and proteins that effect protein cleavage/processing/turnover and nucleic acid molecules encoding such peptide and protein molecules, all of which are useful in the development of human therapeutics and diagnostic compositions and methods.

BACKGROUND OF THE INVENTION

The proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre or pro-protein precursors that are processed by proteolytic degradation to produce an active moiety. Thus, complex and highly-regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from non-essential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases (Subclass E.C 3.4.). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner A P Press, NY 1998). Also, for a review of the various uses of proteases as drug targets, see: Weber M, Emerging treatments for hypertension: potential role for vasopeptidase inhibition; Am J Hypertens 1999 November;12(11 Pt 2):139S–147S; Kentsch M, Otter W, Novel neurohormonal modulators in cardiovascular disorders. The therapeutic potential of endopeptidase inhibitors, Drugs R D 1999 April;1(4):331–8; Scarborough R M, Coagulation factor Xa: the prothrombinase complex as an emerging therapeutic target for small molecule inhibitors, J Enzym Inhib 1998;14(1):15–25; Skotnicki J S, et al., Design and synthetic considerations of matrix metalloproteinase inhibitors, Ann N Y Acad Sci 1999 June 30;878:61–72; McKerrow J H, Engel J C, Caffrey C R, Cysteine protease inhibitors as chemotherapy for parasitic infections, Bioorg Med Chem 1999 April;7(4):639–44; Rice K D, Tanaka R D, Katz B A, Numerof R P, Moore W R, Inhibitors of tryptase for the treatment of mast cell-mediated diseases, Curr Pharm Des 1998 October;4(5):381–96; Materson B J, Will angiotensin converting enzyme genotype, receptor mutation identification, and other miracles of molecular biology permit reduction of NNT Am J Hypertens 1998 August;11(8 Pt 2):138S–142S Serine Proteases The serine proteases (SP) are a large family of proteolytic enzymes that include the digestive enzymes, trypsin and chymotrypsin, components of the complement cascade and of the blood-clotting cascade, and enzymes that control the degradation and turnover of macromolecules of the extracellular matrix. SP are so named because of the presence of a serine residue in the active catalytic site for protein cleavage. SP have a wide range of substrate specificities and can be subdivided into subfamilies on the basis of these specificities. The main sub-families are trypases (cleavage after arginine or lysine), aspases (cleavage after aspartate), chymases (cleavage after phenylalanine or leucine), metases (cleavage after methionine), and serases (cleavage after serine).

A series of six SP have been identified in murine cytotoxic T-lymphocytes (CTL) and natural killer (NK) cells. These SP are involved with CTL and NK cells in the destruction of virally transformed cells and tumor cells and in organ and tissue transplant rejection (Zunino, S. J. et al. (1990) J. Immunol. 144:2001–9; Sayers, T. J. et al. (1994) J. Immunol. 152:2289–97). Human homologs of most of these enzymes have been identified (Trapani, J. A. et al. (1988) Proc. Natl. Acad. Sci. 85:6924–28; Caputo, A. et al. (1990) J. Immunol. 145:737–44). Like all SP, the CTL-SP share three distinguishing features: 1) the presence of a catalytic triad of histidine, serine, and aspartate residues which comprise the active site; 2) the sequence GDSGGP which contains the active site serine; and 3) an N-terminal IIGG sequence which characterizes the mature SP.

The SP are secretory proteins which contain N-terminal signal peptides that serve to export the immature protein across the endoplasmic reticulum and are then cleaved (von Heijne (1986) Nuc. Acid. Res. 14:5683–90). Differences in these signal sequences provide one means of distinguishing individual SP. Some SP, particularly the digestive enzymes, exist as inactive precursors or preproenzymes, and contain a leader or activation peptide sequence 3' of the signal peptide. This activation peptide may be 2–12 amino acids in length, and it extends from the cleavage site of the signal peptide to the N-terminal IIGG sequence of the active, mature protein. Cleavage of this sequence activates the enzyme. This sequence varies in different SP according to the biochemical pathway and/or its substrate (Zunino et al, supra; Sayers et al, supra). Other features that distinguish various SP are the presence or absence of N-linked glycosylation sites that provide membrane anchors, the number and distribution of cysteine residues that determine the secondary structure of the SP, and the sequence of a substrate binding sites such as S'. The S' substrate binding region is defined by residues extending from approximately +17 to +29 relative to the N-terminal I (+1). Differences in this region of the molecule are believed to determine SP substrate specificities (Zunino et al, supra).

Trypsinogens

The trypsinogens are serine proteases secreted by exocrine cells of the pancreas (Travis J and Roberts R. Biochemistry 1969; 8: 2884–9; Mallory P and Travis J, Biochemistry 1973; 12: 2847–51). Two major types of trypsinogen isoenzymes have been characterized, trypsinogen-1, also called cationic trypsinogen, and trypsinogen-2 or anionic trypsinogen. The trypsinogen proenzymes are activated to trypsins in the intestine by enterokinase, which removes an activation peptide from the N-terminus of the trypsinogens. The trypsinogens show a high degree of sequence homology, but they can be separated on the basis of charge differences by using electrophoresis or ion exchange chromatography. The major form of trypsinogen in the pancreas and pancreatic juice is trypsinogen-1 (Guy C O et al., Biochem Biophys Res Commun 1984; 125: 516–23). In serum of healthy subjects, trypsinogen-1 is also the major form, whereas in patients with pancreatitis, trypsinogen-2 is more strongly elevated (Itkonen et al., J Lab Clin Med 1990; 115:712–8). Trypsinogens also occur in certain ovarian tumors, in which trypsinogen-2 is the major form (Koivunen et al., Cancer Res 1990; 50: 2375–8). Trypsin-1 in complex with alpha-1-antitrypsin, also called alpha-1-antiprotease, has been found to occur in serum of patients with pancreatitis (Borgstrom A and Ohlsson K, Scand J Clin Lab Invest 1984; 44: 381–6) but determination of this complex has not been found useful for differentiation between pancreatic and other gastrointestinal diseases (Borgstrom et al., Scand J Clin Lab Invest 1989; 49:757–62).

Trypsinogen-1 and -2 are closely related immunologically (Kimland et al., Clin Chim Acta 1989; 184: 31–46; Itkonen et al., 1990), but by using monoclonal antibodies (Itkonen et al., 1990) or by absorbing polyclonal antisera (Kimland et al., 1989) it is possible to obtain reagents enabling specific measurement of each form of trypsinogen.

When active trypsin reaches the blood stream, it is inactivated by the major trypsin inhibitors alpha-2-macroglobulin and alpha-1-antitrypsin (AAT). AAT is a 58 kilodalton serine protease inhibitor synthesized in the liver and is one of the main protease inhibitors in blood. Whereas complexes between trypsin-1 and AAT are detectable in serum (Borgstrom and Ohlsson, 1984) the complexes with alpha-2-macroglobulin are not measurable with antibody-based assays (Ohlsson K, Acta Gastroenterol Belg 1988; 51: 3–12).

Inflammation of the pancreas or pancreatitis may be classified as either acute or chronic by clinical criteria. With treatment, acute pancreatitis can often be cured and normal function restored. Chronic pancreatitis often results in permanent damage. The precise mechanisms which trigger acute inflammation are not understood. However, some causes in the order of their importance are alcohol ingestion, biliary tract disease, post-operative trauma, and hereditary pancreatitis. One theory provides that autodigestion, the premature activation of proteolytic enzymes in the pancreas rather than in the duodenum, causes acute pancreatitis. Any number of other factors including endotoxins, exotoxins, viral infections, ischemia, anoxia, and direct trauma may activate the proenzymes. In addition, any internal or external blockage of pancreatic ducts can also cause an accumulation of pancreatic juices in the pancreas resulting cellular damage.

Anatomy, physiology, and diseases of the pancreas are reviewed, inter alia, in Guyton A C (1991) Textbook of Medical Physiology, W B Saunders Co, Philadelphia Pa.; Isselbacher K J et al (1994) Harrison's Principles of Internal Medicine, McGraw-Hill, New York City; Johnson K E (1991) Histology and Cell Biology, Harwal Publishing, Media Pa.; and The Merck Manual of Diagnosis and Therapy (1992) Merck Research Laboratories, Rahway N.J.

Metalloprotease

The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. *Bacillus subtilis* (McConn et al., 1964, J. Biol. Chem. 239:3706); *Bacillus megaterium;* Serratia (Miyata et al., 1971, Agr. Biol. Chem. 35:460); *Clostridium bifermentans* (MacFarlane et al., 1992, App. Environ. Microbiol. 58:1195–1200), *Legionella pneumophila* (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from *Aspergillus sojae* (Sekine, 1973, Agric. Biol. Chem. 37:1945–1952). Neutral metalloproteases obtained from Aspergillus have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from *Aspergillus oryzae* has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from *Pseudomonas aeruginosa* (Baumann et al., 1993, EMBO J 12:3357–3364) and the insect pathogen *Xenorhabdus luminescens* (Schmidt et al., 1998, Appl. Environ. Microbiol. 54:2793-2797).

Metalloproteases have been devided into several distinct families based primarily on activity and sturcture: 1) water nucleophile; water bound by single zinc ion ligated to two His (within the motif HEXXH) and Glu, His or Asp; 2) water nucleophile; water bound by single zinc ion ligated to His, Glu (within the motif HXXE) and His; 3) water nucleophile; water bound by single zinc ion ligated to His, Asp and His; 4) Water nucleophile; water bound by single zinc ion ligated to two His (within the motif HXXEH) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (*Homo sapiens*), germinal peptidyl-dipeptidase A (*Homo sapiens*), thimet oligopeptidase (*Rattus norvegicus*), oligopeptidase F (*Lactococcus lactis*), mycolysin (*Streptomyces cacaoi*), immune inhibitor A (*Bacillus thuringiensis*), snapalysin (*Streptomyces lividans*), leishmanolysin (*Leishmania major*), microbial collagenase (*Vibrio alginolyticus*), microbial collagenase, class I (*Clostridium perfringens*), collagenase 1 (*Homo sapiens*), serralysin (*Serratia marcescens*), fragilysin (*Bacteroides fragilis*), gametolysin (*Chlamydomonas reinhardtii*), astacin (*Astacus fluviatilis*), adamalysin (*Crotalus adamanteus*), ADAM 10 (*Bos taurus*), neprilysin (*Homo sapiens*), carboxypeptidase A (*Homo sapiens*), carboxypeptidase E (*Bos taurus*), gamma-D-glutamyl-(L)-meso-diaminopimelate peptidase I (*Bacillus sphaericus*), vanY D-Ala-D-Ala carboxypeptidase (*Enterococcus faecium*), endolysin (bacteriophage A118), pitrilysin (*Escherichia coli*), mitochondrial processing peptidase (*Saccharomyces cerevisiae*), leucyl aminopeptidase (*Bos taurus*), aminopeptidase I (*Saccharomyces cerevisiae*), membrane dipeptidase (*Homo sapiens*), glutamate carboxypeptidase (Pseudomonas sp.), Gly-X carboxypeptidase (*Saccharomyces cerevisiae*), O-sialoglycoprotein endopeptidase (*Pasteurella haemolytica*), beta-lytic metalloendopeptidase (*Achromobacter lyticus*), methionyl aminopeptidase I (*Escherichia coli*), X-Pro aminopeptidase (*Escherichia coli*), X-His dipeptidase (*Escherichia coli*), IgA1-specific metalloendopeptidase (*Streptococcus sanguis*), tentoxilysin (*Clostridium tetani*), leucyl aminopeptidase (*Vibrio proteolyticus*), aminopeptidase (*Streptomyces griseus*), IAP aminopeptidase (*Escherichia coli*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), penicillolysin (*Penicillium citrinum*), fungalysin (*Aspergillus fumigatus*), lysostaphin (*Staphylococcus simulans*), beta-aspartyl dipeptidase (*Escherichia coli*), carboxypeptidase Ss1 (*Sulfolobus solfataricus*), FtsH endopeptidase (*Escherichia coli*), glutamyl aminopeptidase (*Lactococcus lactis*), cytophagalysin (Cytophaga sp.), metalloendopeptidase (vaccinia virus), VanX D-Ala-D-Ala dipeptidase (*Enterococcus faecium*), Ste24p endopeptidase (*Saccharomyces cerevisiae*), dipeptidyl-peptidase III (*Rattus norvegicus*), S2P protease (*Homo sapiens*), sporulation factor SpoIVFB (*Bacillus subtilis*), and HYBD endopeptidase (*Escherichia coli*).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoarthritis (Woessner, et al., J. Biol.Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res. 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Bums, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154–8158, 1991), i) aneurysmal aortic disease (Vine, et al., Clin. Sci. 81, 233, 1991), j) birth control (Woessner, et al., Steroids 54, 491, 1989), k) dystrophobic epidermolysis bullosa (Kronberger, et al., J. Invest. Dermatol. 79, 208, 1982), and 1) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

Aspartic Protease

Aspartic proteases have been divided into several distinct families based primarily on activity and structure. These include 1) water nucleophile; water bound by two Asp from monomer or dimer; all endopeptidases, from eukaryote organisms, viruses or virus-like organisms and 2) endopeptidases that are water nucleophile and are water bound by Asp and Asn.

Most of aspartic proteases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteases such as the protease from the AIDS virus (HIV) also called retropepsin. Crystallographic studies have shown that these enzymes are bilobed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme.

In contrast to serine and cysteine proteases, catalysis by aspartic protease do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage. This general acid-base catalysis, which may be called a "push-pull" mechanism leads to the formation of a non covalent neutral tetrahedral intermediate.

Examples of the aspartic protease family of proteins include, but are not limited to, pepsin A (*Homo sapiens*), HIV1 retropepsin (human immunodeficiency virus type 1), endopeptidase (cauliflower mosaic virus), bacilliform virus putative protease (rice tungro bacilliform virus), aspergillopepsin II (*Aspergillus niger*), thermopsin (*Sulfolobus acidocaldarius*), nodavirus endopeptidase (flock house virus), pseudomonapepsin (Pseudomonas sp. 101), signal peptidase II (*Escherichia coli*), polyprotein peptidase (human spumaretrovirus), copia transposon (*Drosophila melanogaster*), SIRE-1 peptidase (*Glycine max*), retrotransposon bs1 endopeptidase (*Zea mays*), retrotransposon peptidase (*Drosophila buzzatii*), Tas retrotransposon peptidase (*Ascaris lumbricoides*), Pao retrotransposon peptidase (*Bombyx mori*), putative proteinase of Skippy retrotransposon (*Fusarium oxysporum*), tetravirus endopeptidase (*Nudaurelia capensis* omega virus), presenilin 1 (*Homo sapiens*).

Proteases and Cancer

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see DeClerck, et al., Ann. N.Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 1993). The use of this and related compounds has been described in Brown, et al., WO-9321942 A2.

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1.

The present invention has substantial similarity (an alternate splicing form) to ATP-metalloprotease in yeast. Three AAA superfamily metalloproteases (YME1L, Afg3p and Rca1p) related to ATP-metalloprotease are localized to the mitochondrial inner membrane where they perform roles in the assembly and turnover of the respiratory chain complexes. Another novel gene YME1L1 has showed that its protein of 716 amino acids has high similarity to all mitochondrial AAA protease, especially to yeast YME1P. It is found that YME1L plays a phylogenetically conserved role in mitochondrial protein metabolism and could be involved in mitochondrial pathologies. Such role may be physiologically associated with hereditary spastic paraplegia and possibly for other neurodegenerative disorders. For a review related to the protein of the present invention, see Coppola et al, Genomics 66 (1), 48–54 (2000); Shah et al., FEBS Lett. 478 (3), 267–270 (2000).

Protease proteins, particularly members of the ATP-dependent metalloprotease subfamily, are a major target for drug action and development. Accordingly, it is valuable to the field of pharmaceutical development to identify and characterize previously unknown members of this subfamily of protease proteins. The present invention advances the state of the art by providing a previously unidentified human protease proteins that have homology to members of the ATP-dependent metalloprotease subfamily.

SUMMARY OF THE INVENTION

The present invention is based in part on the identification of amino acid sequences of human protease peptides and proteins that are related to the ATP-dependent metalloprotease subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate protease activity in cells and tissues that express the protease. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver.

DESCRIPTION OF THE FIGURE SHEETS

FIG. 1 provides the nucleotide sequence of a cDNA molecule or transcript sequence that encodes the protease protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver.

FIG. 2 provides the predicted amino acid sequence of the protease of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the protease protein of the present invention. (SEQ ID NO:3) In addition structure and functional information, such as intron/exon structure, promoter location, etc., is provided where available, allowing one to readily determine specific uses of inventions based on this molecular sequence. 79 SNPs, including 10 indels, have been identified in the gene encoding the protease protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a protease protein or part of a protease protein and are related to the ATP-dependent metalloprotease subfamily. Utilizing these sequences, additional genomic sequences were assembled and transcript and/or cDNA sequences were isolated and characterized. Based on this analysis, the present invention provides amino acid sequences of human protease peptides and proteins that are related to the ATP-dependent metalloprotease subfamily, nucleic acid sequences in the form of transcript sequences, cDNA sequences and/or genomic sequences that encode these protease peptides and proteins, nucleic acid variation (allelic information), tissue distribution of expression, and information about the closest art known protein/peptide/domain that has structural or sequence homology to the protease of the present invention.

In addition to being previously unknown, the peptides that are provided in the present invention are selected based on their ability to be used for the development of commercially important products and services. Specifically, the present peptides are selected based on homology and/or structural relatedness to known protease proteins of the ATP-dependent metalloprotease subfamily and the expression pattern observed. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known ATP-dependent metalloprotease family or subfamily of protease proteins.

SPECIFIC EMBODIMENTS

Peptide Molecules

The present invention provides nucleic acid sequences that encode protein molecules that have been identified as being members of the protease family of proteins and are related to the ATP-dependent metalloprotease subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the protease peptides of the present invention, protease peptides, or peptides/proteins of the present invention.

The present invention provides isolated peptide and protein molecules that consist of, consist essentially of, or comprise the amino acid sequences of the protease peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/ eDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be made/isolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the protease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein. As indicated by the data presented in FIG. 3, the map position was determined to be on chromosome 10 by ePCR.

Allelic variants of a protease peptide can readily be identified as being a human protein having a high degree (significant) of sequence homology/identity to at least a portion of the protease peptide as well as being encoded by the same genetic locus as the protease peptide provided herein. Genetic locus can readily be determined based on the genomic information provided in FIG. 3, such as the genomic sequence mapped to the reference human. As indicated by the data presented in FIG. 3, the map position was determined to be on chromosome 10 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protease peptide encoding nucleic acid molecule under stringent conditions as more fully described below.

FIG. 3 provides information on SNPs that have been identified in a gene encoding the protease protein of the present invention. 79 SNP variants were found, including 10 indels (indicated by a "–") and 1 SNPs in exons. Such SNPs in introns, 5' and 3' of the ORF and outside the ORF may affect control/regulatory elements.

Paralogs of a protease peptide can readily be identified as having some degree of significant sequence homology/identity to at least a portion of the protease peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/identity to at least a portion of the protease peptide as well as being encoded by a gene from another organism. Preferred orthologs will be isolated from mammals, preferably primates, for the development of human therapeutic targets and agents. Such orthologs will be encoded by a nucleic acid sequence that will hybridize to a protease peptide encoding nucleic acid molecule under moderate to stringent conditions, as more fully described below, depending on the degree of relatedness of the two organisms yielding the proteins. As indicated by the data presented in FIG. 3, the map position was determined to be on chromosome 10 by ePCR.

FIG. 3 provides information on SNPs that have been identified in a gene encoding the protease protein of the present invention. 79 SNP variants were found, including 10 indels (indicated by a "–") and 1 SNPs in exons. Such SNPs in introns, 5' and 3' of the ORF and outside the ORF may affect control/regulatory elements.

Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be fully functional or can lack function in one or more activities, e.g. ability to bind substrate, ability to cleave substrate, ability to participate in a signaling pathway, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the protease peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

UTILITY_UTILITY

The potential uses of the peptides of the present invention are based primarily on the source of the protein as well as the class/action of the protein. For example, proteases isolated from humans and their human/mammalian orthologs serve as targets for identifying agents for use in mammalian therapeutic applications, e.g. a human drug, particularly in modulating a biological or pathological response in a cell or tissue that expresses the protease. Experimental data as provided in FIG. 1 indicates that protease proteins of the present invention are expressed in the T cells from T cell leukemia, teratocarcinoma, prostate adenocarcinoma, adrenal gland-cortex carcinoma cell line, placenta,liver adenocarcinoma, retinoblastoma, pooled human meanocyte, fetal heart and pregnant uterus Specifically, a virtual northern blot shows expression in heart and liver. In addition, PCR-based tissue screening panel indicates expression in, and whole liver. A large percentage of pharmaceutical agents are being developed that modulate the activity of protease proteins, particularly members of the ATP-dependent metalloprotease subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. Such uses can readily be determined using the information provided herein, that which is known in the art, and routine experimentation.

The proteins of the present invention (including variants and fragments that may have been disclosed prior to the present invention) are useful for biological assays related to proteases that are related to members of the ATP-dependent metalloprotease subfamily. Such assays involve any of the known protease functions or activities or properties useful for diagnosis and treatment of protease-related conditions that are specific for the subfamily of proteases that the one of the present invention belongs to, particularly in cells and tissues that express the protease. Experimental data as provided in FIG. 1 indicates that protease proteins of the present invention are expressed in the T cells from T cell leukemia, teratocarcinoma, prostate adenocarcinoma, adrenal gland-cortex carcinoma cell line, placenta, liver adenocarcinoma, retinoblastoma, pooled human meanocyte, fetal heart and pregnant uterus Specifically, a virtual northern blot shows expression in heart and liver. In addition, PCR-based tissue screening panel indicates expression in, and whole liver.

The proteins of the present invention are also useful in drug screening assays, in cell-based or cell-free systems. Cell-based systems can be native, i.e., cells that normally express the protease, as a biopsy or expanded in cell culture. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protease can be assayed. Experimental data as provided in FIG. 1 indicates that protease proteins of the present invention are expressed in the T cells from T cell leukemia, teratocarcinoma, prostate adenocarcinoma, adrenal gland-cortex carcinoma cell line, placenta,liver adenocarcinoma, retinoblastoma, pooled human meanocyte, fetal heart and pregnant uterus Specifically, a virtual northern blot shows expression in heart and liver. In addition, PCR-based tissue screening panel indicates expression in, and whole liver.

Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protease. Accordingly, a different set of signal transduction components is available as an end-point assay for activation. This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind to or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protease protein activity identified according to these drug screening assays can be used to treat a subject with a disorder mediated by the protease pathway, by treating cells or tissues that express the protease. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. These methods of treatment include the steps of administering a modulator of protease activity in a pharmaceutical composition to a subject in need of such treatment, the modulator being identified as described herein.

In yet another aspect of the invention, the protease proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al (1993) *Biotechniques* 14:920–924; Iwabuchi et al. (1993) *Oncogene* 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in an appropriate animal model. For example, an agent identified as described herein (e.g., a protease-modulating agent, an antisense protease nucleic acid molecule, a protease-specific antibody, or a protease-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. The method involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. Accordingly, methods for treatment include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protease proteins. Antibodies can be prepared from any region of the peptide as described herein. However, preferred regions will include those involved in function/activity and/or protease/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that protease proteins of the present invention are expressed in the T cells from T cell leukemia, teratocarcinoma, prostate adenocarcinoma, adrenal gland-cortex carcinoma cell line, placenta, liver adenocarcinoma, retinoblastoma, pooled human meanocyte, fetal heart and pregnant uterus Specifically, a virtual northern blot shows expression in heart and liver. In addition, PCR-based tissue screening panel indicates expression in, and whole liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIGS. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre- pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 79 SNPs, including 10 indels, have been identified in the gene encoding the protease protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 10 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that protease proteins of the present invention are expressed in the T cells from T cell leukemia, teratocarcinoma, prostate adenocarcinoma, adrenal gland-cortex carcinoma cell line, placenta,liver adenocarcinoma, retinoblastoma, pooled human meanocyte, fetal heart and pregnant uterus Specifically, a virtual northern blot shows expression in heart and liver. In addition, PCR-based tissue screening panel indicates expression in, and whole liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated. Experimental data as provided in FIG. 1 indicates that protease proteins of the present invention are expressed in the T cells from T cell leukemia, teratocarcinoma, prostate adenocarcinoma, adrenal gland-cortex carcinoma cell line, placenta,liver adenocarcinoma, retinoblastoma, pooled human meanocyte, fetal heart and pregnant uterus Specifically, a virtual northern blot shows expression in heart and liver. In addition, PCR-based tissue screening panel indicates expression in, and whole liver.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Experimental data as provided in FIG. 1 indicates that protease proteins of the present invention are expressed in the T cells from T cell leukemia, teratocarcinoma, prostate adenocarcinoma, adrenal gland-cortex carcinoma cell line, placenta, liver adenocarcinoma, retinoblastoma, pooled human meanocyte, fetal heart and pregnant uterus Specifically, a virtual northern blot shows expression in heart and liver. In addition, PCR-based tissue screening panel indicates expression in, and whole liver. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein. Experimental data as provided in FIG. 1 indicates expression in the T cells from T cell leukemia, teratocarcinoma, prostate adenocarcinoma, adrenal gland-cortex carcinoma cell line, placenta, liver, adenocarcinoma, retinoblastoma, pooled human meanocyte, fetal heart and pregnant uterus, and whole liver.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. FIG. 3 provides information on SNPs that have been identified in a gene encoding the protease protein of the present invention. 79 SNP variants were found, including 10 indels (indicated by a "−") and 1 SNPs in exons. Such SNPs in introns, 5' and 3' of the ORF and outside the ORF may affect control/regulatory elements. As indicated by the data presented in FIG. 3, the map position was determined to be on chromosome 10 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al, *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. A DNA antisense nucleic acid molecule is designed to be complementary to a region of the gene involved in transcription, preventing transcription and hence production of protease protein. An antisense RNA or DNA nucleic acid molecule would hybridize to the mRNA and thus block translation of mRNA into protease protein. FIG. 3 provides information on SNPs that have been identified in a gene encoding the protease protein of the present invention. 79 SNP variants were found, including 10 indels (indicated by a "–") and 1 SNPs in exons. Such SNPs in introns, 5' and 3' of the ORF and outside the ORF may affect control/regulatory elements.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. Experimental data as provided in FIG. 1 indicates that protease proteins of the present invention are expressed in the T cells from T cell leukemia, teratocarcinoma, prostate adenocarcinoma, adrenal gland-cortex carcinoma cell line, placenta, liver adenocarcinoma, retinoblastoma, pooled human meanocyte, fetal heart and pregnant uterus Specifically, a virtual northern blot shows expression in heart and liver. In addition, PCR-based tissue screening panel indicates expression in, and whole liver. For example, the kit can comprise reagents such as a labeled or labelable nucleic acid or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS: 1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention. FIG. 3 provides information on SNPs that have been identified in a gene encoding the protease protein of the present invention. 79 SNP variants were found, including 10 indels (indicated by a "–") and 1 SNPs in exons. Such SNPs in introns, 5' and 3' of the ORF and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2*nd, ed*n., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2*nd, ed.*, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production.

Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is mutations that substantially or completely eliminate one or more protease protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes an amino acid sequence comprising SEQ ID NO:2;
   (b) a nucleotide sequence consisting of the nucleic acid sequence of SEQ ID NO: 1;
   (c) a nucleotide sequence consisting of the nucleic acid sequence of SEQ ID NO: 3; and
   (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. An isolated polynucleotide consisting of a nucleotide sequence set forth in SEQ ID NO: 1.

6. An isolated polynucleotide consisting of a nucleotide sequence set forth in SEQ ID NO: 3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO: 2 may be expressed by a cell transformed with said vector.

9. A vector according to claim 8, wherein said isolated nucleic acid molecule is operatively linked to a promoter sequence.

10. An isolated nucleic acid molecule comprising a nucleotide sequence selected from the group consisting of:
    (a) a nucleotide sequence that encodes SEQ ID NO:2;
    (b) a nucleotide sequence comprising the nucleic acid sequence of SEQ ID NO: 1;
    (c) a nucleotide sequence consisting of the nucleic acid sequence of SEQ ID NO: 3; and
    (d) a nucleotide sequence that is completely complementary to a nucleotide sequence of (a)–(c).

11. A nucleic acid vector comprising a nucleic acid molecule of claim 10.

12. A host cell containing the vector of claim 11.

13. A process for producing a polypeptide comprising culturing the host cell of claim 12 under conditions sufficient for the production of said polypeptide, and recovering the peptide from the host cell culture.

14. A vector according to claim 11, wherein said vector is selected from the group consisting of a plasmid, virus, and bacteriophage.

15. A vector according to claim 11, wherein said isolated nucleic acid molecule is inserted into said vector in proper orientation and correct reading frame such that the protein of SEQ ID NO: 2 maybe expressed by a cell transformed with said vector.

16. A vector according to claim 15, wherein said isolated nucleic acid molecule is operatively linked to a promoter sequence.

17. An isolated nucleic acid molecule encoding a human protease peptide, said nucleic acid molecule sharing at least 95 percent sequence homology with a nucleic acid molecule shown in SEQ ID NOS: 1 or 3.

18. A nucleic acid vector comprising a nucleic acid molecule of claim 17.

19. A host cell containing the vector of claim 18.

20. A process for producing a polypeptide comprising culturing the host cell of claim 19 under conditions sufficient for the production of said polypeptide, and recovering the peptide from the host cell culture.

21. A vector according to claim 18, wherein said vector is selected from the group consisting of a plasmid, virus, and bacteriophage.

22. A vector according to claim 18, wherein said isolated nucleic acid molecule is inserted into said vector in proper orientation and correct reading frame such that said protease peptide may be expressed by a cell transformed with said vector.

23. A vector according to claim 22, wherein said isolated nucleic acid molecule is operatively linked to a promoter sequence.

* * * * *